(12) United States Patent
Lapointe et al.

(10) Patent No.: US 11,027,242 B2
(45) Date of Patent: Jun. 8, 2021

(54) NANOFILTRATION MEMBRANES AND METHODS OF USE

(71) Applicant: Novomer, Inc., Boston, MA (US)

(72) Inventors: Robert E. Lapointe, Syracuse, NY (US); Scott D. Allen, Ithaca, NY (US); Han Lee, Ithaca, NY (US); Thomas Widzinski, Ithaca, NY (US); Jay J. Farmer, Ithaca, NY (US)

(73) Assignee: Novomer, Inc., Rochester, NY (US)

( * ) Notice: Subject to any disclaimer, the term of this patent is extended or adjusted under 35 U.S.C. 154(b) by 303 days.

(21) Appl. No.: 16/283,257

(22) Filed: Feb. 22, 2019

(65) Prior Publication Data

US 2019/0255488 A1    Aug. 22, 2019

Related U.S. Application Data

(63) Continuation of application No. 15/176,110, filed on Jun. 7, 2016, now Pat. No. 10,245,559, which is a continuation of application No. PCT/US2014/069066, filed on Dec. 8, 2014.

(60) Provisional application No. 61/913,268, filed on Dec. 7, 2013.

(51) Int. Cl.
| | |
|---|---|
| *B01D 67/00* | (2006.01) |
| *B01D 61/02* | (2006.01) |
| *B01D 71/56* | (2006.01) |
| *B01D 71/60* | (2006.01) |
| *B01D 71/64* | (2006.01) |
| *B01D 71/70* | (2006.01) |
| *B01D 71/76* | (2006.01) |
| *B01D 71/82* | (2006.01) |
| *C07D 305/12* | (2006.01) |

(52) U.S. Cl.
CPC ....... *B01D 67/0093* (2013.01); *B01D 61/027* (2013.01); *B01D 71/56* (2013.01); *B01D 71/60* (2013.01); *B01D 71/64* (2013.01); *B01D 71/70* (2013.01); *B01D 71/76* (2013.01); *B01D 71/82* (2013.01); *C07D 305/12* (2013.01); *B01D 2323/30* (2013.01); *B01D 2323/36* (2013.01); *B01D 2325/30* (2013.01)

(58) Field of Classification Search
CPC ......... C07C 51/09; C07C 67/37; C07C 57/04; C07D 305/12; C08G 63/08; B01D 2323/30; B01D 61/027; B01D 71/64; B01J 2231/34; C07F 9/65746; Y02P 20/10; Y02P 20/582; Y02P 20/584; C08F 8/40

See application file for complete search history.

(56) References Cited

U.S. PATENT DOCUMENTS

| | | |
|---|---|---|
| 2,352,641 A | 7/1944 | Küng |
| 2,361,036 A | 10/1944 | Küng |
| 2,376,704 A | 5/1945 | Küng |
| 2,422,728 A | 6/1947 | Gresham et al. |
| 2,449,989 A | 9/1948 | Gresham |
| 2,449,991 A | 9/1948 | Gresham et al. |
| 2,449,992 A | 9/1948 | Gresham et al. |
| 2,449,993 A | 9/1948 | Gresham et al. |
| 2,449,995 A | 9/1948 | Gresham et al. |
| 2,466,501 A | 4/1949 | Steadman et al. |
| 2,499,988 A | 3/1950 | Cox |
| 2,499,990 A | 3/1950 | Dehmel |
| 2,510,423 A | 6/1950 | Shaver |
| 2,526,554 A | 10/1950 | Gresham et al. |
| 2,548,155 A | 4/1951 | Gresham et al. |
| 2,568,635 A | 9/1951 | Jansen et al. |
| 2,568,636 A | 9/1951 | Japs |
| 2,623,067 A | 12/1952 | Beears et al. |
| 2,623,070 A | 12/1952 | Jansen |
| 2,649,438 A | 8/1953 | Bruson |
| 2,749,355 A | 6/1956 | Jones |
| 3,002,017 A | 9/1961 | Wearsch et al. |
| 3,124,609 A | 3/1964 | Higdon |
| 3,157,693 A | 11/1964 | Wheeler et al. |
| 3,176,042 A | 3/1965 | Schnizer et al. |
| 3,671,305 A | 6/1972 | Brown et al. |
| 3,932,500 A | 1/1976 | Duembgen et al. |
| 3,951,815 A | 4/1976 | Wrasidlo |
| 4,828,652 A | 5/1989 | Schropp |
| 4,960,517 A | 10/1990 | Cadotte |
| 5,310,948 A | 5/1994 | Drent et al. |
| 5,359,081 A | 10/1994 | Drent et al. |
| 5,582,725 A | 12/1996 | McCray et al. |
| 6,084,122 A | 7/2000 | Garza et al. |
| 6,084,128 A | 7/2000 | Warner et al. |

(Continued)

FOREIGN PATENT DOCUMENTS

| | | |
|---|---|---|
| CN | 102421821 A | 4/2012 |
| GB | 994091 A | 6/1965 |

(Continued)

OTHER PUBLICATIONS

Office Action in co-pending IN Application No. 201647023074, dated Aug. 28, 2020; 8 pages.

(Continued)

*Primary Examiner* — Ana M Fortuna

(74) *Attorney, Agent, or Firm* — Young Basile Hanlon & MacFarlane, P.C.

(57) ABSTRACT

The present invention provides nanofiltration membranes with reduced chemical reactivity that can be utilized in manufacturing processes where reactive feedstocks and/or products are utilized or produced. Methods of making and using the membranes are also provided.

17 Claims, No Drawings

(56) References Cited

U.S. PATENT DOCUMENTS

| | | | |
|---|---|---|---|
| 6,207,022 B1 | 3/2001 | Dockner et al. | |
| 6,350,819 B1* | 2/2002 | Tulchinsky | C07C 45/50 525/330.4 |
| 6,852,865 B2 | 2/2005 | Coates et al. | |
| 7,420,064 B2* | 9/2008 | Luinstra | B01J 31/122 502/152 |
| 8,445,703 B2* | 5/2013 | Allen | C07C 67/30 549/328 |
| 9,206,144 B2* | 12/2015 | Allen | C07C 67/30 |
| 9,493,391 B2 | 11/2016 | Allen et al. | |
| 9,914,689 B2 | 3/2018 | Porcelli et al. | |
| 10,099,988 B2 | 10/2018 | Farmer et al. | |
| 10,099,989 B2 | 10/2018 | Sookraj | |
| 10,221,150 B2 | 3/2019 | Farmer et al. | |
| 10,221,278 B2 | 3/2019 | Lee et al. | |
| 10,245,559 B2* | 4/2019 | Lapointe | B01D 71/76 |
| 10,662,283 B2* | 5/2020 | Farmer | C08G 63/823 |
| 10,703,702 B2* | 7/2020 | Sookraj | B01J 19/1862 |
| 2005/0014977 A1 | 1/2005 | Drent et al. | |
| 2007/0039874 A1 | 2/2007 | Kniajanski et al. | |
| 2007/0161806 A1 | 7/2007 | Preishuber-Pflugl et al. | |
| 2009/0173694 A1 | 7/2009 | Peinemann et al. | |
| 2010/0323573 A1* | 12/2010 | Chu | B01D 71/08 442/153 |
| 2011/0226697 A1 | 9/2011 | McLellan et al. | |
| 2013/0004454 A1* | 1/2013 | Weiss | B01D 53/228 424/78.09 |
| 2013/0165670 A1 | 6/2013 | Allen et al. | |
| 2013/0299417 A1 | 11/2013 | Luchinger et al. | |
| 2015/0141693 A1 | 5/2015 | Allen et al. | |
| 2016/0141693 A1* | 5/2016 | Hotta | H01M 8/04164 429/414 |
| 2016/0288057 A1 | 10/2016 | Lapointe et al. | |
| 2017/0029352 A1 | 2/2017 | Sookraj et al. | |
| 2018/0016219 A1 | 1/2018 | Farmer et al. | |
| 2018/0022677 A1* | 1/2018 | Sookraj | C08G 63/08 562/599 |
| 2018/0029005 A1 | 2/2018 | Sookraj | |
| 2018/0030014 A1 | 2/2018 | Sookraj et al. | |
| 2018/0030015 A1 | 2/2018 | Farmer et al. | |
| 2018/0030201 A1 | 2/2018 | Farmer et al. | |
| 2018/0057619 A1 | 3/2018 | Sookraj | |
| 2018/0094100 A1* | 4/2018 | Farmer | C08G 63/08 |
| 2018/0354881 A1 | 12/2018 | Farmer et al. | |
| 2018/0354882 A1 | 12/2018 | Sookraj | |
| 2019/0030520 A1 | 1/2019 | Lee | |

FOREIGN PATENT DOCUMENTS

| | | |
|---|---|---|
| JP | 3-186326 A | 8/1991 |
| JP | 2008-515668 A | 5/2008 |
| JP | 2013-521387 A | 6/2013 |
| JP | 2015-511947 A | 4/2015 |
| JP | 2015-523363 A | 8/2015 |
| WO | 2006/087556 A1 | 8/2006 |
| WO | 2007/001405 A2 | 1/2007 |
| WO | 2010/118128 A1 | 10/2010 |
| WO | 2010/137974 A1 | 12/2010 |
| WO | 2011/110441 A2 | 9/2011 |
| WO | 2012/030619 A1 | 3/2012 |
| WO | 2012/158573 A1 | 11/2012 |
| WO | 2013/063191 A1 | 5/2013 |
| WO | 2013/068846 A1 | 5/2013 |
| WO | 2013/122905 A1 | 8/2013 |
| WO | 2013/126375 A1 | 8/2013 |
| WO | 2013/180659 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/136638 A1 | 7/2018 |
| WO | 2018/170006 A1 | 9/2018 |
| WO | 2019/051184 A1 | 3/2019 |

OTHER PUBLICATIONS

Church, et al., "Carbonylation of Heterocycles by Homogeneous Catalysts", Chemical Communications, vol. 21, No. 7, 2007, pp. 657-674.

Kowalczuk et al., "New Reactions of Potassium Naphthalenide with $\beta$-, $\gamma$-, and ??-Lactones: An Efficient Route to $\alpha$-Alkyl $\gamma$- and ??-Lactones and $\alpha,\beta$-Unaturated Carboxylic Acid Esters", The Journal of Organic Chemistry, vol. 57, 1992, pp. 389-391.

Extended European Search Report received for European Patent Application No. 14868326.1, dated Nov. 21, 2017, 23 pages.

International Preliminary Report on Patentability received for PCT Patent Application No. PCT/US2014/069066, dated Jun. 16, 2016, 8 pages.

International Search Report and Written Opinion received for PCT Patent Application No. PCT/US2014/069066, dated Mar. 16, 2015, 10 pages.

Lingbo, Li, "Preparation of PA/PDMS Crosslinked Hybridization Solvent-Resistant Nanofiltration Membrane and the Study on the Properties thereof", Chinese Masters Theses Full-text Database, Engineering Science and Technology I, No. 11, Nov. 15, 2013, 3 pages.

Lingbo, Li, "Preparation and Performances of Cross-Linked PA/PDMS Hybrid Membrane for Solvent-Resistant Nanofiltration ", Chinese Engineering, School of Chemical Engineering and Energy, Apr. 2013, 49 pages.

Non-Final Office Action received for U.S. Appl. No. 15/176,110, dated Jul. 2, 2018, 6 pages.

Notice of Allowance received for U.S. Appl. No. 15/176,110, dated Nov. 14, 2018, 8 pages.

Partial Supplementary Search Report received for European Patent Application No. 14868326.1, dated Aug. 2, 2017, 8 pages.

Stafie et al., "Effect of PDMS Cross-Linking Degree on the Permeation Performance of PAN/PDMS Composite Nanofiltration Membranes", Separation and Purification Technology, vol. 45, 2005, pp. 220-231.

Vanherck et al., "A Simplified Diamine Crosslinking Method for PI Nanofiltration Membranes", Journal of Membrane Science, vol. 353, 2010, pp. 135-143.

Vanherck et al., "Crosslinking Polyimides for Membrane Applications: A Review", Progress in Polymer Science, vol. 38, 2013, pp. 874-896.

Xiao et al., "The Strategies of Molecular Architecture and Modification of Polyimide-Based Membrane for $CO_2$ Removal from Natural Gas—A Review", Progress in Polymer Science, vol. 34, 2009, pp. 561-580.

* cited by examiner

NANOFILTRATION MEMBRANES AND METHODS OF USE

CROSS-REFERENCE TO RELATED APPLICATIONS

This application is a continuation application of U.S. patent application Ser. No. 15/176,110, filed Jun. 7, 2016, which is a continuation of International Application PCT/US2014/069066, with an international filing date of Dec. 8, 2014, which claims priority to and the benefit of U.S. Provisional Application No. 61/913,268, filed Dec. 7, 2013, which are hereby incorporated by reference in their entirety.

FIELD OF THE INVENTION

The invention pertains to the field of chemical processing. More particularly, the invention pertains to nanofiltration membranes suitable for use in contact with reactive chemical compounds and methods of manufacturing and using such membranes.

BACKGROUND OF THE INVENTION

The use of nanofiltration (NF) membranes which are able to separate components of homogenous solutions based on molecular size has been increasing in recent years. Though most applications of NF membranes still pertain to filtration of aqueous mixtures, there is growing interest in applying nanofiltration to chemical processes conducted in organic solvents.

Applying NF to solvent-based processes requires membranes that do not degrade or dissolve in the presence of organic solvents. Such Organic Solvent Nanofiltration (OSN) membranes are manufactured utilizing various materials. A challenge in utilizing OSN membranes in chemical processes arises from the need of the membrane to simultaneously satisfy numerous criteria: the membrane should be solvent compatible, should be capable of performing the desired separation while maintaining a high filtration rate, should be effective for extended periods of time, and should be inert to the components in the process.

The last point has proven to be a particular challenge in processes that utilize reactive feedstocks and/or produce reactive products. As such, there remains a need for nanofiltration membranes that have low reactivity.

SUMMARY OF THE INVENTION

In one aspect, the present invention provides nanofiltration membranes with reduced chemical reactivity that can be utilized in manufacturing processes where reactive feedstocks and/or products are utilized or produced.

One such process is the carbonylation of ethylene oxide (EO) to provide beta propiolactone (BPL). Both the EO and the BPL are highly reactive electrophiles and both are also capable of undergoing ring opening polymerization. In certain embodiments, the present invention provides novel nanofiltration membranes that are chemically inert or have reduced reactivity to EO and BPL.

In another aspect, the present invention provides methods of making nanofiltration membranes having reduced chemical reactivity. In certain embodiments, such methods comprise a step of treating a membrane material with reagents that modify reactive functional groups present on or in the membrane. In certain embodiments, such methods are performed on an existing membrane composition, while in other embodiments the step of modifying the reactive groups takes place at an earlier stage during the manufacture of the membrane or its constituent parts.

In another aspect, the present invention encompasses chemical processes utilizing the inventive membranes. In certain embodiments, such processes involve contacting a process stream containing one or more reactive chemicals with a modified nanofiltration membrane having reduced reactivity toward those reactive chemicals. In certain embodiments, the process stream comprises beta propiolactone. In certain embodiments, the process stream comprises ethylene oxide. In certain embodiments the process stream further comprises a carbonylation catalyst. In certain embodiments, the present invention encompasses methods for the continuous flow production of beta propiolactone, succinic anhydride, polypropiolactone, beta butyrolactone, poly-3-hydroxybutyrate, acrylic acid, acrylate esters or derivatives thereof from an epoxide feedstock.

Definitions

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

Certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions including one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation and not aromatic. Unless otherwise specified, aliphatic groups contain 1-30 carbon atoms. In certain embodiments, aliphatic groups contain 1-12 carbon atoms.

In certain embodiments, aliphatic groups contain 1-8 carbon atoms. In certain embodiments, aliphatic groups contain 1-6 carbon atoms. In some embodiments, aliphatic groups contain 1-5 carbon atoms; in some embodiments, aliphatic groups contain 1-4 carbon atoms; in yet other embodiments aliphatic groups contain 1-3 carbon atoms; and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl) alkyl or (cycloalkyl)alkenyl.

The term "heteroaliphatic", as used herein, refers to aliphatic groups where one or more carbon atoms are independently replaced by one or more atoms selected from the group consisting of oxygen, sulfur, nitrogen, phosphorus, and boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle", "hetercyclyl", "heterocycloaliphatic", or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides include a single oxirane moiety. In certain embodiments, epoxides include two or more oxirane moieties.

The term "acrylate" or "acrylates" as used herein refers to any acyl group having a vinyl group adjacent to the acyl carbonyl. The terms encompass mono-, di-, and tri-substituted methacrylate, ethacrylate, cinnamate (3-phenylacrylate), crotonate, tiglate, and senecioate. The term "polymer", as used herein, refers to a molecule of high relative molecular mass, the structure of which includes the multiple repetition of units derived, actually or conceptually, from molecules of low relative molecular mass. In certain embodiments, a polymer includes only one monomer species (e.g., polyethylene oxide). In certain embodiments, a polymer of the present invention is a co-polymer, terpolymer, heteropolymer, block co-polymer, or tapered heteropolymer of one or more epoxides.

The term "unsaturated", as used herein, means that a moiety has one or more double or triple bonds.

The term "alkyl", as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n propyl, isopropyl, n butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl", as used herein, denotes a monovalent group derived from a straight or branched chain aliphatic moiety having at least one carbon carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl", as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties, where the rings contain only carbon atoms. Unless otherwise specified, carbocycles may be saturated, partially unsaturated or aromatic, and contain 3 to 20 carbon atoms. The terms "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. Representative carbocycles include cyclopropane, cyclobutane, cyclopentane, cyclohexane, bicyclo[2,2,1]heptane, norbornene, phenyl, cyclohexene, naphthalene, and spiro[4.5] decane.

The term "aryl" used alone or as part of a larger moiety as in "aralkyl", "aralkoxy", or "aryloxyalkyl", refers to monocyclic and polycyclic ring systems having a total of five to 20 ring members, where at least one ring in the system is aromatic and where each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms, having 6, 10, or 14 Ix electrons shared in a cyclic array, and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, where the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or a 7-14-membered bicyclic heterocyclic moiety that is either saturated, partially unsaturated, or aromatic and has, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur, and nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, where the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently a halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_4N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)N(R^\circ)_2$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR)R^\circ$; $-C(O)C(O)R^\circ$; $-C(O)CH_2C(O)R^\circ$; $-C(NOR)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OX)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, where each $R^\circ$ may be substituted as defined below and is independently a hydrogen, $C_{1-8}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently a halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-4}C(O)N(R^\circ)_2$; $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ where each $R^\bullet$ is unsubstituted or, where preceded by "halo", is substituted only with one or more halogens, and is independently selected from $C_{1-4}$ aliphatic, $-CH_2Ph$, $-O(CH_2)_{0-1}Ph$, and a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, =NNHS(O)$_2$R*, =NR*, =NOR*, —O(C(R*$_2$))$_{2-3}$O—, or —S(C(R*$_2$))$_{2-3}$S—, where each independent occurrence of R* is selected from a hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: O(CR*$_2$)$_{2-3}$O—, where each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, where each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; where each R$^\dagger$ is independently a hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently a halogen, —R•, -(haloR•), —OH, —OR•, —O(haloR•), —CN, —C(O)OH, —C(O)OR•, —NH$_2$, —NHR•, —NR•$_2$, or —NO$_2$, where each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance, the presence of which increases the rate of a chemical reaction, while not being consumed or undergoing a permanent chemical change itself.

As used herein, the term "about" preceding one or more numerical values means the numerical value ±5%.

DETAILED DESCRIPTION OF THE INVENTION

Various materials are currently used to (or have been described as suitable for) the manufacture organic solvent-compatible nanofiltration membranes (OSNs). The most common membrane types are polysiloxane-based membranes, polyimide membranes, and polyamide imide membranes. In each case, it is common for the polymer or co-polymer making up the membrane to be cross-linked to prevent swelling in polar organic solvents and/or to control the filtration pore size in the membrane.

Such cross-linking improves solvent resistance, but the inventors have found that residual unreacted functional groups from the cross-linking process lead to problems in certain applications where reactive chemicals are present in the process stream being treated with such membranes. Additionally, other components used in the manufacture of the membranes can contain reactive functional groups in addition to those arising from cross-linking processes. For example, materials such as polyesters and polyimides are sometimes utilized for construction of the membrane or its support. These polymers or co-polymers may also contain reactive functional groups such as carboxylates, hydroxyl groups, or amines.

Without being bound by theory or limiting the scope of the invention, it is believed that such membranes are unsuitable for use in the presence of highly reactive compounds because residual functional groups in the membrane react with reactive components of the process stream thereby fouling the stream and/or the membrane. For example, unreacted nucleophilic functional groups from the materials of construction or the cross-linking processes react with electrophiles in the process stream and/or unreacted electrophilic functional groups from the materials of construction or the cross-linking processes react with nucleophiles in the process stream. Examples of each category have been encountered by the inventors during the development of a continuous catalytic process for reaction of ethylene oxide (EO) with carbon monoxide (CO) to produce beta propiolactone (BPL). EO and BPL are both capable of undergoing ring opening polymerization in the presence of nucleophiles, while the carbonylation catalysts are sensitive to both nucleophiles and certain electrophiles. It has been found that commercially-available nanofiltration membranes are prone to react with one or more of the BPL, EO and catalyst in this process. In the case of reaction with BPL and EO, this results in polyester, polyether, or mixed polyether/polyester chains growing on or within the membrane and ultimately leads to diminished performance and/or membrane failure. In the case of reaction with catalyst, the result is diminishment or destruction of catalyst activity. Our solution to this problem is generally applicable to nanofiltration processes involving reactive chemicals and can be applied to applications beyond EO carbonylation. As such, although EO carbonylation is used herein to demonstrate the principal and advantages of the invention, the scope of the invention is not limited to this process.

In one aspect, the present invention provides nanofiltration membranes with reduced chemical reactivity. Such membranes are advantageous in that they can be utilized in manufacturing processes where reactive feedstocks and/or products are utilized or produced.

Siloxane-Based OSN Membrane Compositions

In certain embodiments, the inventive nanofiltration membranes are polysiloxane-based membranes. A variety of polysiloxane polymer or co-polymer composites have been utilized in the construction of OSN membranes. Typical composites are based on mixing the polydimethylsiloxane polymer (PDMS) with materials such as inorganic solids (zeolites, silicas, clays, montmorillonite, mica, zinc oxide, and silicalite, carbon nanotubes and the like), or with other polymers such as polyacrylonitrile, poly(vinylidene fluoride) and poly(ether imide).

Both the polysiloxane and the composite-forming materials in these systems can have residual reactive functional groups. For example, the polysiloxane chains are typically intended to terminate in chemically inert —O—SiR$_3$ groups, however some polysiloxanes contain residual —Si(R)$_2$—

OH end groups, where R is an optionally substituted aliphatic or optionally substituted aryl group. In addition the polysiloxane polymers or co-polymer in OSN membranes are typically cross-linked by incorporation of multiply reactive cross-linking agents such as $MeSiCl_3$ or by physical methods such as thermal treatment or irradiation with plasmas, electron beams or lasers. Incomplete reaction of chemical cross-linkers may leave electrophilic Si—Cl functional groups in the membrane, while physical methods can create additional reactive functional groups such as Si—OH containing groups or other reactive moieties in the polymer or co-polymer. In addition, the composite-forming component of the membrane formulations may be chemically reactive.

In certain embodiments, the present invention encompasses polysiloxane-based OSN membranes characterized in that they contain essentially no, or very little, free —Si—OH containing functional groups. In certain embodiments, the presence of such Si—OH containing groups is measured by methods known in the art, for example by titrimetric methods. In certain embodiments, the polysiloxane-based OSN membranes of the present invention are characterized in that they contain less than 100 µmol of free Si—OH containing groups per gram of polyimide. In certain embodiments, the polysiloxane-based OSN membranes of the present invention are characterized in that they contain less than 75 µmol, less than 50 µmol, less than 40 µmol, less than 30 µmol, less than 25 µmol, less than 20 µmol, less than 15 µmol, less than 10 µmol, less than 5 µmol, or less than 1 µmol of free —SiOH containing groups per gram of polysiloxane. In certain embodiments, the polysiloxane-based OSN membranes of the present invention are characterized in that they contain less than 500 nmol of free —SiOH containing groups per gram of polysiloxane. In certain embodiments, the polysiloxane-based OSN membranes of the present invention are characterized in that they contain less than 400 nmol, less than 300 nmol, less than 250 nmol, less than 200 nmol, less than 150 nmol, less than 100 nmol, less than 50 nmol, less than 40 nmol, less than 30 nmol, less than 20 nmol, less than 10 nmol, less than 5 nmol, or less than 1 nmol of free —SiOH containing groups per gram of polysiloxane.

In certain embodiments, the inventive polysiloxane-based OSN membranes are produced by performing an additional step after cross-linking of the polysiloxane component of the membrane. In certain embodiments, such membranes are made by a process of producing a PDMS composite with at least one other solid, performing one or more steps to cross-link the PDMS polymer or co-polymer (for example thermal, chemical or irradiative treatment), and then performing a passivating step comprising treating the membrane with a reagent reactive toward Si—OH containing groups. In certain embodiments, the reagent reactive toward SiOH containing groups comprises a compound of formula $R_3SiX^a$, where each R is independently any optionally substituted aliphatic or aryl group and $X^a$ is halogen. In certain embodiments, the reagent reactive toward SiOH containing groups comprises $R_3SiCl$. In certain embodiments, the reagent reactive toward SiOH containing groups comprises $Me_3SiCl$. In certain embodiments, the reagent reactive toward SiOH containing groups comprises a compound of formula $(R_3Si)_2NH$, where R is optionally substituted aliphatic or optionally substituted aryl group. In certain embodiments, the reagent reactive toward SiOH containing groups comprises hexamethyldisilazane.

In certain embodiments, the inventive polysiloxane-based OSN membranes further comprise one or more solid materials acting as a support for the polysiloxane polymer or co-polymer, or forming a composite structure therewith. In certain embodiments, the support or composite-forming materials in the inventive OSN membranes are characterized in that they are essentially free of —OH, —$CO_2H$, and —NH functional groups. In certain embodiments, such membranes comprise composites with inorganic solid oxides characterized in that the surfaces of the inorganic solids are essentially free of —OH functional groups. In certain embodiments, these compositions are the result of a process of producing a PDMS composite with at least one other solid, wherein a passivating step is performed after the composite is formed. In certain embodiments, the process of passivating comprises treating the composite membrane with a reagent reactive toward —OH groups. In certain embodiments, the step of treating the composite with a reagent reactive toward OH groups comprises treating the composite with a reagent of the formula $R_3SiX^a$ where R is an optionally substituted aliphatic or optionally substituted aryl group and $X^a$ is a halogen. In certain embodiments, the step of treating the composite with a reagent reactive toward —OH groups comprises treating the composite with a reagent selected from the group consisting of an alkyl chloride, alkyl bromide, alkyl iodide, alkyl sulfonate ester, sulfonyl chloride, sulfonic acid anhydride, isocyanate, acid chloride, acid anhydride, alkyl chloroformate and aryl chloroformate.

In certain embodiments, provided is a nanofiltration membrane comprising a polysiloxane polymer or co-polymer, wherein the polysiloxane polymer or co-polymer comprises less than 500 nmol of free —Si(OH)— containing groups per gram of polysiloxane. In certain embodiments, the nanofiltration comprises polydimethylsiloxane. In certain embodiments of the nanofiltration membrane, the polysiloxane polymer or co-polymer is crosslinked. In certain embodiments of the nanofiltration membrane, the polysiloxane polymer or co-polymer is treated with a reagent reactive toward OH groups, wherein the reagent is an alkyl chloride, alkyl bromide, alkyl iodide, alkyl sulfonate ester, sulfonyl chloride, sulfonic acid anhydride, isocyanate, acid chloride, acid anhydride, alkyl chloroformate, aryl chloroformate or $R_3SiX^a$, wherein R is an aliphatic or aryl group and $X^a$ is halogen.

Polyimide-Based OSN Membrane Compositions

In other embodiments, inventive OSN membranes of the present invention comprise polyimide-based membranes. Like the polysiloxane membranes described above, polyimide membranes are typically cross-linked to increase their solvent resistance—without cross-linking polyimides swell or dissolve in many organic solvents. One common method of cross-linking polyimide membranes is to treat them with diamines. Scheme 1 shows how the diamine cross-linking process is believed to work:

SCHEME 1

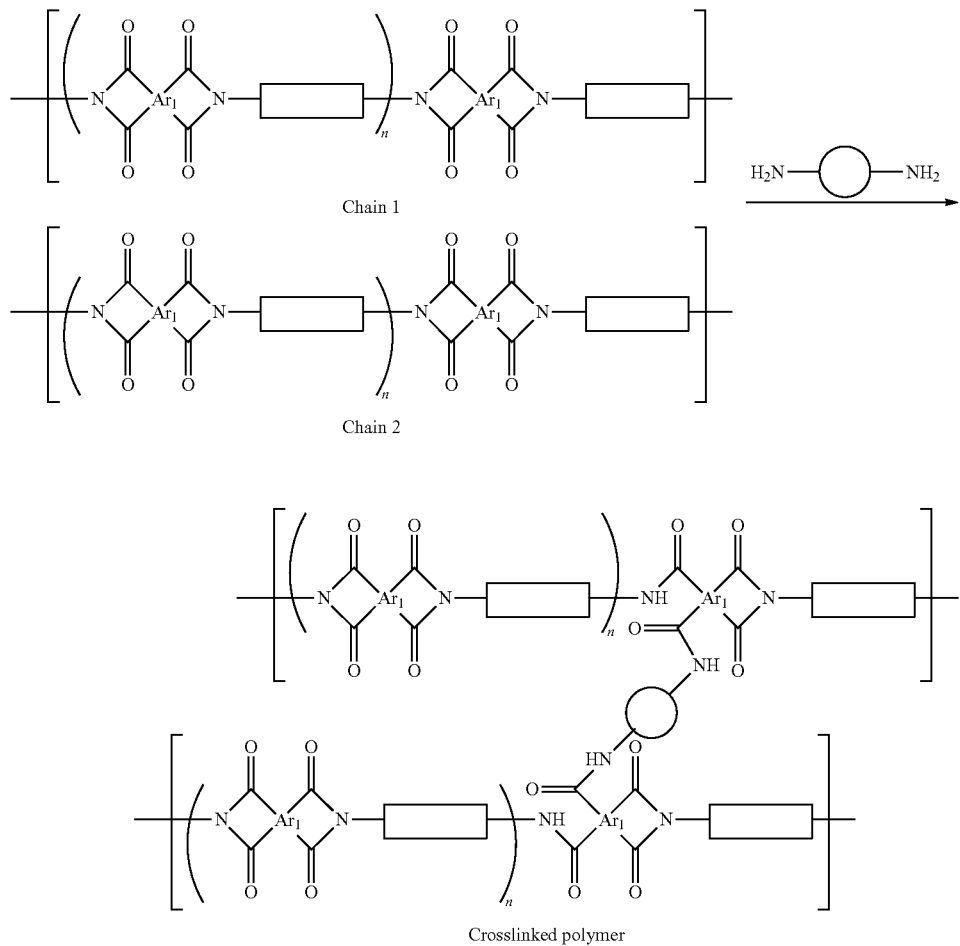

Crosslinked polymer

This leads to two potential problems: first, if the cross-linking process is not absolutely complete, the membrane will contain residual primary amine groups:

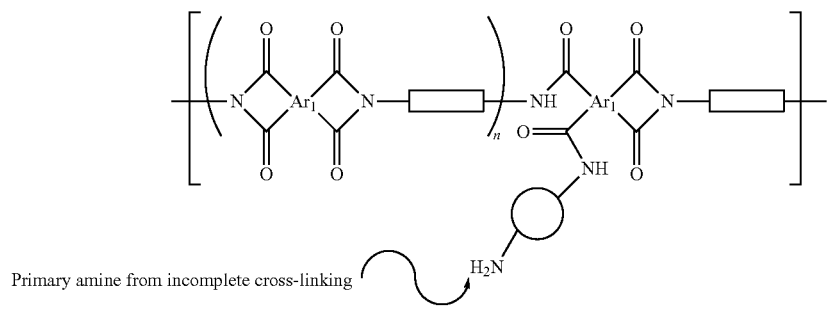

Primary amine from incomplete cross-linking

As described above, such amines are incompatible with process streams containing electrophiles.

In the case where the membrane is to be used in the presence of very strongly electrophilic compounds, a second problem may arise from reactivity of the two secondary amide groups that are formed at each site of cross-linking. These amides have increased nucleophilicity relative to the starting imide functional groups they replace:

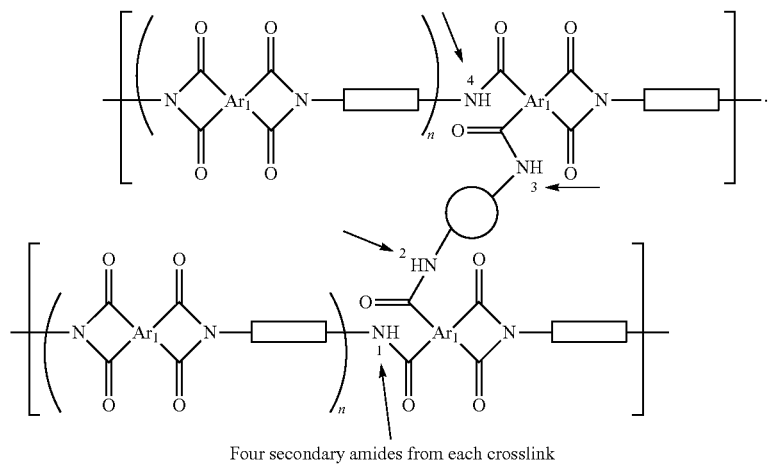

Four secondary amides from each crosslink

The present invention provides solutions to both of these problems. The first problem is overcome by treating the membrane to block or remove the residual amine moieties resulting from incomplete crosslinking. This can be done by treating with end-capping agents after the cross-linking process or by treating with reagents that remove the nitrogen atom altogether:

Prior art membrane

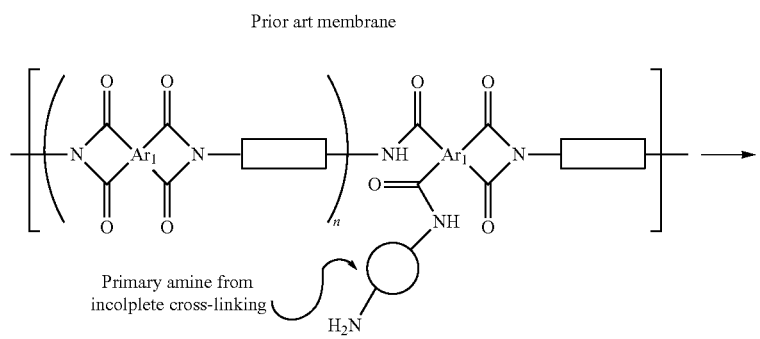

Primary amine from incolplete cross-linking

Inventive membrane

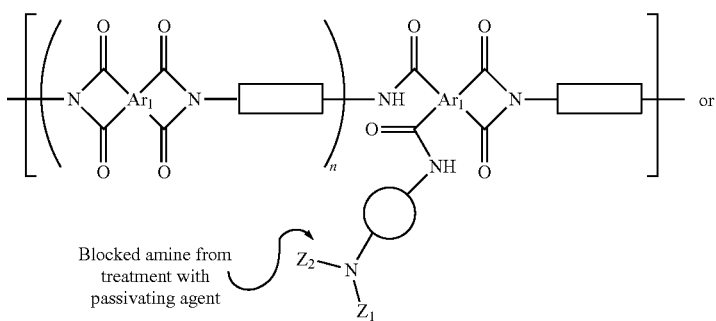

Blocked amine from treatment with passivating agent

Prior art membrane

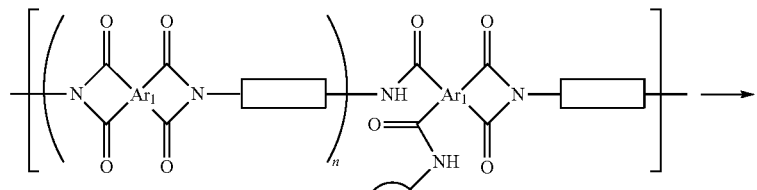

Inventive membrane

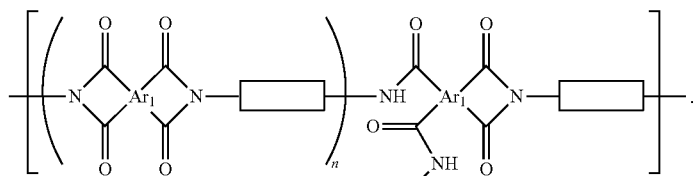

If necessary, the problem of reactive amides can be addressed by utilizing secondary amines in the cross-linking process so that less reactive tertiary amides are resent in the resulting crosslinks:

wherein $R^a$ is an optionally substituted aliphatic or optionally substituted aromatic group. The present invention encompasses polyimide OSN membrane compositions incorporating either or both of these features.

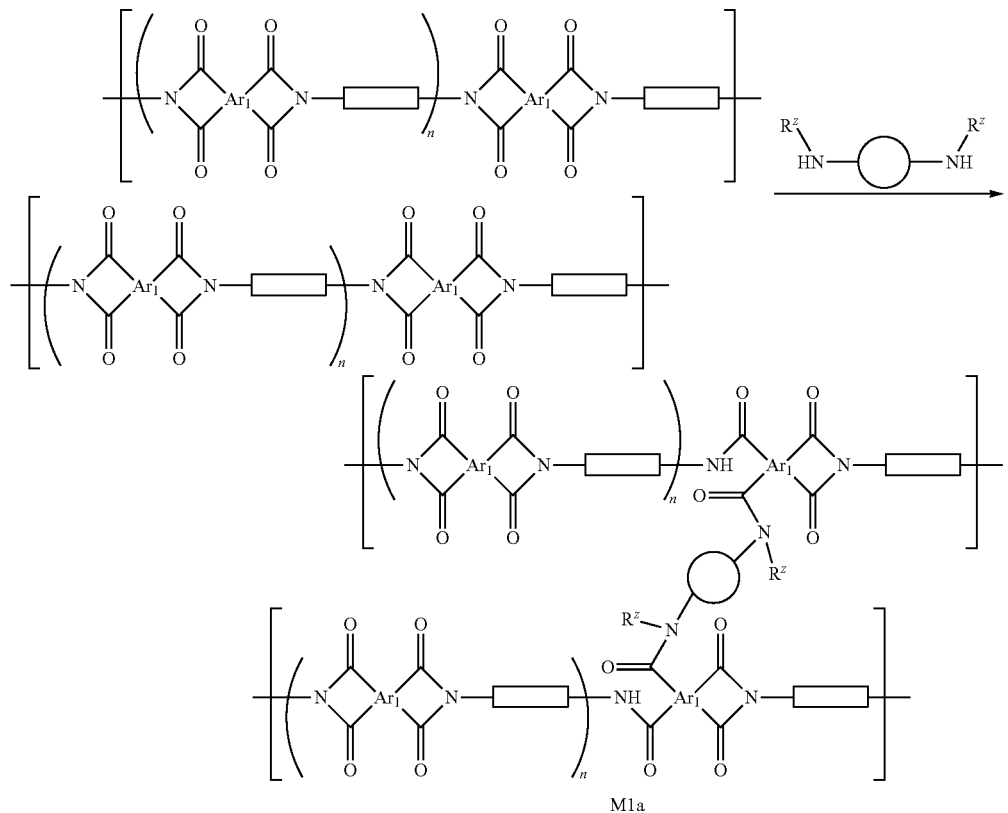

M1a

Therefore, in one aspect, the present invention encompasses OSN membrane compositions derived from the cross-linking of polyimides followed by treatment with additional reagents to passivate any residual amino groups. In certain embodiments, such membranes comprise cross-linked polyimide polymers or co-polymers having the general structure M1 and characterized in that the polymers or co-polymers further contain segments having formula M2:

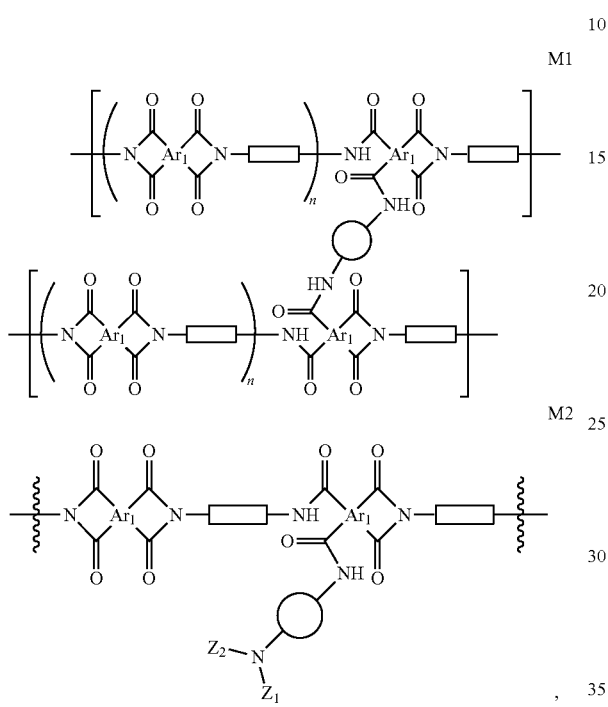

where each $Ar_1$ is a tetravalent aromatic moiety,
each

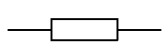

represents a bivalent linker and may be the same or different at each occurrence in the polymer or co-polymer,
each

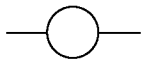

represents a bivalent linker and may be the same or different at each occurrence in the polymer or co-polymer.
n is any integer up to about 100,000
$Z_1$ is —H, aliphatic, acyl, or aryl;
$Z_2$ is selected from the group consisting of: aliphatic, aryl, acyl, —C(O)OR$^x$, —SO$_2$R$^x$, and —C(O)NHR$^x$
where $Z_1$ and $Z_2$ may optionally be taken together to form a ring, and
R$^x$ is an optionally substituted aliphatic or an optionally substituted aromatic group.
It is to be understood that such cross-linked polyimide compositions will comprise complex mixtures wherein some polymer or co-polymer chains may contain multiple cross-links and some chains may contain no cross-links.

In certain embodiments, $Ar_1$ in the formulae above is independently selected at each occurrence from the group consisting of:

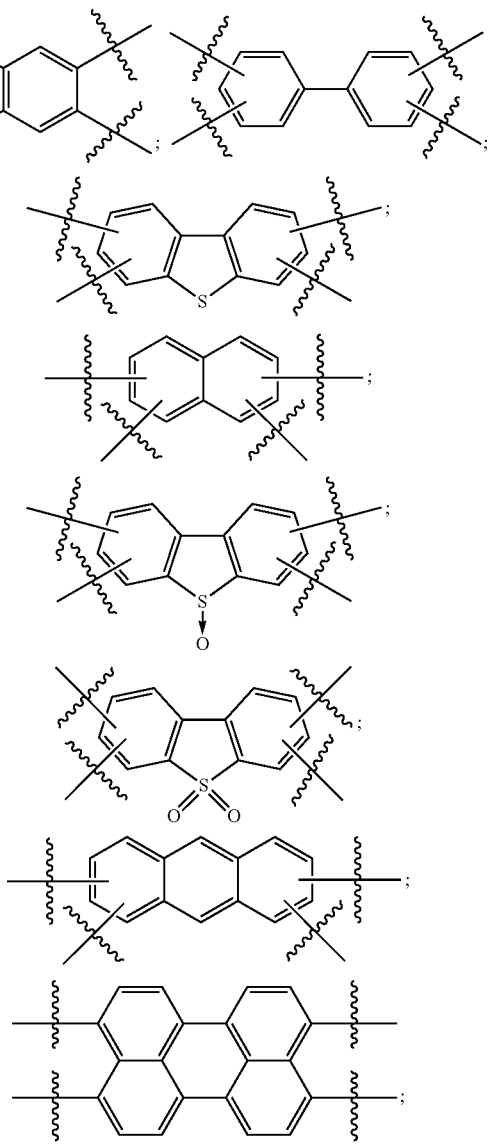

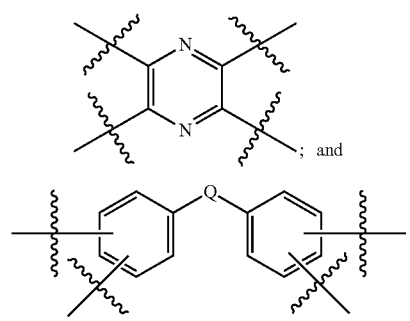

where -Q- is selected from the group consisting of:

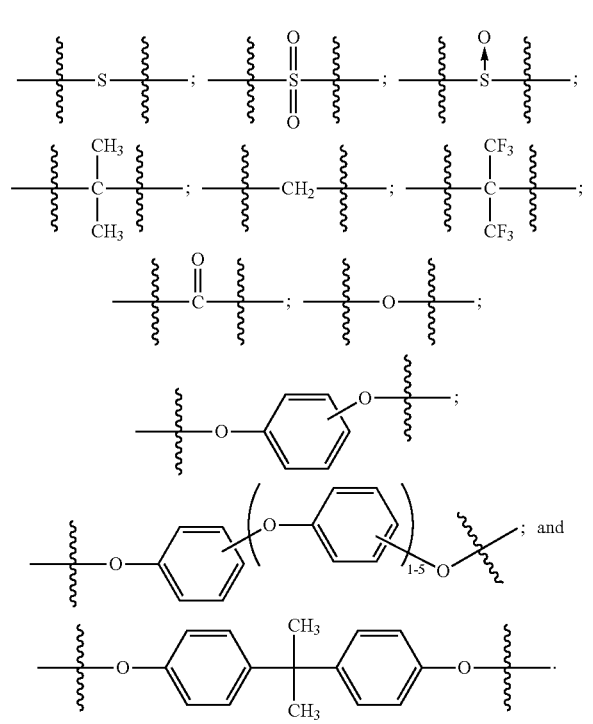

In certain embodiments, each

moiety in the formulae above is independently selected from the group consisting of:

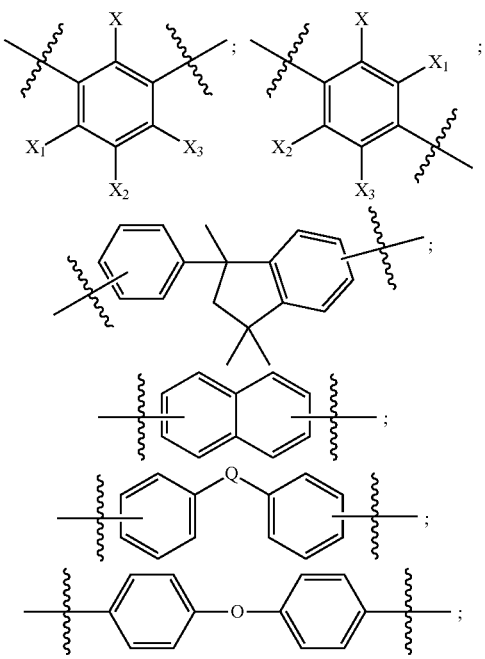

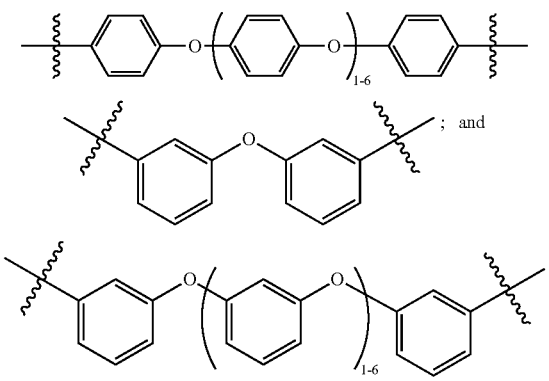

wherein Q is as defined above and in the classes and subclasses herein, and each of X, $X_1$, $X_2$ and $X_3$ are independently hydrogen, halogen, or an optionally substituted moiety selected from the group consisting of halogen, aliphatic, alkoxy, phenoxy, aryl, and phenyl.

In certain embodiments, each

moiety in the formulae above is a bivalent $C_{2-20}$ aliphatic group. In certain embodiments, each

moiety in the formulae above is selected from the group consisting of —$CH_2CH_2$—; —$CH_2CH_2CH_2$—; —$CH_2(CH_2)_2CH_2$—; —$CH_2(CH_2)_2CH_2$—; —$CH_2(CH_2)_4CH_2$—; —$CH_2(CH_2)_6CH_2$—; —$CH_2(CH_2)CH_2$—; —$CH_2(CH_2)_{10}CH_2$—; —$CH_2(CH_2)_{12}CH_2$—; —$CH_2(CH_2)_{14}CH_2$—; and —$CH_2(CH_2)_{16}CH_2$—.

In certain embodiments, each

moiety in the formulae above is a bivalent moiety derived from a diamine,

Suitable diamines include, but are not limited to: $C_{2-20}$ aliphatic diamines, ethylene diamine, propylene diamine, tetramethylene diamine, 1,6-hexamethylene diamine, 1,12-Dodecanediamine, 1,10-Decanediamine, Norbornane diamine, bis(6-aminohexyl)ether, tricyclodecane diamine, 3,4-diaminofuran, and cycloaliphatic diamines such as those having the following structures:

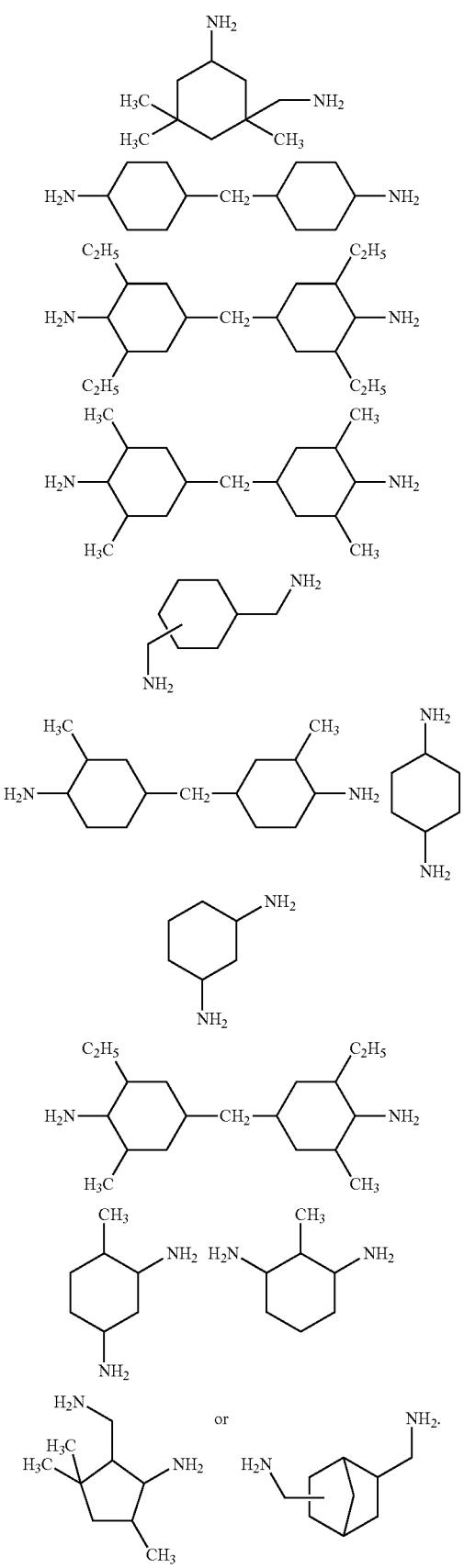

In certain embodiments, each

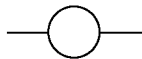

moiety in the formulae above is a bivalent aromatic group. In certain embodiments, such bivalent aromatic groups are independently selected from the group consisting of:

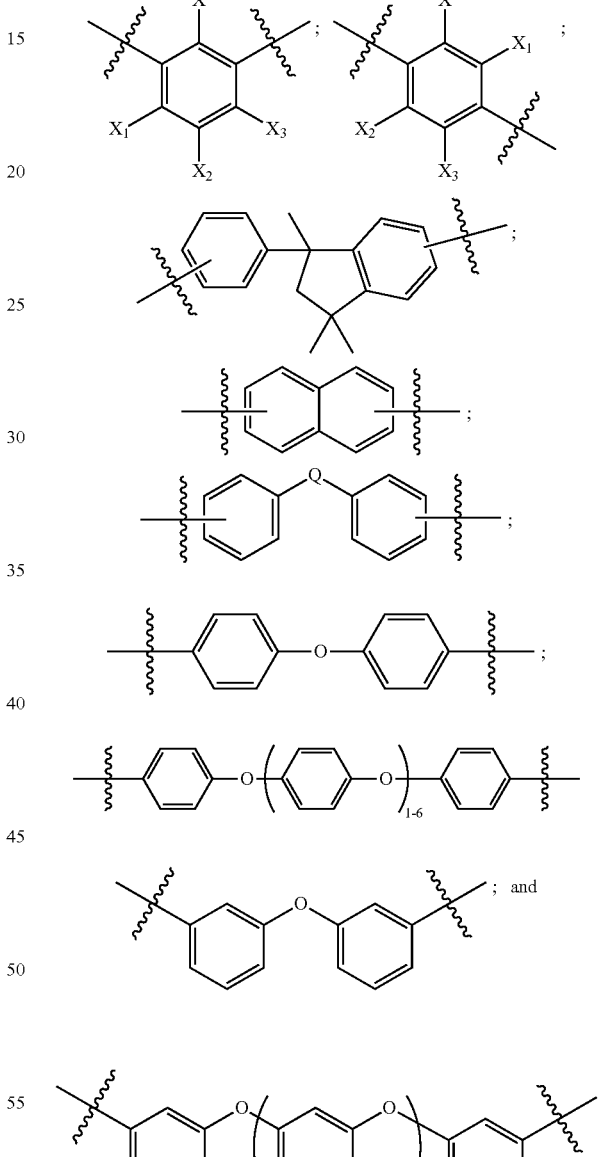

wherein each of X, $X_1$, $X_2$, $X_3$, and Q is as defined above and in the classes and subclasses herein.

In certain embodiments, the present invention encompasses cross-linked polyimide OSN membrane compositions containing segments within the polyimide polymer or co-polymer with any of formulae M2a-M2j:

M2a
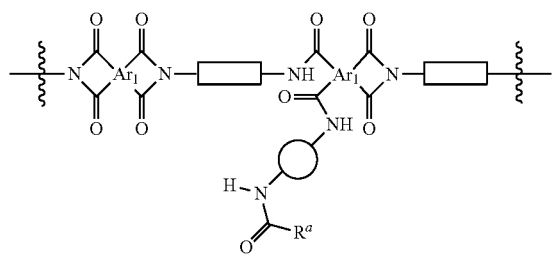
M2b
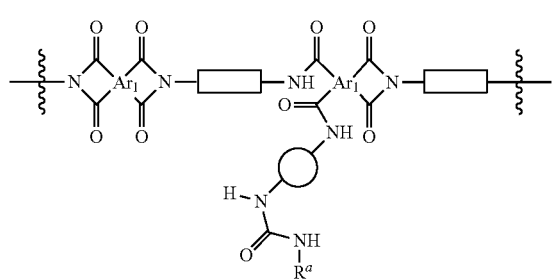
M2c
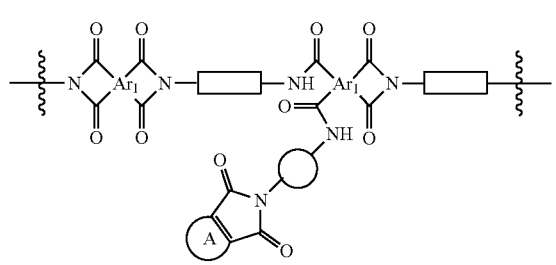
M2d
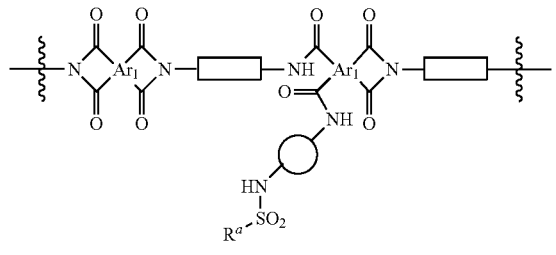
M2e
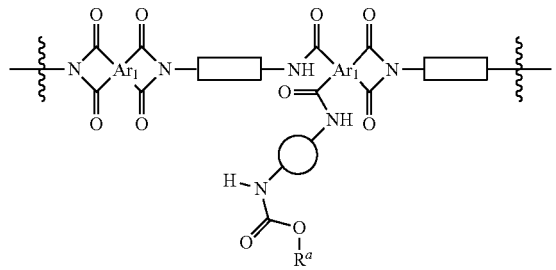
M2f
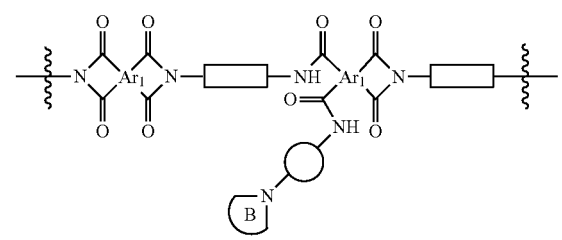
M2g
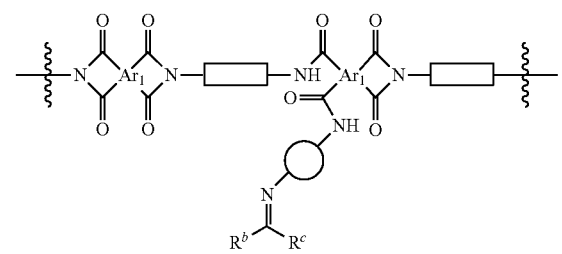
M2h
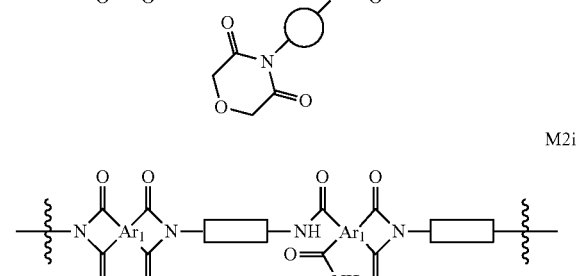
M2i
M2j
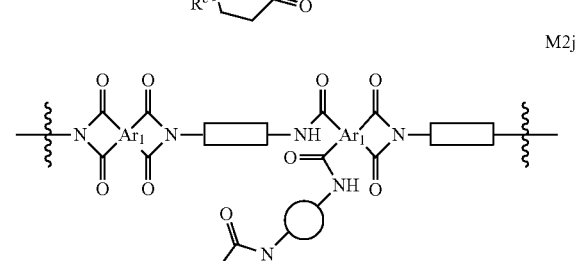
wherein,
each of Ar₁,
—◯—, and —▭—
is as defined above and in the classes and subclasses herein, R$^a$ is —H, or an optionally substituted radical selected from the group consisting of C$_{1-20}$ aliphatic, CJ-20 heteroaliphatic, 3- to 12-membered heterocyclic, and 6- to 12-membered aryl;

each of R$^b$ and R$^c$ are independently selected from the group consisting of: —H; optionally substituted C$_1$ to C$_{12}$ aliphatic; optionally substituted 3- to 14-membered carbocyclic; and optionally substituted 3- to 14 membered heterocyclic, where R$^b$ and R$^c$ may be taken together with intervening atoms to form one or more optionally substituted rings;

R$^c$ is one or more moieties independently selected from the group consisting of: —H, halogen, —OR, —NR$_2$, —SR. —CN, —SO$_2$R, —SOR, —CO$_2$R, —C(O)R, —OC(O)R, SO$_2$NR$_2$; —CNO, —NRSO$_2$R, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur, R is —H, optionally substituted aliphatic or optionally substituted aromatic; ⌇ is a single or double bond;

ring A is an optionally substituted aryl ring or an optionally substituted saturated or partially unsaturated mono- or polycyclic ring optionally containing one or more heteroatoms selected from the group consisting of nitrogen, oxygen, and sulfur; and ring B represents an optionally substituted 5- or 6-membered saturated, partially unsaturated or aromatic ring optionally containing one or more additional heteroatoms selected from the group consisting of nitrogen, oxygen, and sulfur, which may be part of a larger fused ring system.

In certain embodiments, the present invention provides cross-linked polyimide OSN membranes characterized in that they comprise moieties of formula M2a. In certain embodiments, such membranes comprise moieties selected from the group consisting of:

M2a-1
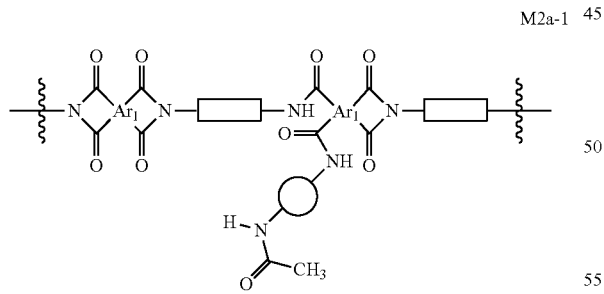

M2a-2
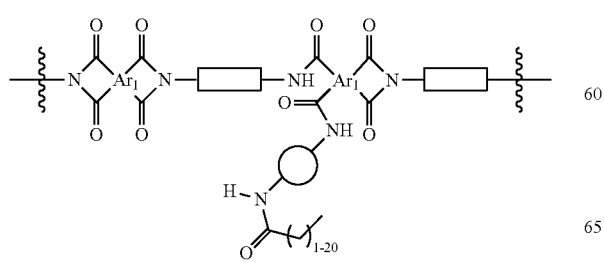

M2a-3
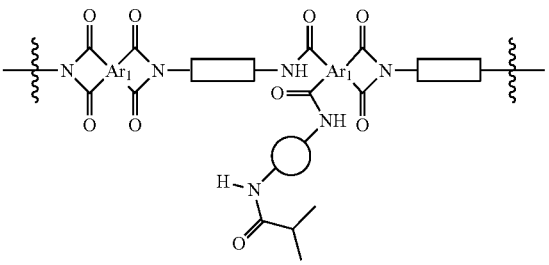

M2a-4
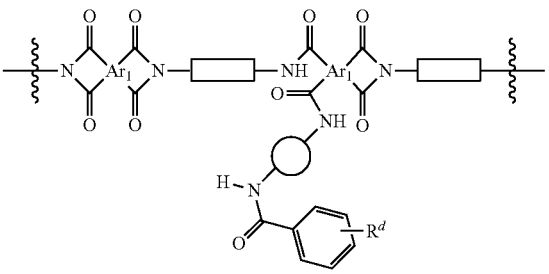

M2a-5
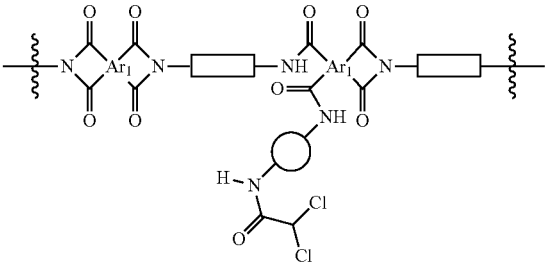

M2a-6
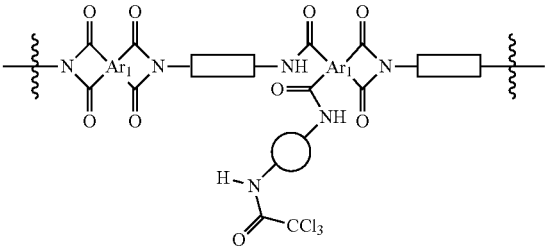

M2a-7
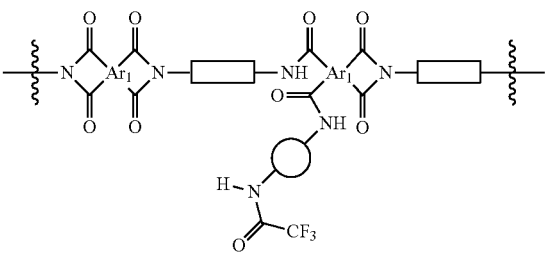

M2a-8

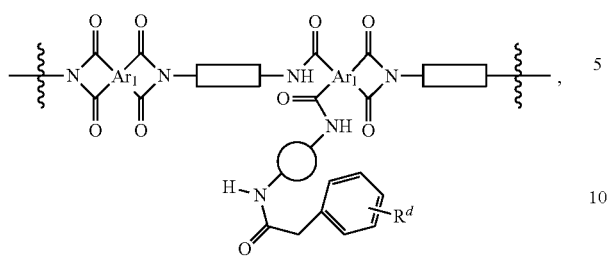

wherein each of $Ar_1$,

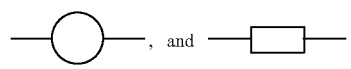

is as defined above and in the classes and subclasses herein, and $R^d$ is one or more moieties selected from the group consisting of: —H, halogen, —OR, —NR$_2$, —SR, —CN, —NO$_2$, —SO$_2$R, —SOR, —CO$_2$R, —C(O)R, —OC(O)R, SO$_2$NR$_2$; —CNO, —NRSO$_2$R, —NCO, —N$_3$, —SiR$_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur, 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur, where R is H, or optionally substituted aromatic, and where two or more $R^d$ groups may be taken together with the carbon atoms to which they are attached and any intervening atoms to form one or more optionally substituted rings optionally containing one or more heteroatoms, or where two $R^d$ groups are attached to the same carbon atom they may be taken together to form a carbonyl or an optionally substituted moiety selected from alkene, spirocycle, imine or oxime.

In certain embodiments, the present invention provides cross-linked polyimide OSN membranes characterized in that they comprise moieties of formula M2b. In certain embodiments, such membranes comprise moieties selected from the group consisting of:

M2b-1

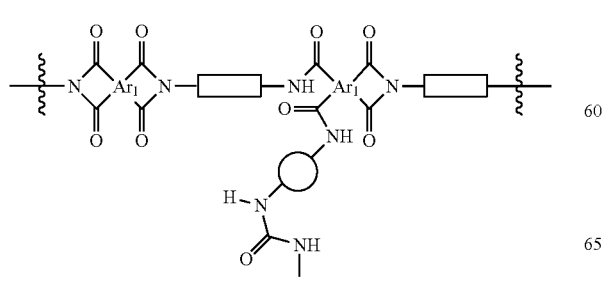

M2b-2

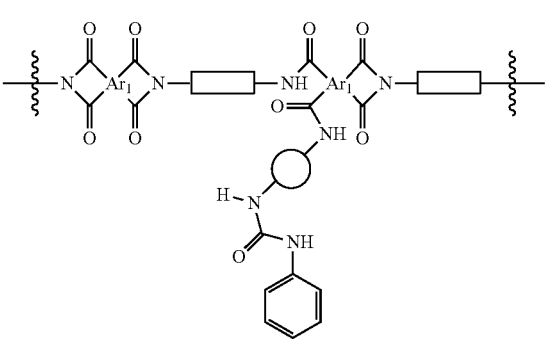

M2b-3

M2b-4

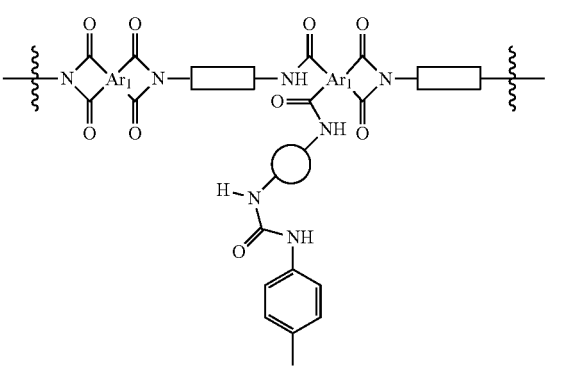

M2b-5

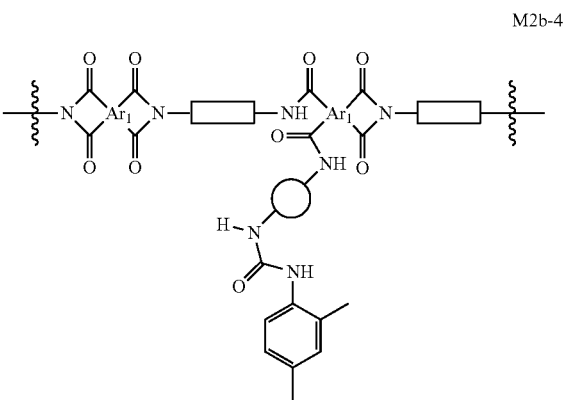

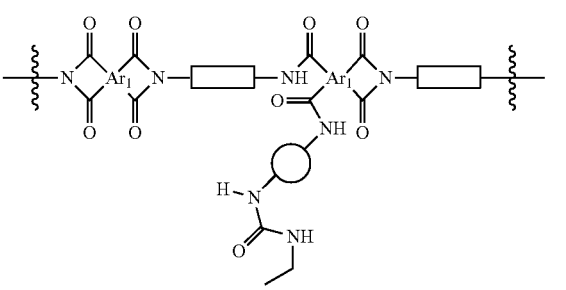

M2b-6
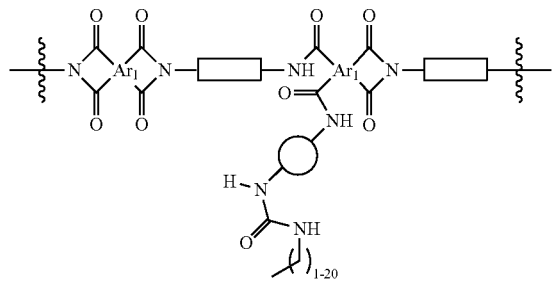
M2b-7
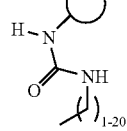
M2b-8
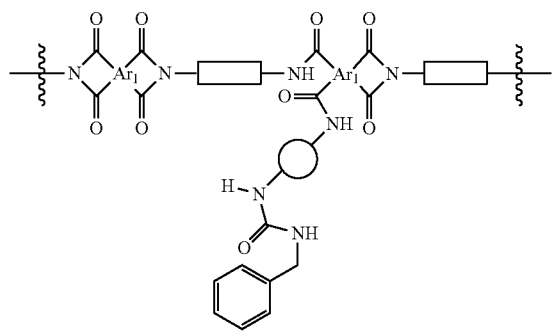
M2b-9
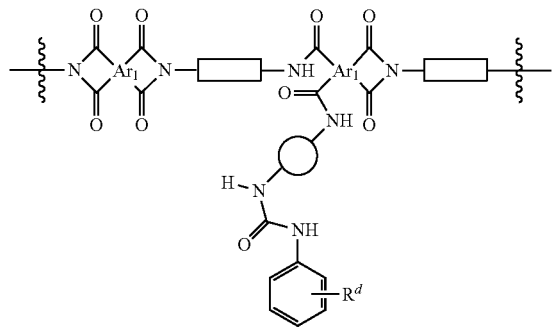
M2b-10
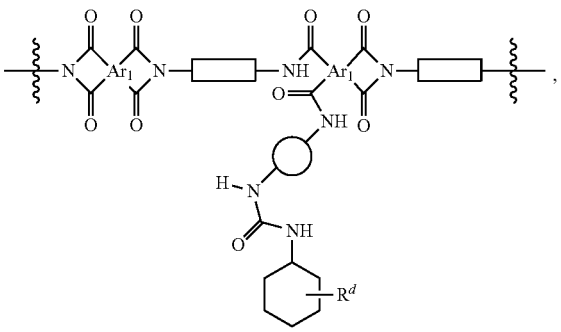
wherein each of $Ar_1$, $R^d$,
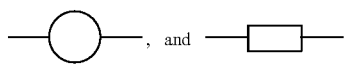
is as defined above and in the classes and subclasses herein.
In certain embodiments, the present invention provides cross-linked polyimide OSN membranes characterized in that they comprise moieties of formula M2c. In certain embodiments, such membranes comprise moieties selected from the group consisting of:
M2c-1
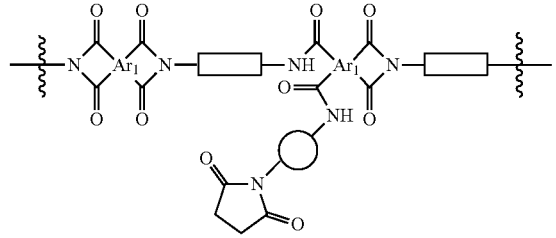
M2c-2
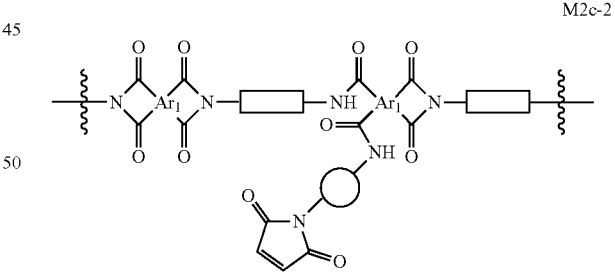
M2c-3
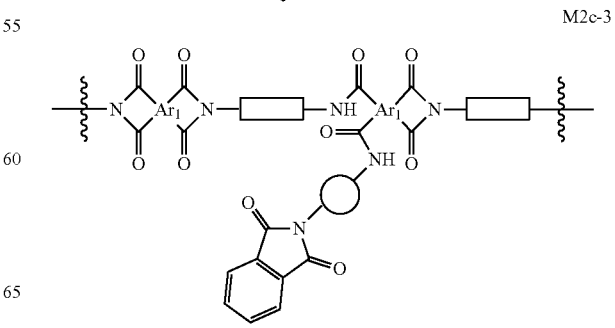

M2c-4
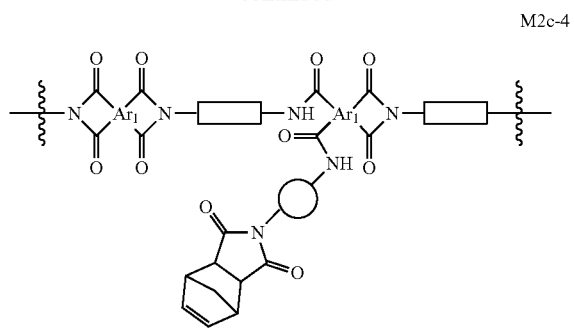

M2c-5

M2c-6

M2c-7

M2c-8 wherein each of $Ar_1$, $R^d$,

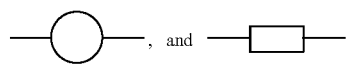, and and is as defined above and in the classes and subclasses herein.

In certain embodiments, the present invention provides cross-linked polyimide OSN membranes characterized in that they comprise moieties of formula M2d. In certain embodiments, such membranes comprise moieties selected from the group consisting of:

M2d-1
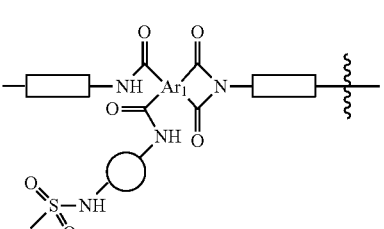

M2d-2
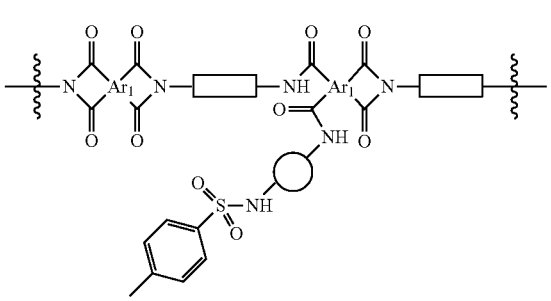

M2d-3
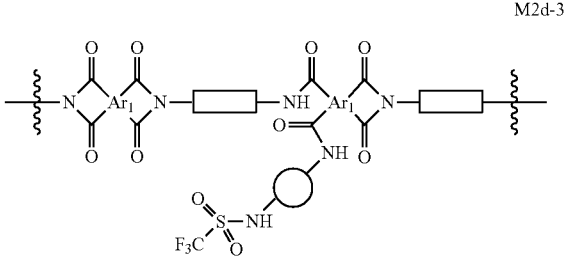

M2d-4
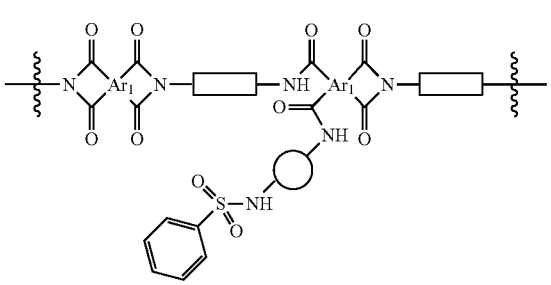

M2d-5
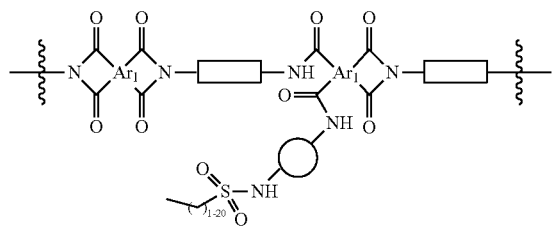

M2d-6
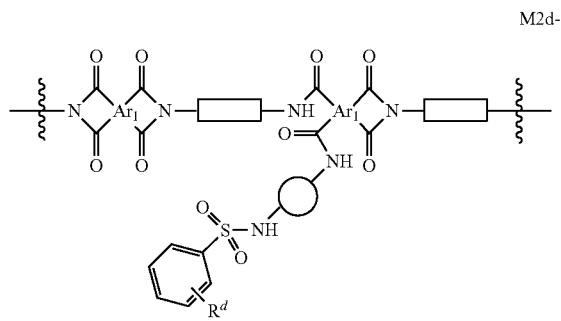

M2d-7
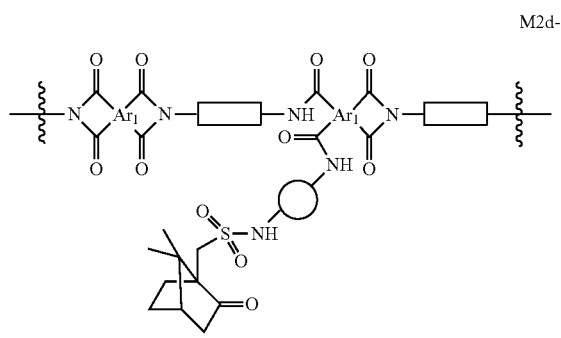

M2d-8
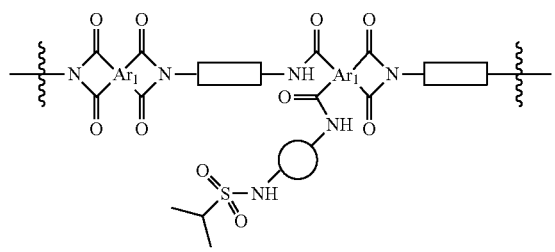

M2d-9
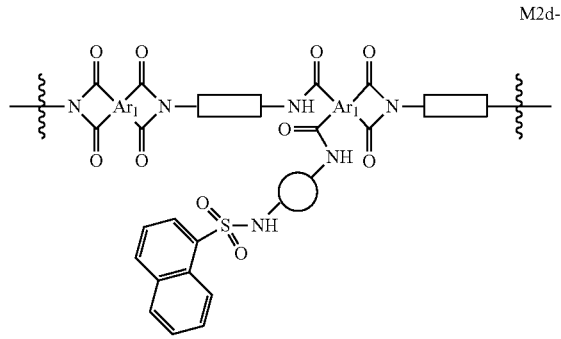

M2d-10
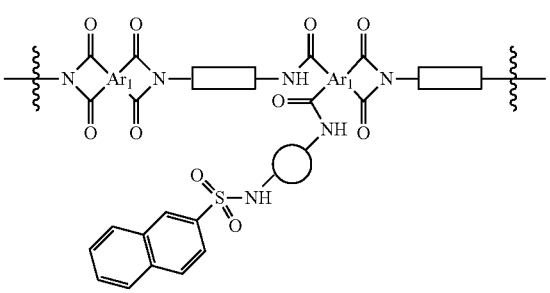

wherein each of $Ar_1$, $R^d$,

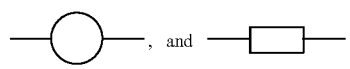, and is as defined above and in the classes and subclasses herein.

In certain embodiments, the present invention provides cross-linked polyimide OSN membranes characterized in that they comprise moieties of formula M2e. In certain embodiments, such membranes comprise moieties selected from the group consisting of:

M2e-1
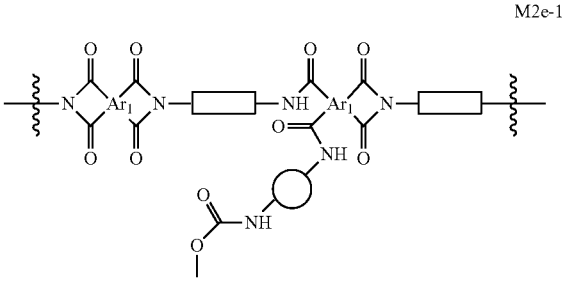

M2e-2
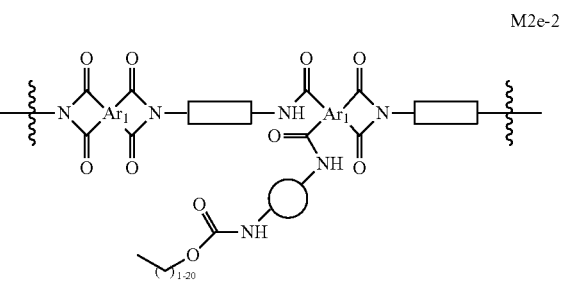

M2e-3
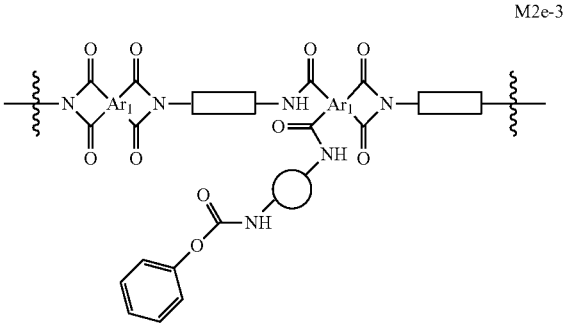

M2e-4
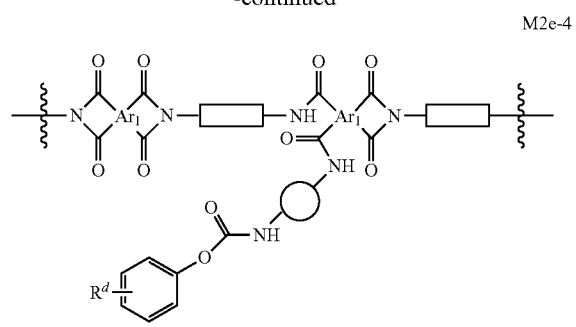

M2e-5
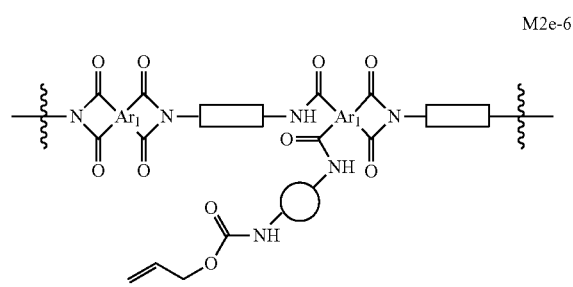

M2e-6
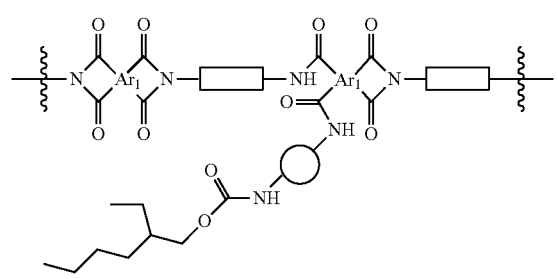

M2e-7
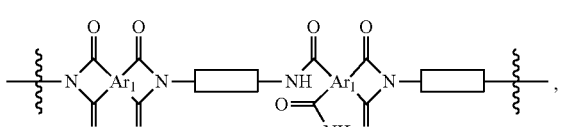

M2e-8
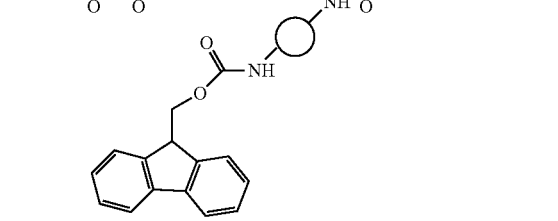

wherein each of $Ar_1$, $R^d$,

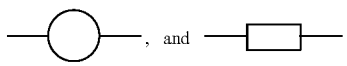, and is as defined above and in the classes and subclasses herein.

In certain embodiments, the present invention provides cross-linked polyimide OSN membranes characterized in that they comprise moieties of formula M2f. In certain embodiments, such membranes comprise moieties selected from the group consisting of:

M2f-1
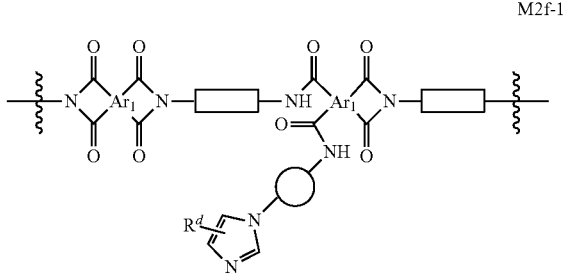

M2f-2
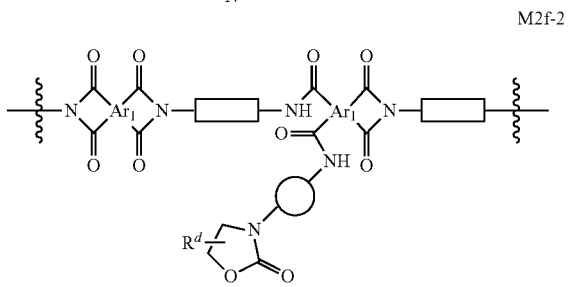

M2f-3
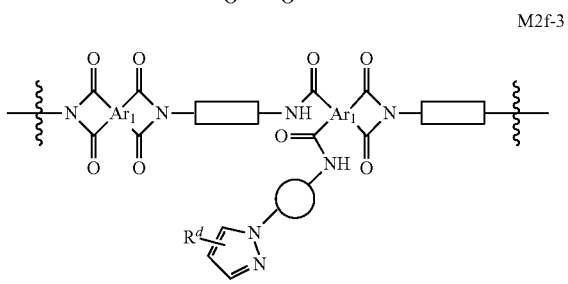

M2f-4
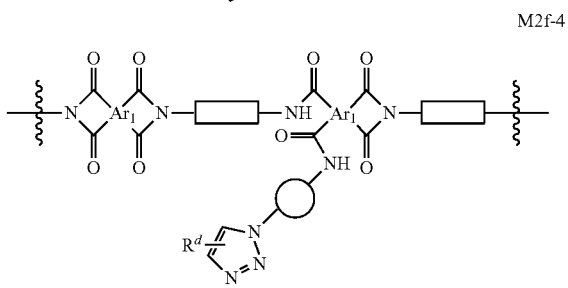

M2f-5
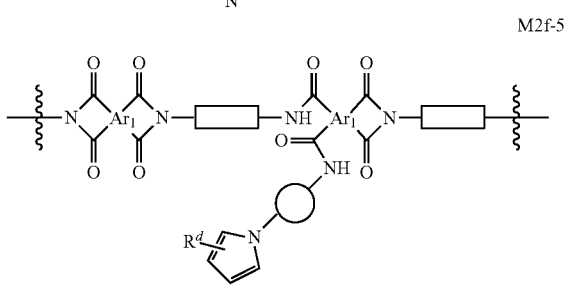

M2f-6
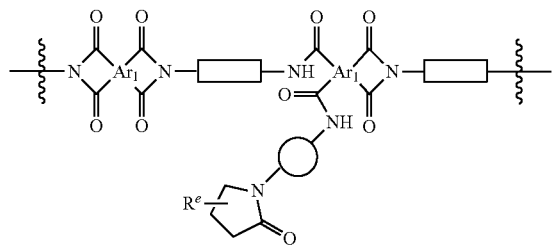

M2f-7
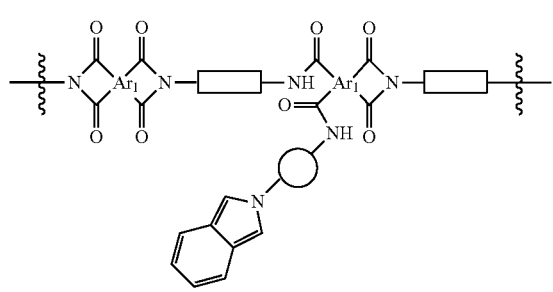

M2f-8
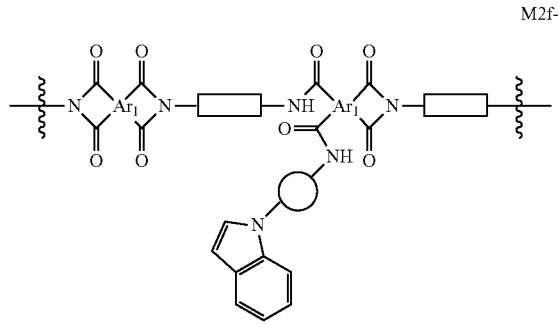

M2f-9
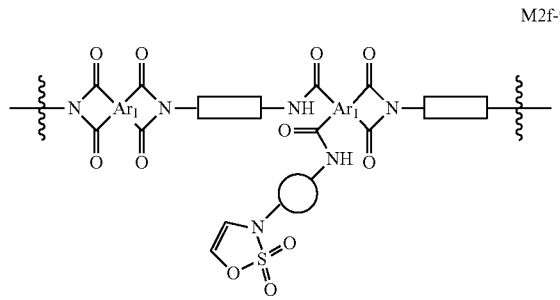

M2f-10
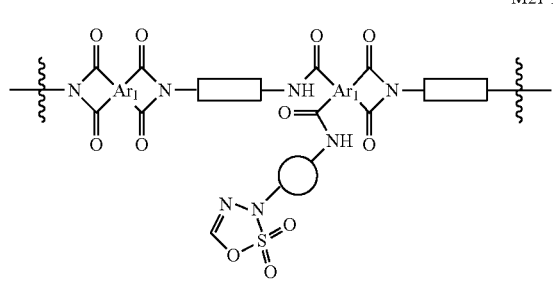

M2f-11
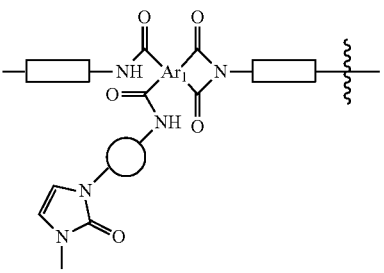

M2f-12
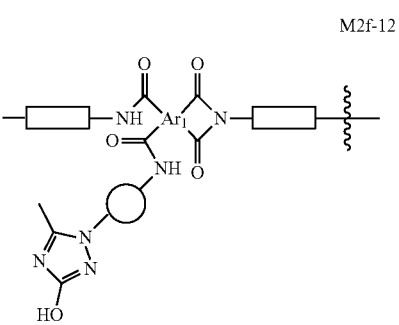

M2f-13
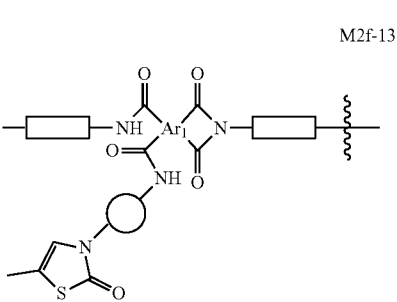

M2f-14
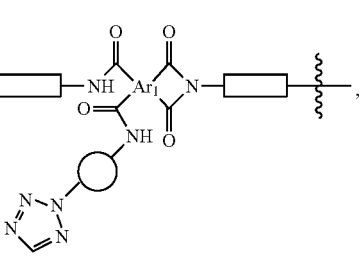

wherein each of $Ar_1$, $R^d$, $R^c$,

———◯———, and ——▭—— is as defined above and in the classes and subclasses herein.

In certain embodiments, the present invention provides cross-linked polyimide OSN membranes characterized in that they comprise moieties of formula M2g. In certain embodiments, such membranes comprise moieties selected from the group consisting of:

M2g-1
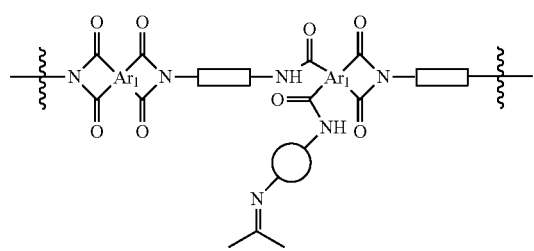

M2g-2
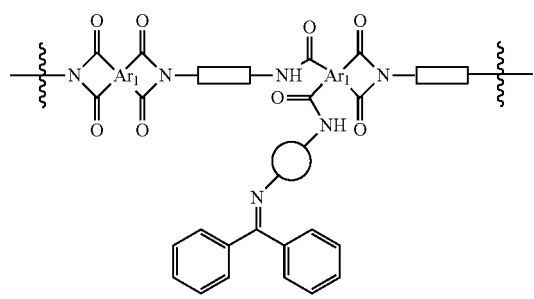

wherein each of $Ar_1$,

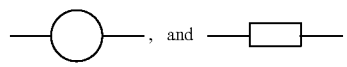

is as defined above and in the classes and subclasses herein.

In certain embodiments, the present invention provides cross-linked polyimide OSN membranes characterized in that they comprise moieties of formula M2h.

In certain embodiments, the present invention provides cross-linked polyimide OSN membranes characterized in that they comprise moieties of formula M2i.

In certain embodiments, the present invention provides cross-linked polyimide OSN membranes characterized in that they comprise moieties of formula M2j. In certain embodiments, such membranes comprise moieties selected from the group consisting of:

M2j-1
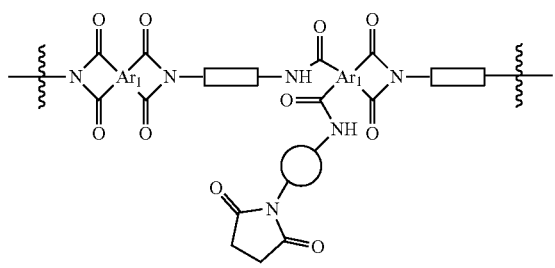

M2j-2
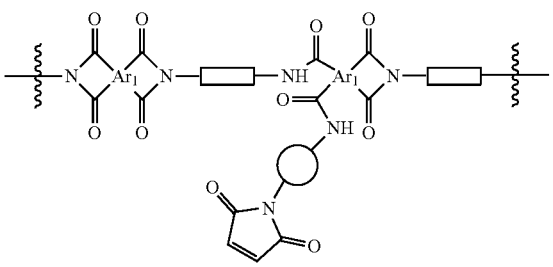

M2j-3
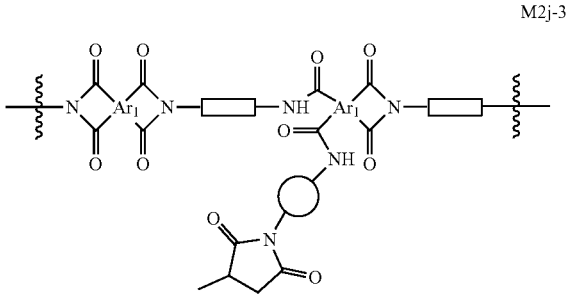

M2j-4
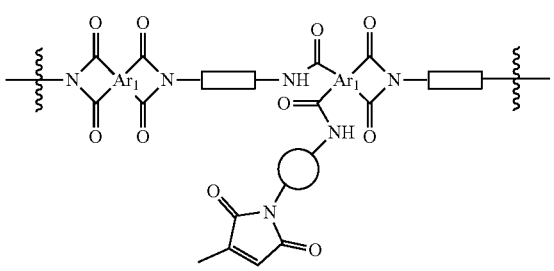

M2j-5
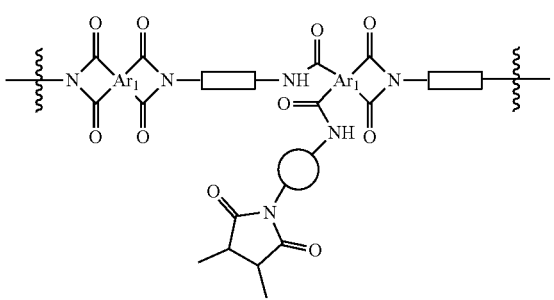

M2j-6
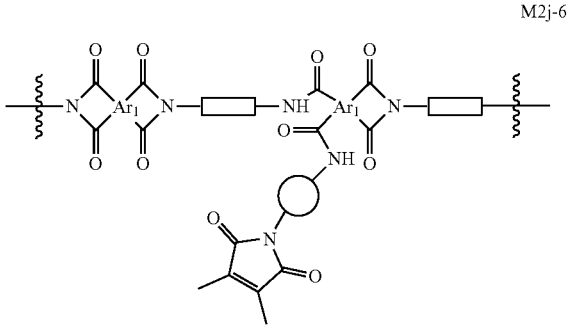

-continued

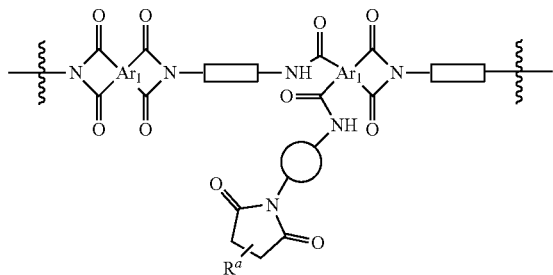
M2j-7

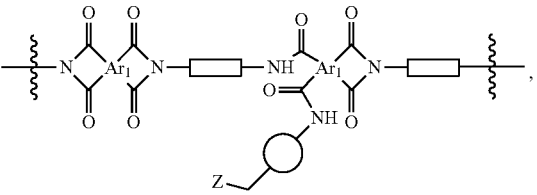
M3 wherein each of Ar$_1$,

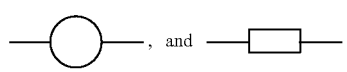

is as defined above and in the classes and subclasses herein, and Z is a functional group that does not contain a nitrogen atom.

In certain embodiments, the present invention encompasses cross-linked polyimide OSN membrane compositions containing segments within the polyimide polymer or co-polymer with any of formulae M3a or M3b:

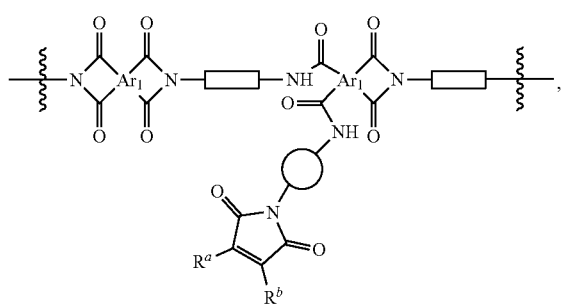
M2j-8

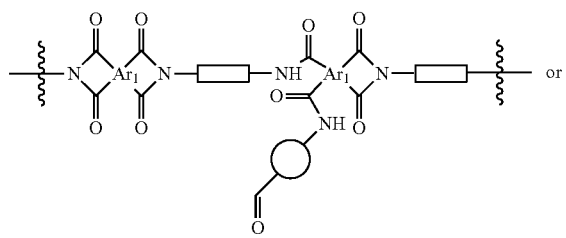
M3a

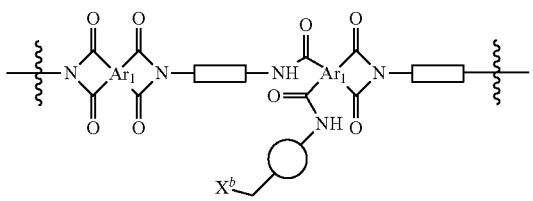
M3b wherein each of R$^a$, R$^b$, Ar$_1$,

is as defined above and in the classes and subclasses herein.

In another aspect, the present invention encompasses OSN membrane compositions derived from the cross-linking of polyimides followed by treatment to cleave any residual amino groups. In certain embodiments, such membranes comprise cross-linked polyimide polymers or co-polymers having the general structure M1 and characterized in that the polymers or co-polymers further contain segments having formula M3:

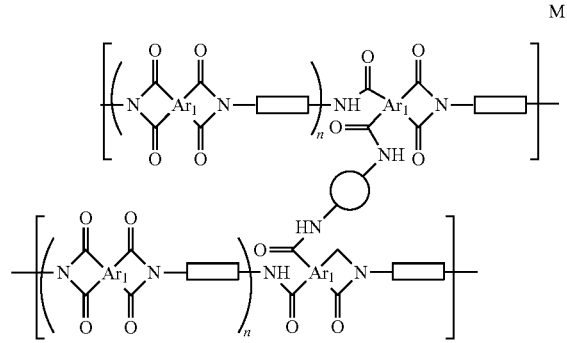
M1 wherein
X$^b$ is Cl, Br or I.

In certain embodiments, polyimide-based OSN membranes of the present invention are characterized in that they contain very few or no free amine functional groups. Such amine functional groups can arise from incomplete cross-linking procedures as just described, or they can be present in the polyimides prior to cross-linking.

In certain embodiments, for any of formulae M2a-1 through M2j-8 and M3, M3a and M3b, the moiety

is an aliphatic group. In certain embodiments, for any of formulae M2a-1 through M2j-8 and M3, M3a and M3b, the moiety

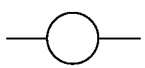

is —CH₂CH₂—. In certain embodiments, for any of formulae M2a-1 through M2j-8 and M3, M3a and M3b, the moiety

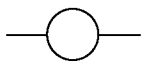

is —CH₂CH₂—. In certain embodiments, for any of formulae M2a-1 through M2j-8 and M3, M3a and M3b, the moiety

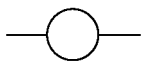

is —CH₂CH₂CH₂—. In certain embodiments, for any of formulae M2a-1 through M2j-8 and M3, M3a and M3b, the moiety

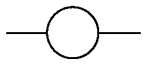

is —CH₂(CH₂)₂CH₂. In certain embodiments, for any of formulae M2a-1 through M2j-8, and M3. M3a and M3b, the moiety

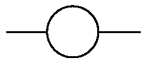

is —CH₂(CH₂)₄CH₂—.

In certain embodiments, for any of formulae M2a-1 through M2j-8 and M3, M3a and M3b, the moiety

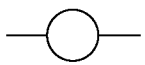

is an aromatic group. In certain embodiments, for any of formulae M2a-1 through M2j-8 and M3, M3a and M3b, the moiety

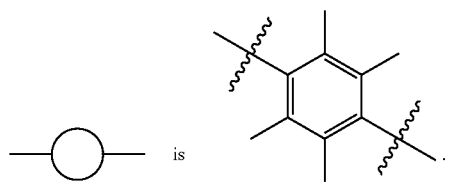

In certain embodiments, for any of formulae M2a-1 through M2j-8 and M3, M3a and M3b, the moiety

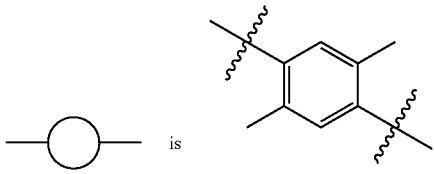

In certain embodiments, for any of formulae M2a-1 through M2j-8 and M3, M3a and M3b, the moiety

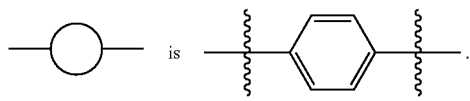

In certain embodiments, for any of formulae M2a-1 through M2j-8 and M3, M3a and M3b, the moiety

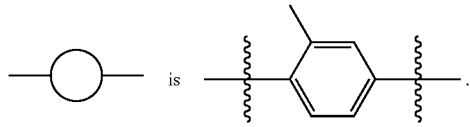

In certain embodiments, for any of formulae M2a-1 through M2j-8 and M3, M3a and M3b, the moiety

In certain embodiments, for any of formulae M2a-1 through M2j-8 and M3, M3a and M3b, the moiety

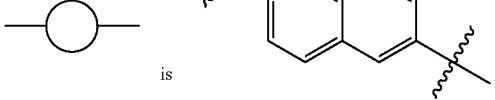

In certain embodiment any of formulae M2a-1 through M2j-8 and M3, M3a and M3b, Ar₁ has the formula

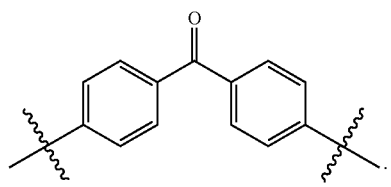 [SMILES: *c1ccc(C(=O)c2ccc(*)cc2)cc1]

In certain embodiments, for any of formulae M2a-1 through M2j-8 and M3, M3a and M3b, the moiety has the formula

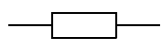

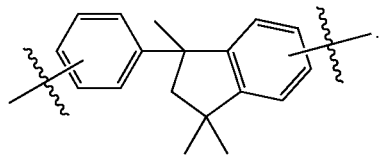

In certain embodiments, for any of formulae M2a-1 through M2j-8 and M3, M3a and M3b, the moiety

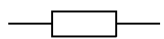

as the formula

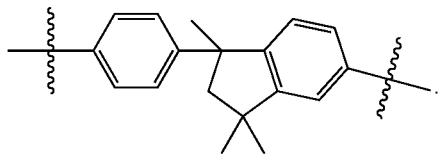 [SMILES: *c1ccc(C2(C)CC(C)(C)c3cc(*)ccc32)cc1]

In certain embodiments, for any of formulae M2a-1 through M2j-8 and M3, M3a and M3b, Ar₁ has the formula

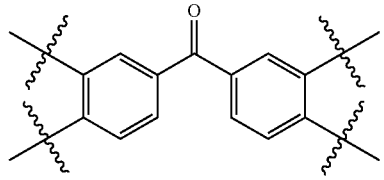 [SMILES: *c1ccc(C(=O)c2ccc(*)c(*)c2)cc1*]

and the moiety

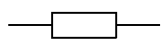

has the formula

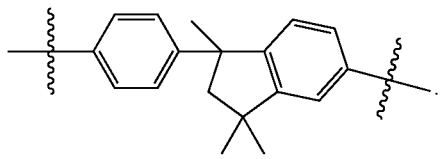 [SMILES: *c1ccc(C2(C)CC(C)(C)c3cc(*)ccc32)cc1]

In certain embodiments, for any of formulae M2a-1 through M2j-8 and M3, M3a and M3b, Ar₁ has the formula

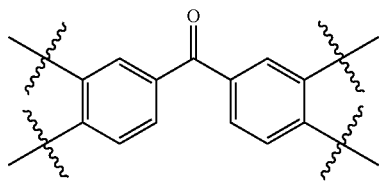 [SMILES: *c1ccc(C(=O)c2ccc(*)c(*)c2)cc1*]

and the moiety

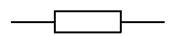

has the formula

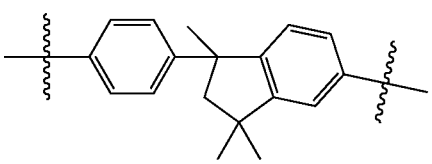

In certain embodiments, the polyimide-based OSN membranes of the present invention are characterized in that they contain less than about 100 μmol of free amine per gram of polyimide. In certain embodiments, the polyimide-based OSN membranes of the present invention are characterized in that they contain less than 75 μmol, less than 50 μmol, less than 40 μmol, less than 30 μmol, less than 25 μmol, less than 20 μmol, less than 15 μmol, less than 10 μmol, less than 5 μmol, or less than 1 μmol of free amine per gram of polyimide. In certain embodiments, the polyimide-based OSN membranes of the present invention are characterized in that they contain less than 500 nmol of free amine per gram of polyimide. In certain embodiments, the polyimide-based OSN membranes of the present invention are characterized in that they contain less than 400 nmol, less than 300 nmol, less than 250 nmol, less than 200 nmol, less than 150 nmol, less than 100 nmol, less than 50 nmol, less than 40 nmol, less than 30 nmol, less than 20 nmol, less than 10 nmol, less than 5 nmol, or less than 1 nmol of free amine per gram of polyimide.

In certain embodiments, the polyimide-based OSN membranes of the present invention are characterized in that they are essentially free of detectable free amine. In certain embodiments, they are essentially free of detectable free amine as determined by colorimetric analysis: for example by optical absorption or fluorescence detection after reaction with a derivitizing agent. In certain embodiments, such derivitizing agents include ninhydrin, 1,8-Diazafluoren-9-one (DFO), 1,2-Indanedione, 5-methylthioninhydrin (5-MTN), or similar reagents. In certain embodiments, the present invention provides polyimide-based OSN membranes characterized in that they give a negative ninhydrin test. In certain embodiments, the present invention provides polyimide-based OSN membranes characterized in that they give a negative DFO test. In certain embodiments, the present invention provides polyimide-based OSN membranes characterized in that they give a negative 5-MTN test. In certain embodiments, the present invention provides polyimide-based OSN membranes characterized in that they give a negative test with 1,2-indanedione.

In certain embodiments, the polyimide-based OSN membranes of the present invention are characterized in that they are essentially free of detectable free amine by spectrometric analysis.

In certain embodiments, provided is a nanofiltration membrane comprising a co-polymer, the co-polymer comprising a monomer of Formula M1 and one or more monomers of Formulae M1a, M2 and M3:

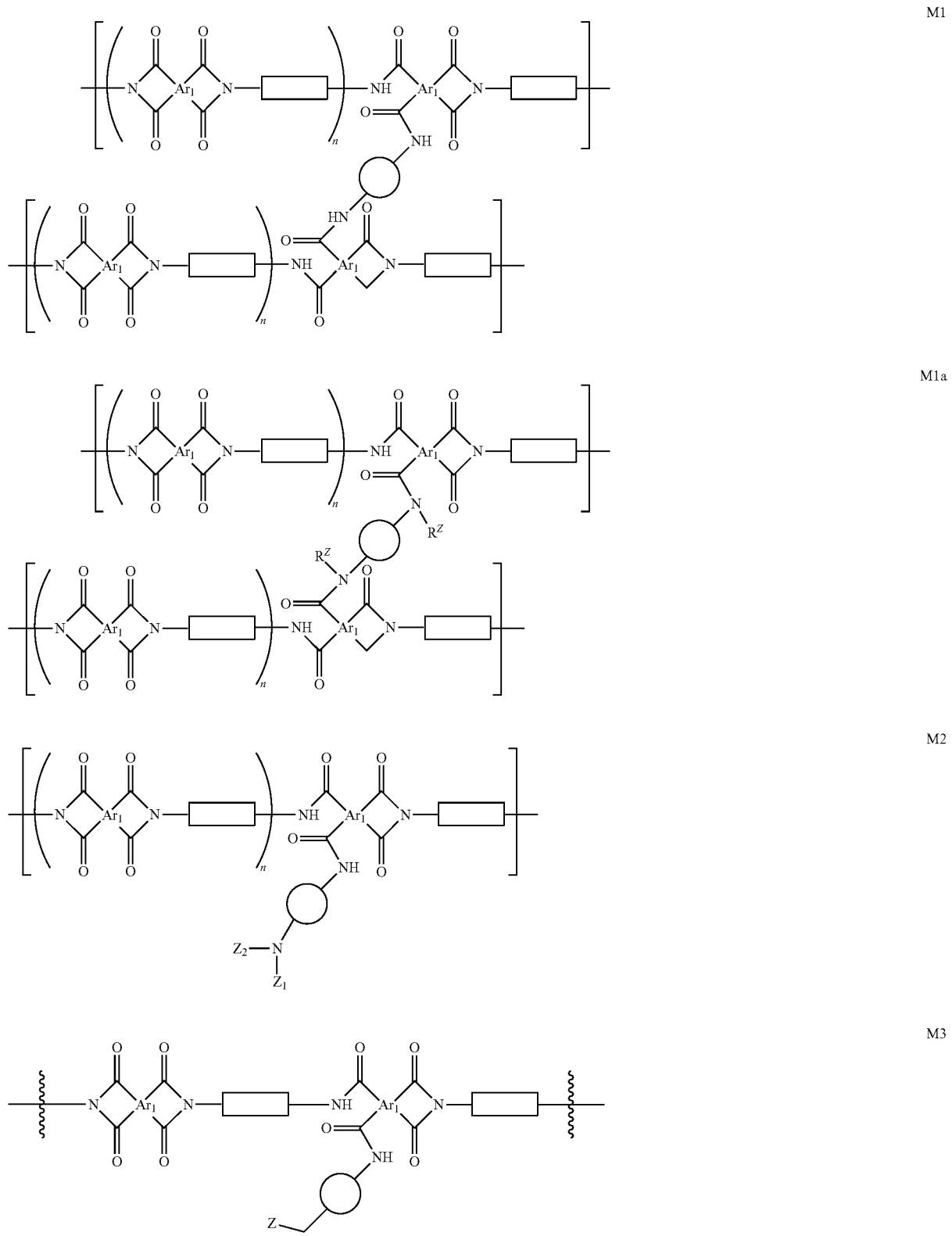

wherein:
each $Ar_1$ is a tetravalent aromatic moiety;
each

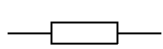

represents a bivalent linker and may be the same or different at each occurrence in the co-polymer,
each

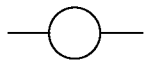

represents a bivalent linker and may be the same or different at each occurrence in the co-polymer;
n is any integer up to about 100,000;
Z is a functional group that does not contain a nitrogen atom;
$Z_1$ is —H, aliphatic, acyl or aryl;
$Z_2$ is selected from the group consisting of: aliphatic, aryl, acyl, —C(O)OR$^x$, —SO$_2$R$^x$ and —C(O)NHR$^x$;
where $Z_1$ and $Z_2$ may optionally be taken together to form a ring,
$R^z$ is an optionally substituted aliphatic or optionally substituted aromatic group; and
$R^x$ is an optionally substituted aliphatic or optionally substituted aromatic group.

In certain embodiments, provided is a nanofiltration membrane comprising a co-polymer, the co-polymer comprising the monomer of Formula M1 and the monomer of Formula M1a. In certain embodiments, provided is a nanofiltration membrane comprising a co-polymer, the co-polymer comprising the monomer of Formula M1 and the monomer of Formula M2. In certain embodiments, provided is a nanofiltration membrane comprising a co-polymer, the co-polymer comprising the monomer of Formula M1 and the monomer of Formula M3.

In certain embodiments of the nanofiltration membrane, the co-polymer comprises a monomer of Formulae M2a to M2j:

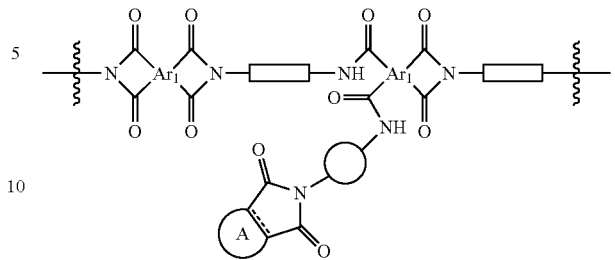

M2c

M2d

M2e

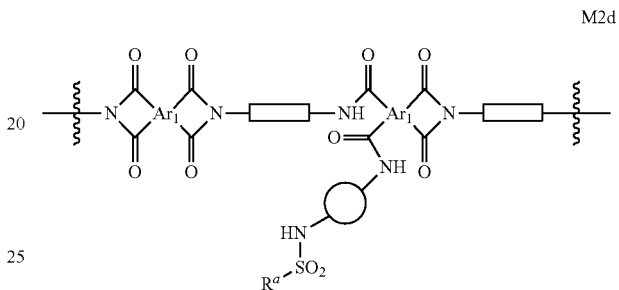

M2a

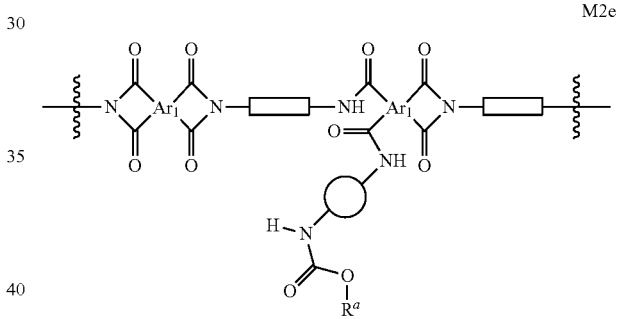

M2f

M2b

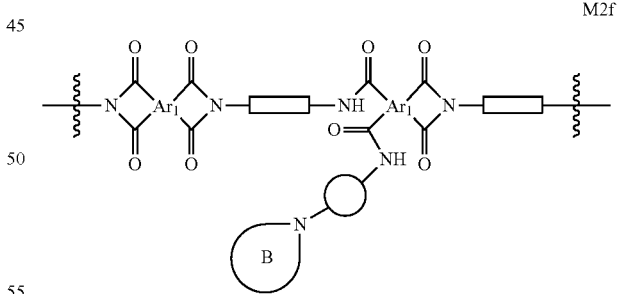

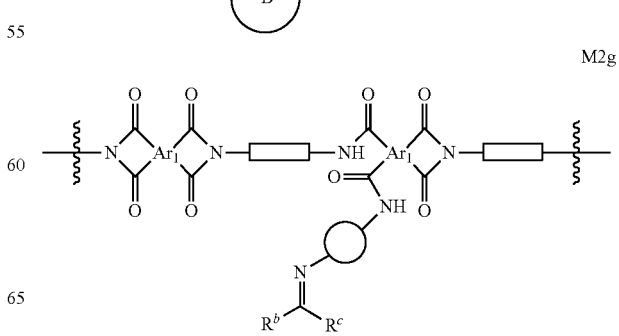

M2g

-continued

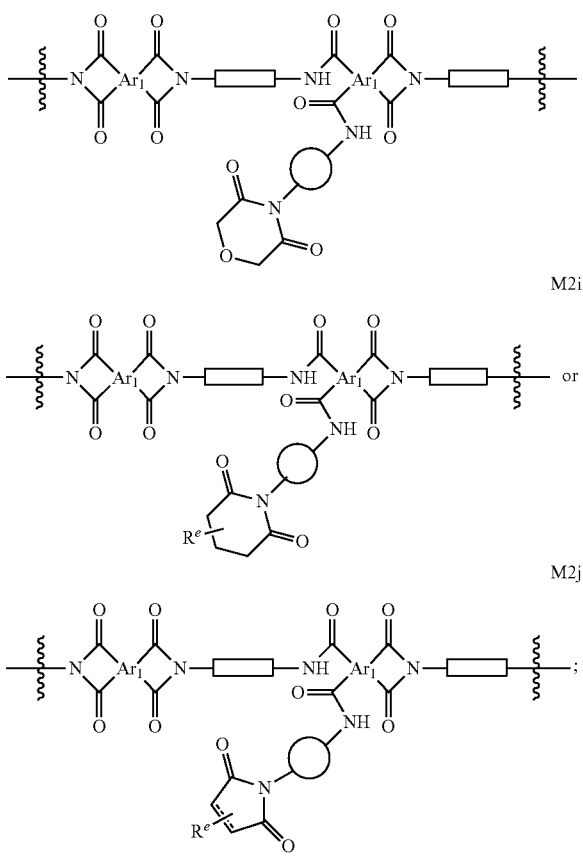

wherein:
- $R^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl;
- each of $R^b$ and $R^c$ are independently selected from the group consisting of: —H; optionally substituted $C_1$ to $C_{12}$ aliphatic; optionally substituted 3- to 14-membered carbocyclic; and optionally substituted 3- to 14 membered heterocyclic, where $R^b$ and $R^c$ may be taken together with intervening atoms to form one or more optionally substituted rings;
- $R^e$ is one or more moieties selected from the group consisting of: —H, halogen, —OR, —NR$_2$, —SR, —CN, —SO$_2$R, —SOR, —CO$_2$R, —C(O)R, —OC(O)R, SO$_2$NR$_2$; —CNO, —NRSO$_2$R, —N$_3$, —SiR$_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur, 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur,
- R is H, optionally substituted aliphatic or optionally substituted aromatic; ⁓ is a single or double bond;
- ring A is an optionally substituted aryl ring or an optionally substituted saturated or partially unsaturated mono- or polycyclic ring optionally containing one or more heteroatoms selected from the group consisting of nitrogen, oxygen, and sulfur, and
- ring B represents an optionally substituted 5- or 6-membered saturated, partially unsaturated or aromatic ring optionally containing one or more additional heteroatoms, selected from the group consisting of nitrogen, oxygen, and sulfur, which may be part of a larger fused ring system.

In certain embodiments, provided is a nanofiltration membrane comprising a co-polymer, the co-polymer comprising the monomer of Formula M1 and the monomer of Formula M2a. In certain embodiments, provided is a nanofiltration membrane comprising a co-polymer, the co-polymer comprising the monomer of Formula M1 and the monomer of Formula M2b. In certain embodiments, provided is a nanofiltration membrane comprising a co-polymer, the co-polymer comprising the monomer of Formula M1 and the monomer of Formula M2c. In certain embodiments, provided is a nanofiltration membrane comprising a co-polymer, the co-polymer comprising the monomer of Formula M1 and the monomer of Formula M2d. In certain embodiments, provided is a nanofiltration membrane comprising a co-polymer, the co-polymer comprising the monomer of Formula M1 and the monomer of Formula M2e. In certain embodiments, provided is a nanofiltration membrane comprising a co-polymer, the co-polymer comprising the monomer of Formula M1 and the monomer of Formula M2f. In certain embodiments, provided is a nanofiltration membrane comprising a co-polymer, the co-polymer comprising the monomer of Formula M1 and the monomer of Formula M2g. In certain embodiments, provided is a nanofiltration membrane comprising a co-polymer, the co-polymer comprising the monomer of Formula M1 and the monomer of Formula M2h. In certain embodiments, provided is a nanofiltration membrane comprising a co-polymer, the co-polymer comprising the monomer of Formula M1 and the monomer of Formula M2i. In certain embodiments, provided is a nanofiltration membrane comprising a co-polymer, the co-polymer comprising the monomer of Formula M and the monomer of Formula M2j.

In certain embodiments of the nanofiltration membrane, the co-polymer comprises a monomer of Formulae M3a or M3b:

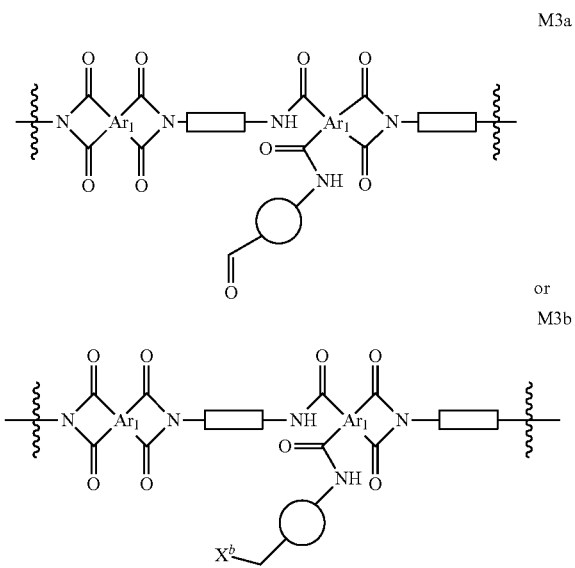

wherein $X^b$ is Cl, Br or I.

In certain embodiments of the nanofiltration membrane, each $Ar_1$ is independently selected from the group consisting of:

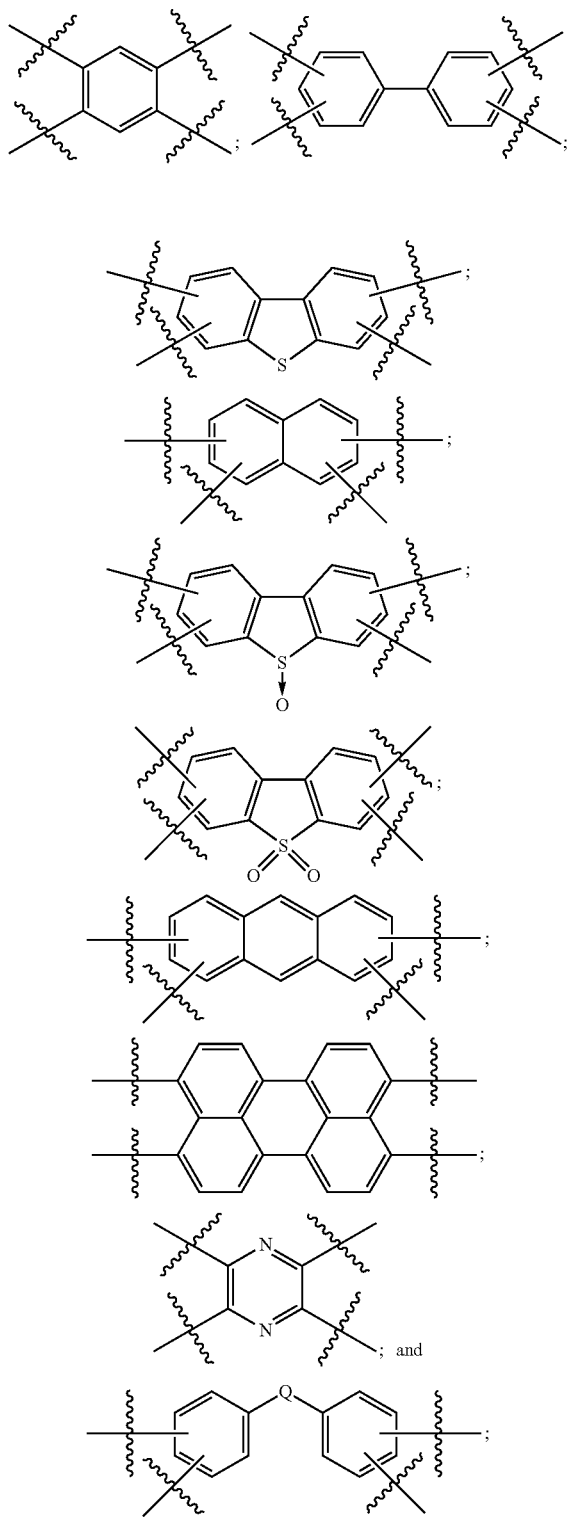

Q is selected from the group consisting of:

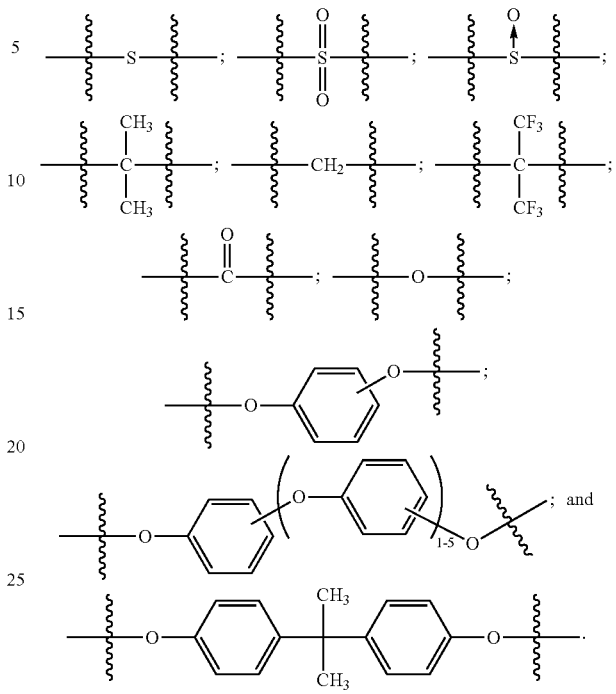

In certain embodiments, provided is a nanofiltration membrane comprising a co-polymer, the co-polymer comprising the monomer of Formula M1 and the monomer of Formula M3a. In certain embodiments, provided is a nanofiltration membrane comprising a co-polymer, the co-polymer comprising the monomer of Formula M1 and the monomer of Formula M3b.

In certain embodiments of the nanofiltration membrane, each

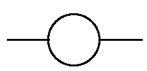

is independently a bivalent $C_{2-20}$ aliphatic group, bivalent aromatic group, or derives from a bivalent diamine group

In certain embodiments of the nanofiltration membrane, each

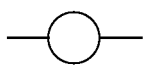

is —CH$_2$CH$_2$—; —CH$_2$CH$_2$CH$_2$—, —CH$_2$(CH$_2$)$_2$CH$_2$—; —CH$_2$(CH$_2$)$_8$CH$_2$—; —CH$_2$(CH$_2$)$_4$CH$_2$—; —CH$_2$(CH$_2$)$_6$CH$_2$—; —CH$_2$CH$_2$)$_9$CH$_2$—; —CH$_2$(CH$_2$)$_1$CH$_2$—; —CH$_2$(CH$_2$)$_{12}$CH$_2$—; —CH$_2$(CH$_2$)$_{14}$CH$_2$—; or —CH$_2$(CH$_2$)$_{16}$CH$_2$—.

In certain embodiments of the nanofiltration membrane, each is

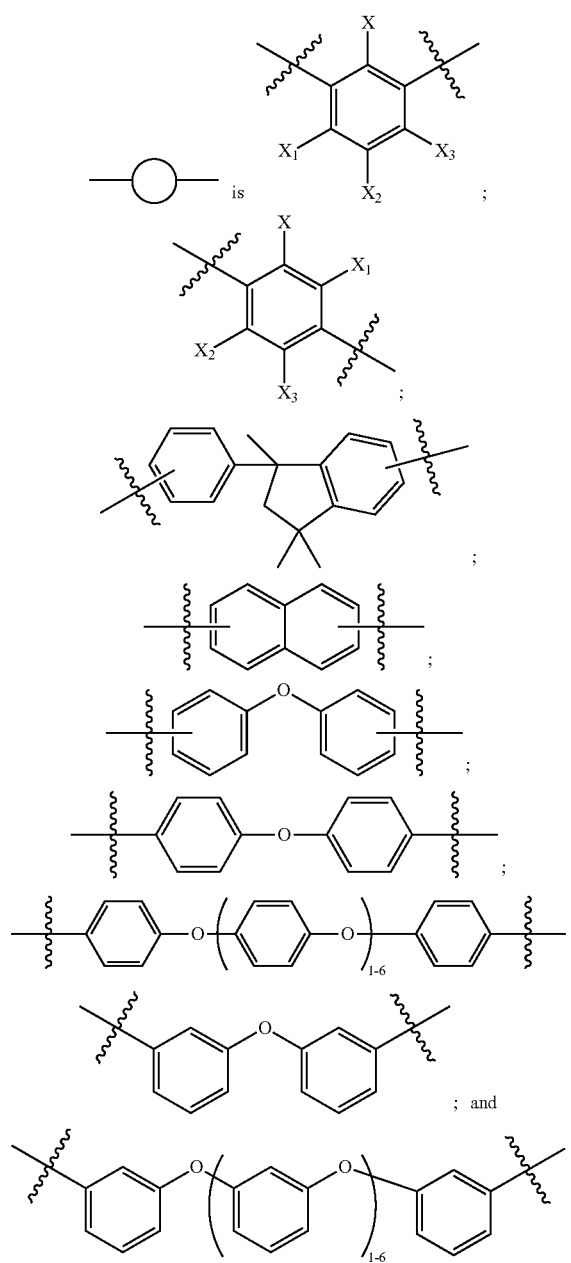

each X, $X_1$, $X_2$ and $X_3$ is independently hydrogen, halogen, or an optionally substituted moiety selected from the group consisting of halogen, aliphatic, alkoxy, phenoxy, aryl, and phenyl; and Q is selected from the group consisting of:

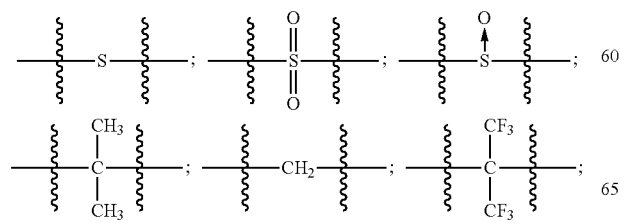

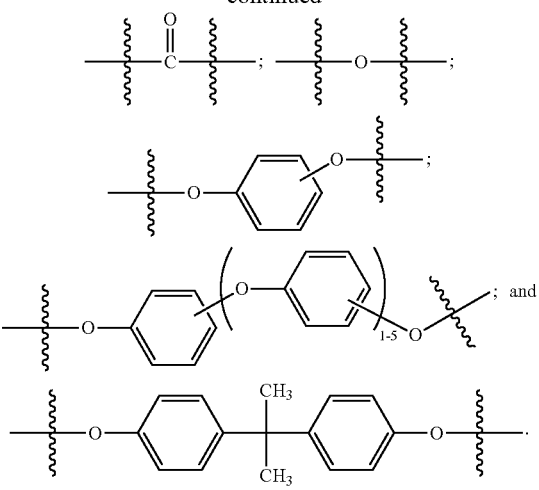

In certain embodiments of the nanofiltration membrane, each

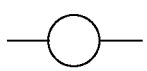

derives from a bivalent diamine group,

selected from the group consisting of:

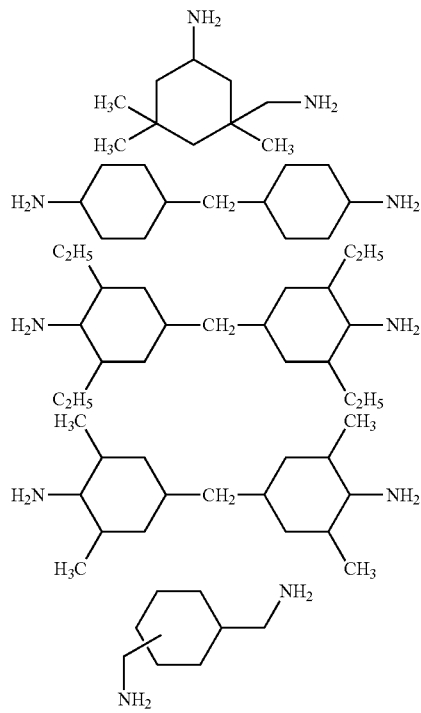

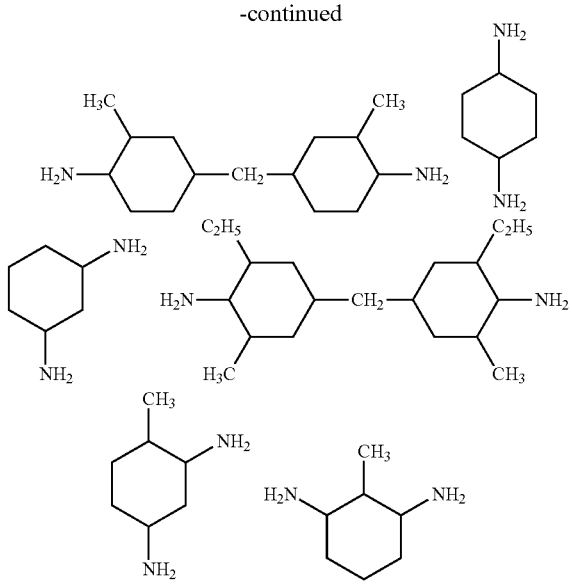
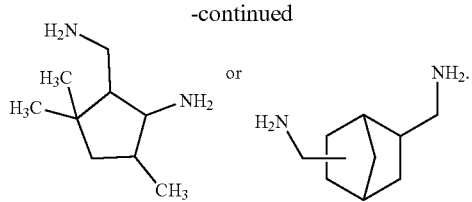

Polyamide-Imide Based OSN Membrane Compositions

In other embodiments, inventive OSN membranes of the present invention comprise polyamide-imide (PAI) based membranes. Like the polyimide membranes described above, PAI membranes are typically cross-linked to increase their solvent resistance. As with polyimides, one method of cross-linking these materials is by treatment with polyamines. This leads to similar problems to those described above for the polyimide membranes and the same solutions described there are also applicable to this class of OSN membranes. In addition, crosslinking PAIs with diamines can lead to transamidation of amide linkages in the polymer or co-polymer chain resulting in residual amine groups arising from sites of chain scission:

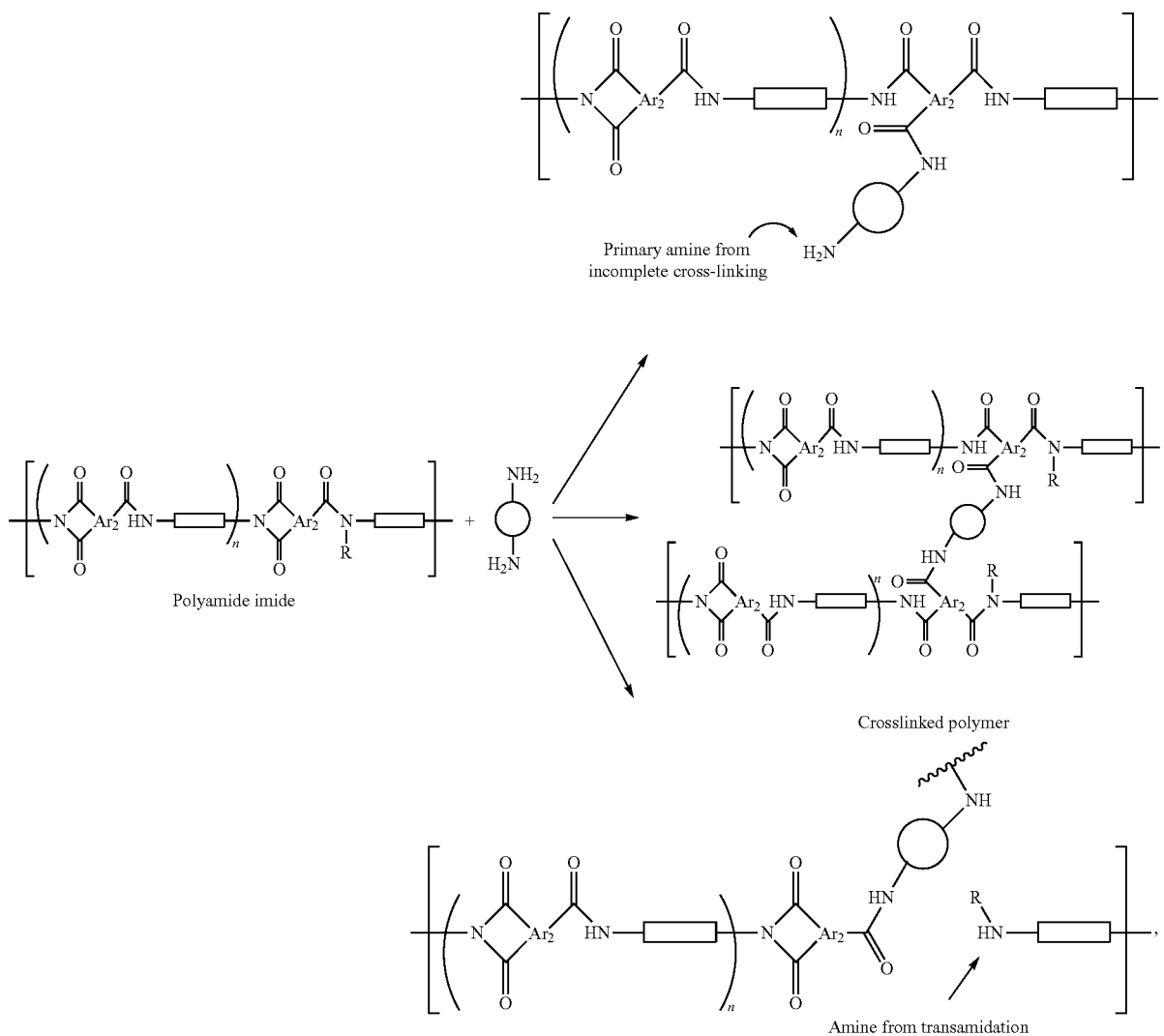

Therefore, in one aspect, the present invention encompasses OSN membrane compositions derived from the cross-linking of polyamide imides followed by treatment with additional reagents to passivate any residual amino groups. In certain embodiments, such membranes comprise cross-linked polyamide imide polymers or co-polymers further the general structure M4 and characterized in that the polymers or co-polymers further contain segments having formula selected from M5, M6, and combinations of both of these:

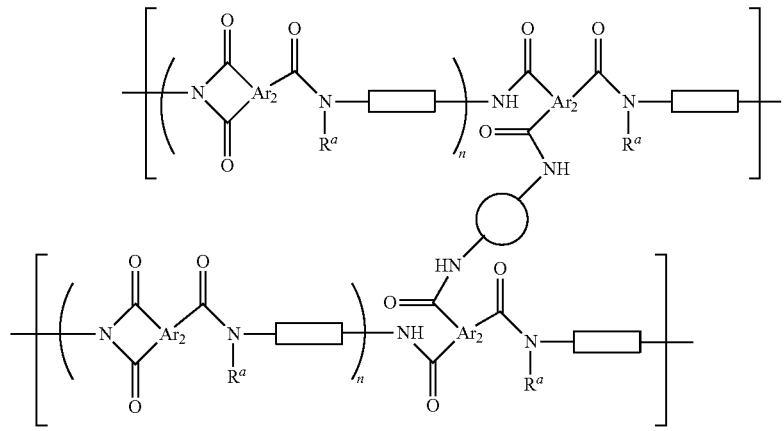

M4

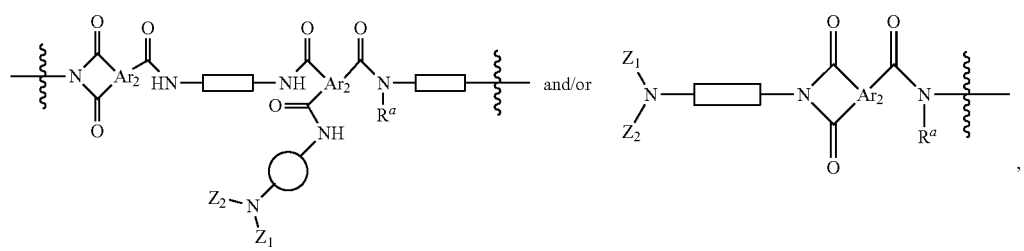

M5     M6 where each of $R^a$, n, $Z_1$, $Z_2$,

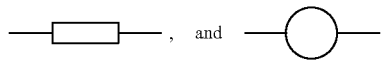, and is as defined above and in the classes and subclasses herein, and Ar$_2$ is a trivalent aromatic moiety.

In certain other embodiments, OSN membranes of the present invention comprise cross-linked polyamide imide (PAI) polymers or co-polymers having structures M7, M8, and/or M9 and characterized in that the polymers or co-polymers further contain segments having formula selected from M10, M11, M12, M6, and combinations of any two or more of these:

M7
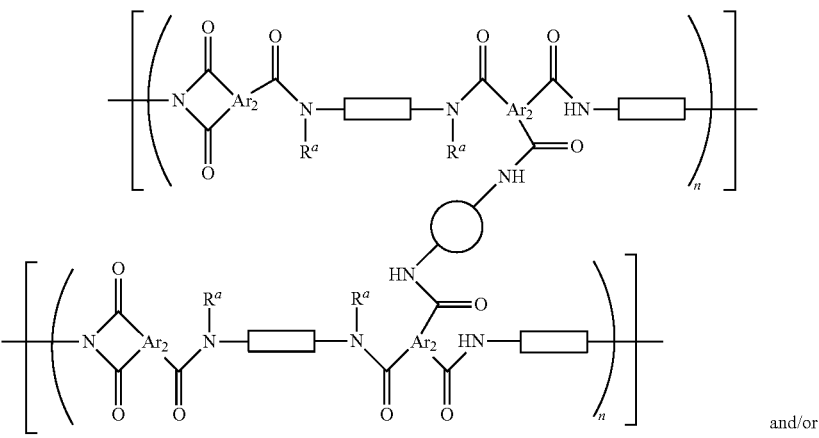
and/or
M8
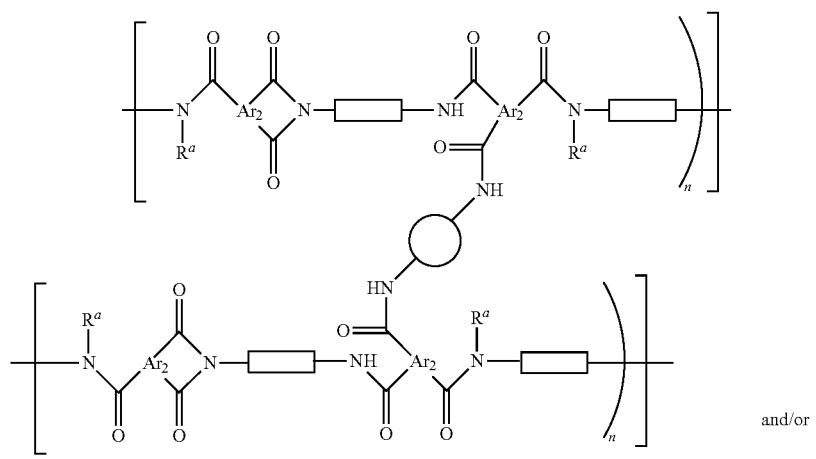
and/or
M9
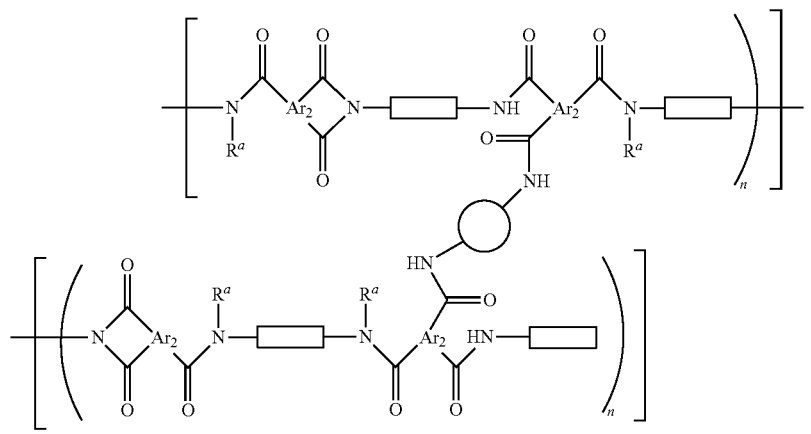
and/or
M10 M11
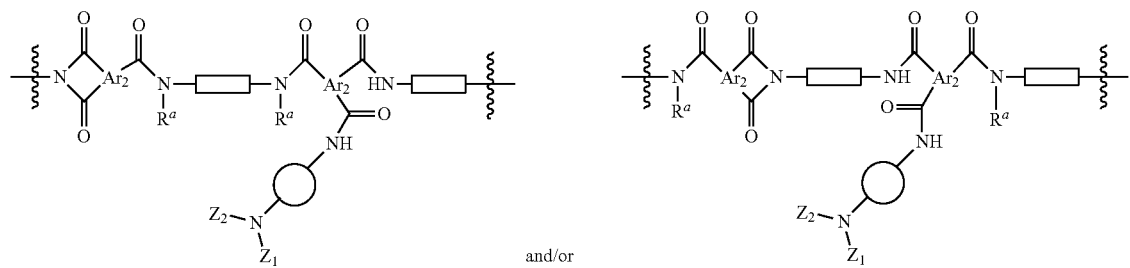
and/or and/or

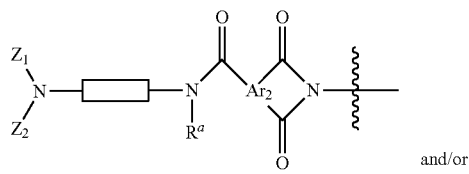
M12

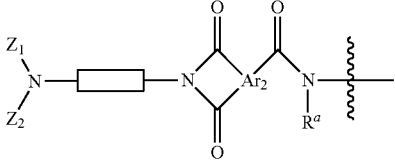
M6 and/or where each of $Ar_2$, $R^a$, n, $Z_1$, $Z_2$,

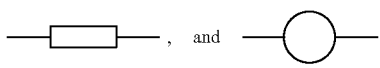

and is as defined above and in the classes and subclasses herein.

In certain embodiments, $Ar_2$ in formulae M4, M5, M6, M7, M8, M9, M10, M11, and M12, is independently selected at each occurrence from the group consisting of:

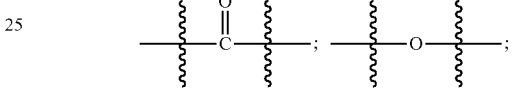

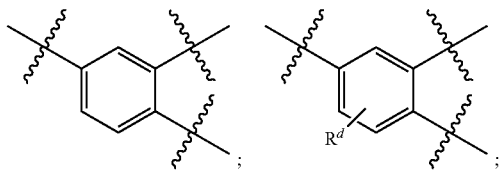

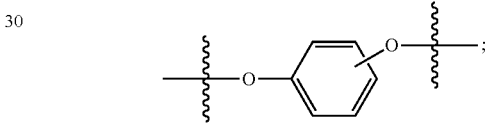

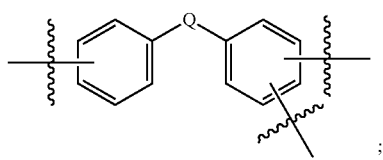

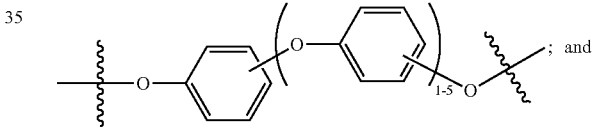

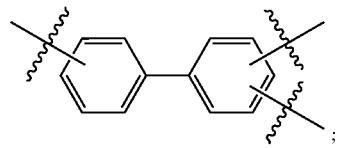

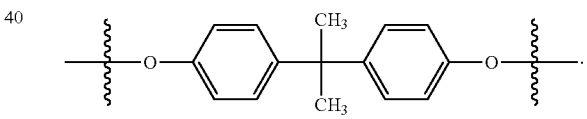

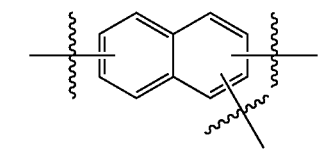

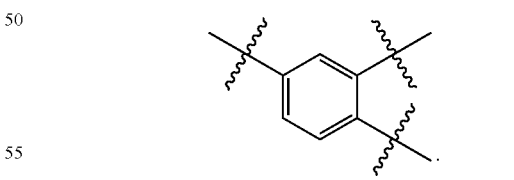

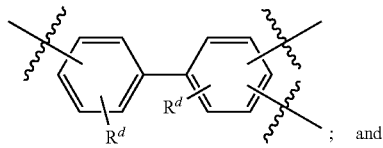

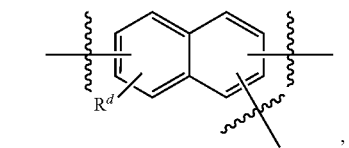

In certain embodiments, $Ar_2$ in formulae M4, M5, M6, M7, M8, M9, M10, M11, and M12, is

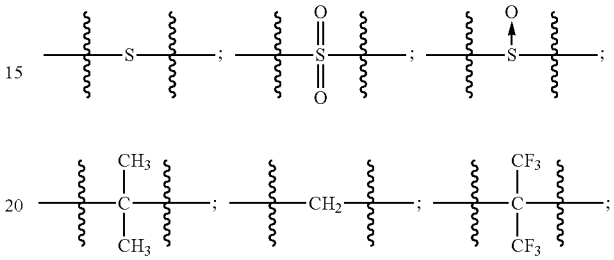

In certain embodiments, each

where $R^d$ is as defined above and in the classes and subclasses herein and -Q- is selected from the group consisting of:

moiety in formulae in formulae M4, M5, M6, M7, M8, M9, M10, M11, and M12, is independently selected from the group consisting of:

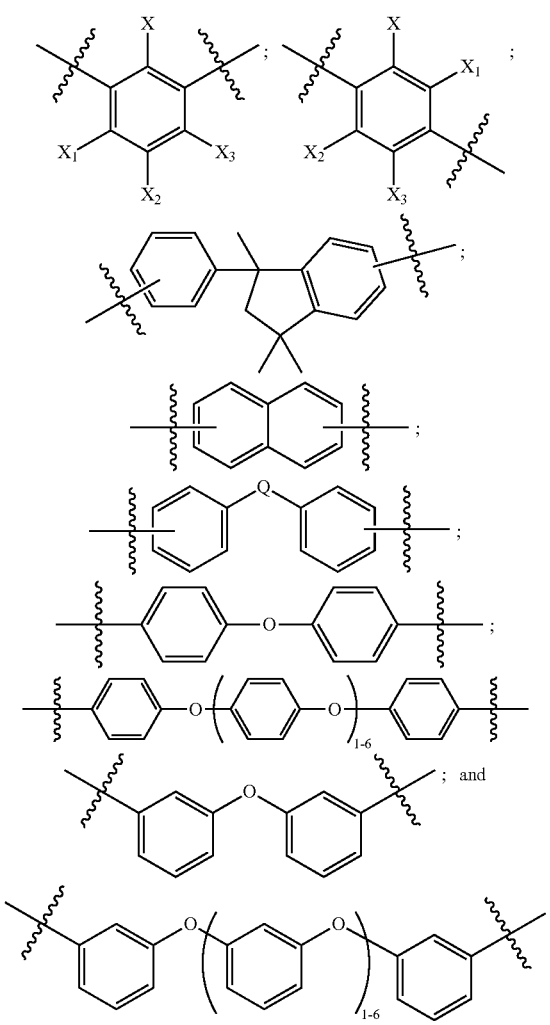

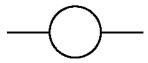

wherein Q is as defined above and in the classes and subclasses herein, and each of X, $X_1$, $X_2$ and $X_3$ are independently hydrogen, halogen, or an optionally substituted moiety selected from the group consisting of aliphatic, alkoxy, phenoxy, aryl, and phenyl.

In certain embodiments, each

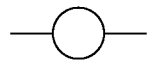

moiety in formulae M4, M5, M6, M7, M8, M9, M10, M11, and M12, is a bivalent $C_{2-20}$ aliphatic group. In certain embodiments, each

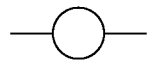

moiety in the formulae above is —$CH_2CH_2$—; —$CH_2CH_2CH_2$—; —$CH_2(CH_2)_2CH_2$—; —$CH_2(CH_2)_4$ $CH_2$—; —$CH_2(CH_2)_4CH_2$—; —$CH_2(CH_2)_6CH_2$—; —$CH_2(CH_2)_8CH_2$—; —$CH_2(CH_2)_{10}CH_2$—; —$CH_2(CH_2)_{12}CH_2$—; —$CH_2(CH_2)_{14}CH_2$—; or —$CH_2(CH_2)_{16}CH_2$—.

In certain embodiments, each

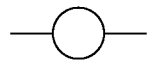

moiety in formulae M4, M5, M6, M7, M8, M9, M10, M11, and M12, is a bivalent moiety derived from a diamine. Suitable diamines include, but are not limited to: $C_{2-20}$ aliphatic diamines, ethylene diamine, propylene diamine, tetramethylene diamine, 1,6-hexamethylene diamine, 1,12-Dodecanediamine, 1,10-Decanediamine, Norbornane diamine, bis(6-aminohexyl)ether, tricyclodecane diamine, 3,4-diaminofuran, and cycloaliphatic diamines such as those having the following structures:

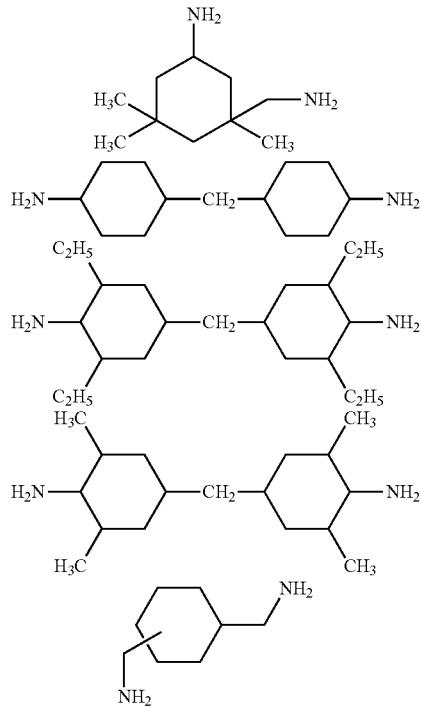

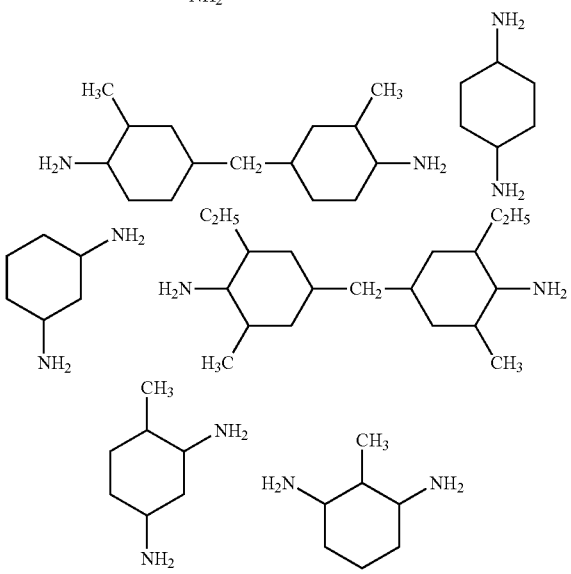

-continued

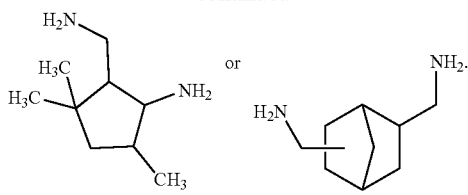

In certain embodiments, each

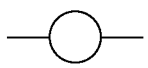

moiety in formulae M4, M5, M6, M7, M8, M9, M10, M11, and M12, is a bivalent aromatic group. In certain embodiments, such bivalent aromatic groups are independently selected from the group consisting of:

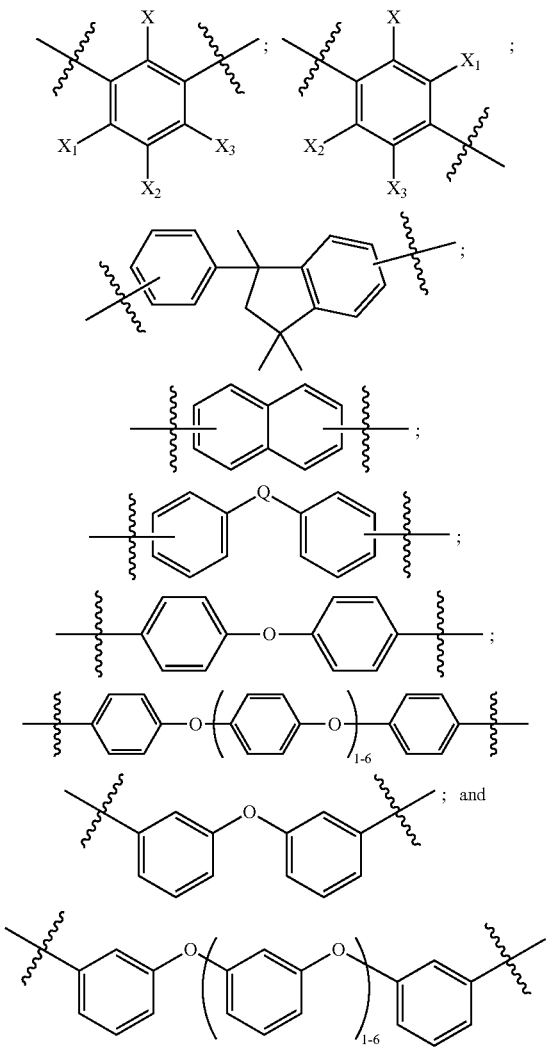

wherein each of X, $X_1$, $X_2$, $X_3$, and Q is as defined above and in the classes and subclasses herein.

In certain embodiments, the present invention encompasses cross-linked PAI OSN membrane compositions containing segments within the PAI having any of formulae M5a-M5j:

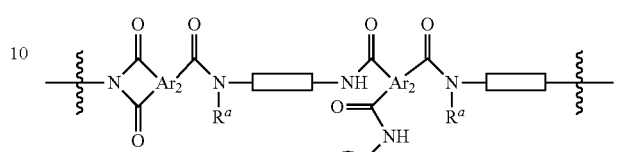

M5a

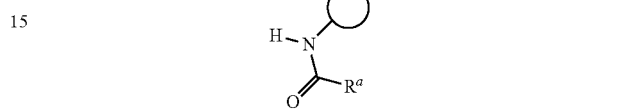

M5b

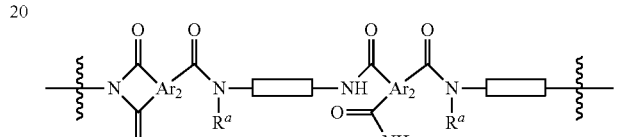

M5c

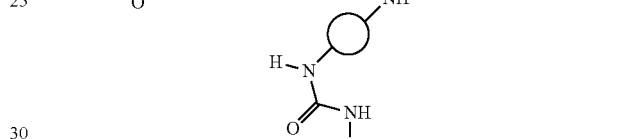

M5d

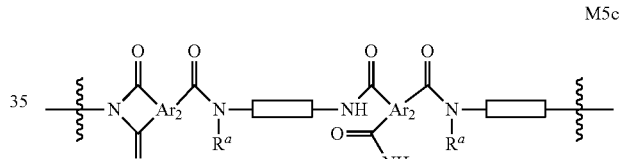

M5e

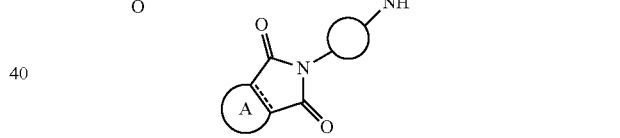

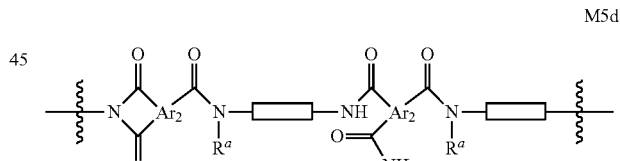

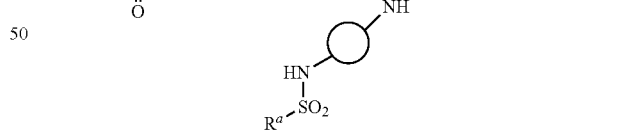

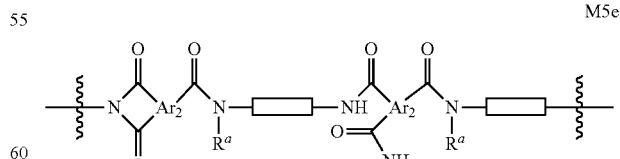

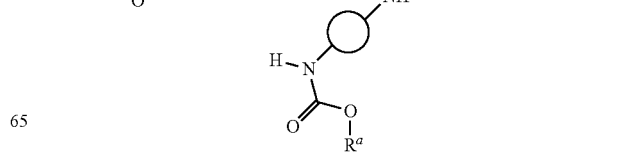

-continued

M5f
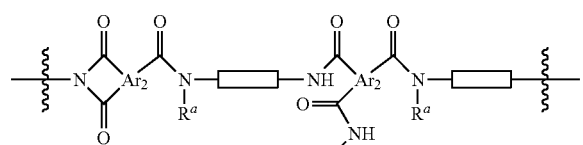

M5g
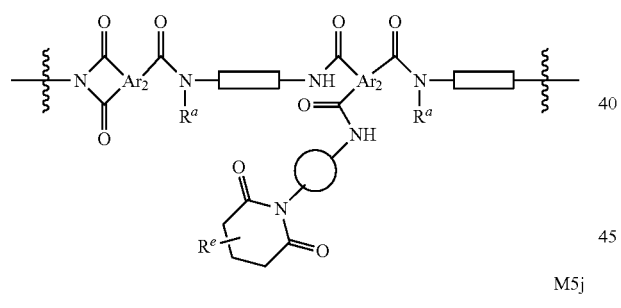

M5h
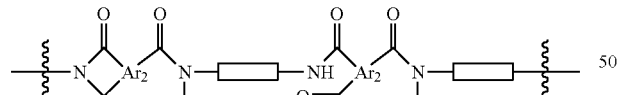

M5i
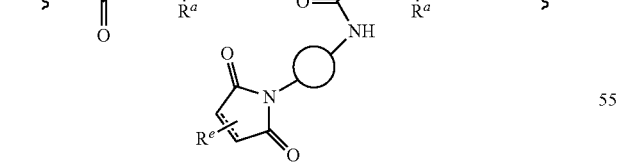

M5j
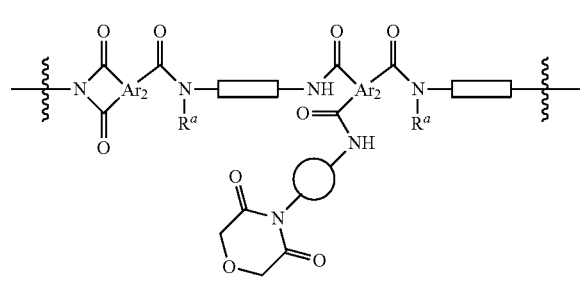

wherein,
each of $Ar_2$, $R^a$, $R^b$, $R^c$, $R^d$, ring A, ring B,

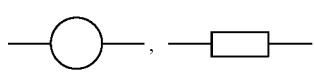

and is as defined above and in the classes and subclasses herein.

In certain embodiments, the present invention provides cross-linked PAI OSN membranes characterized in that they comprise moieties of formula M5a. In certain embodiments, such membranes comprise moieties selected from the group consisting of:

M5a-1
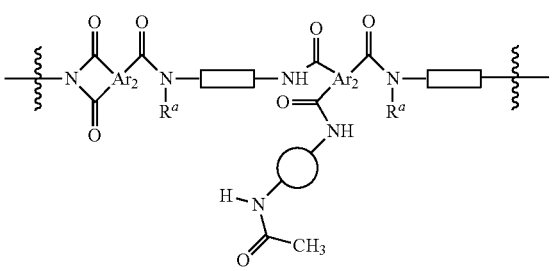

M5a-2
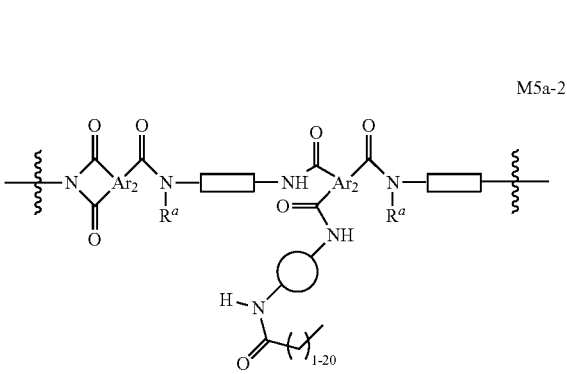

M5a-3
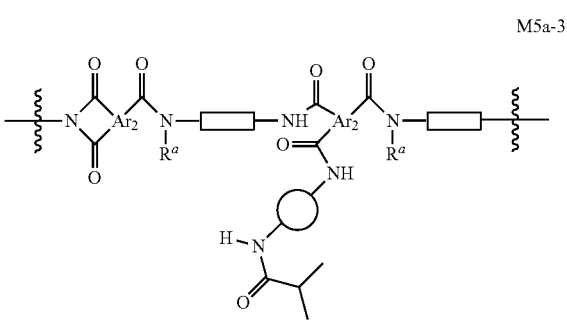

M5a-4
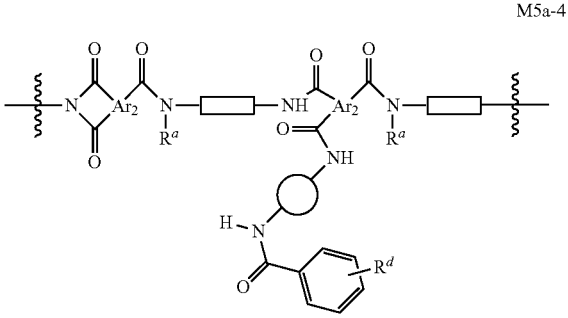

M5a-5

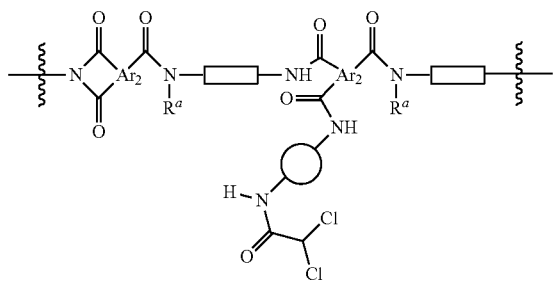

M5b-1

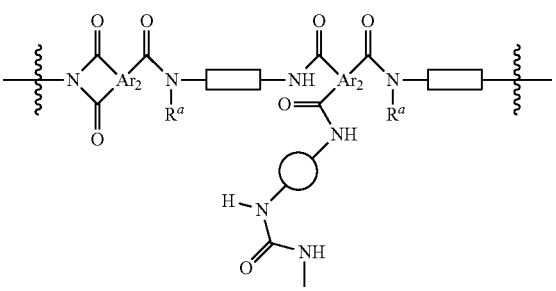

M5a-6

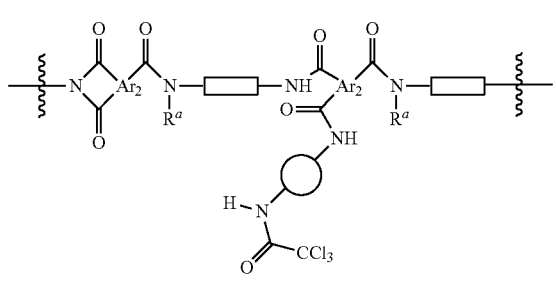

M5a-7

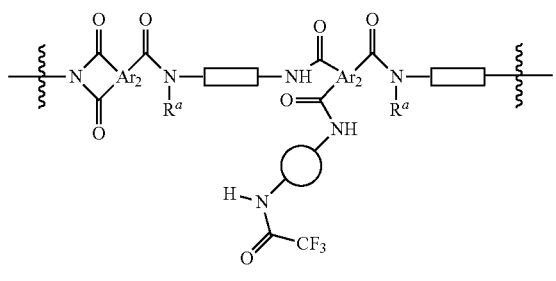

M5b-2

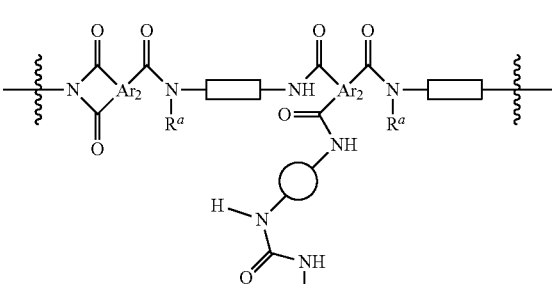

M5b-3

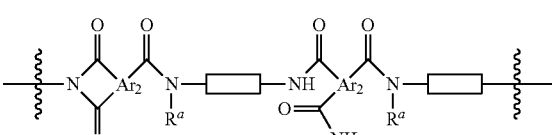

M5a-8

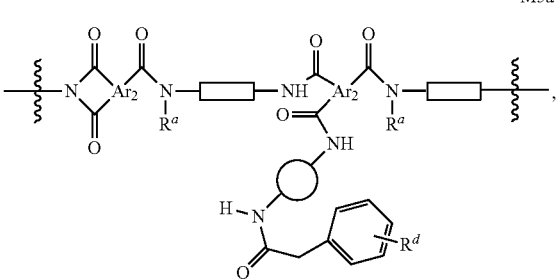

wherein each of $R^a$, $R^d$ $Ar_2$,

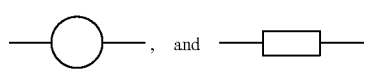

is as defined above and in the classes and subclasses herein, and

In certain embodiments, the present invention provides cross-linked PAI OSN membranes characterized in that they comprise moieties of formula M5b. In certain embodiments, such membranes comprise moieties selected from the group consisting of:

M5b-4

-continued

M5b-5
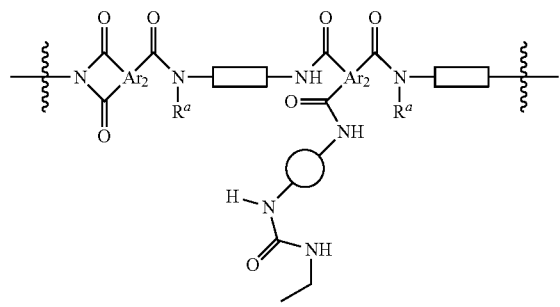

M5b-6
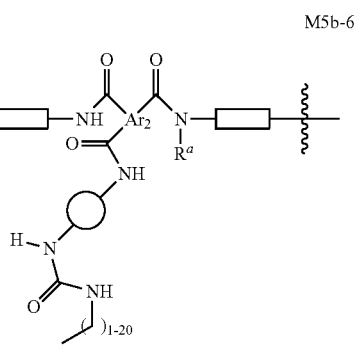

M5b-7
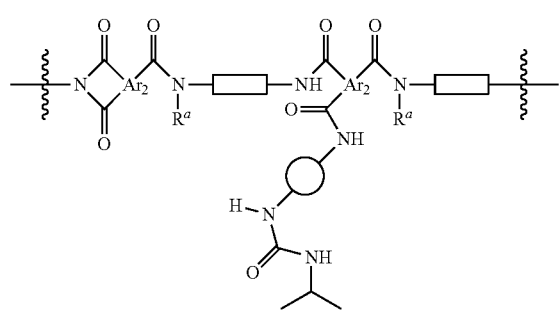

M5b-8
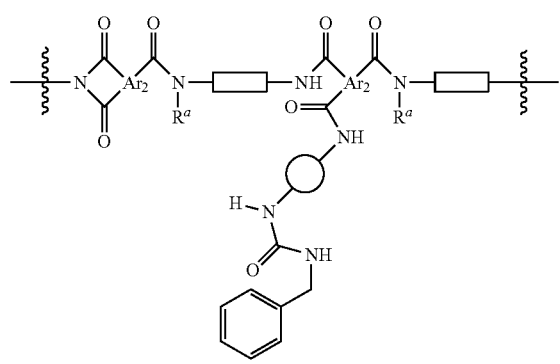

-continued

M5b-9
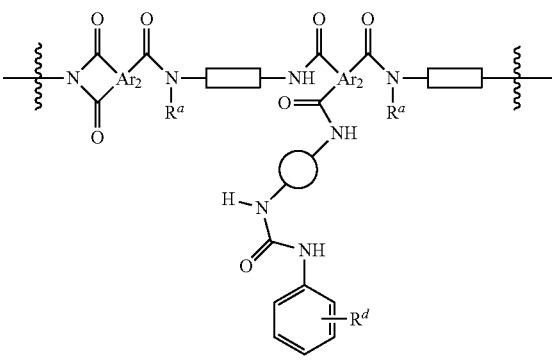

M5b-10
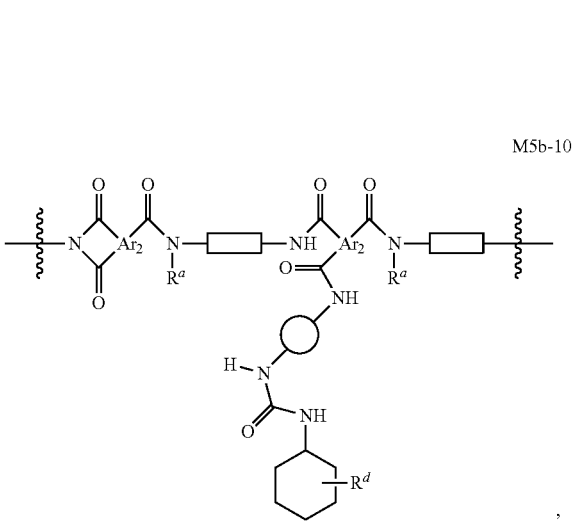

wherein each of $Ar_2$, $R^a$, $R^d$,

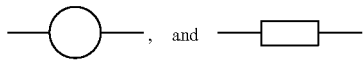

is as defined above and in the classes and subclasses herein.

In certain embodiments, the present invention provides cross-linked PAI OSN membranes characterized in that they comprise moieties of formula M5c. In certain embodiments, such membranes comprise moieties selected from the group consisting of:

M5c-1
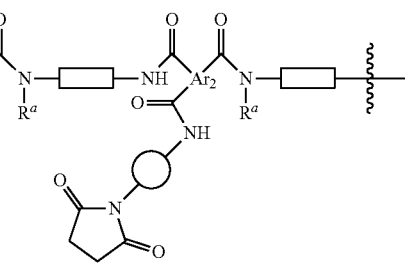

M5c-2
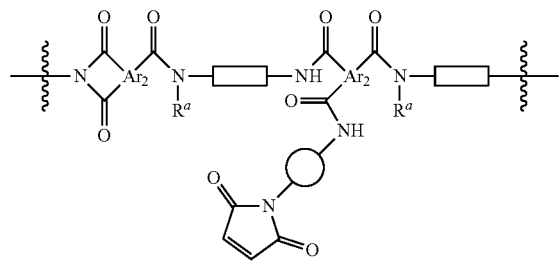
M5c-3
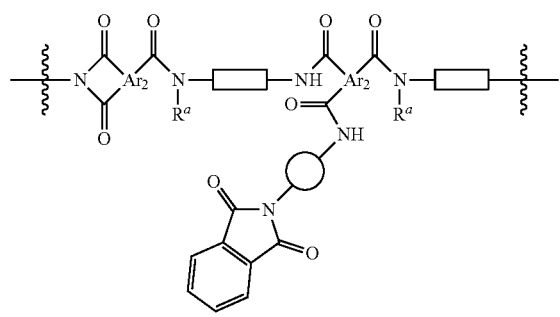
M5c-4
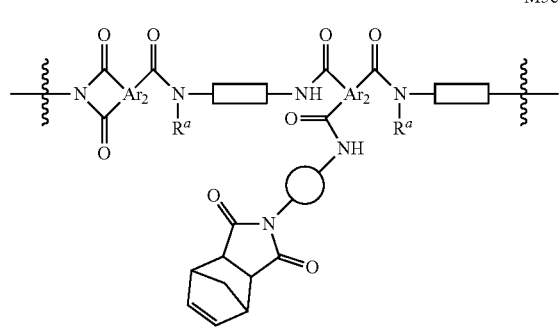
M5c-5
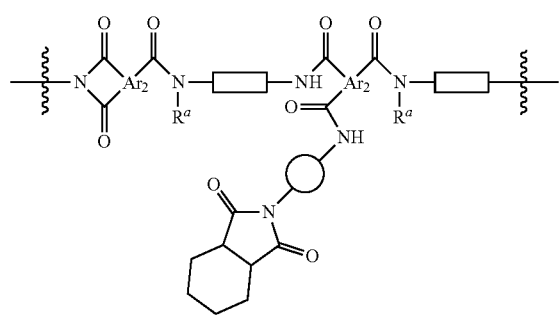
M5c-6
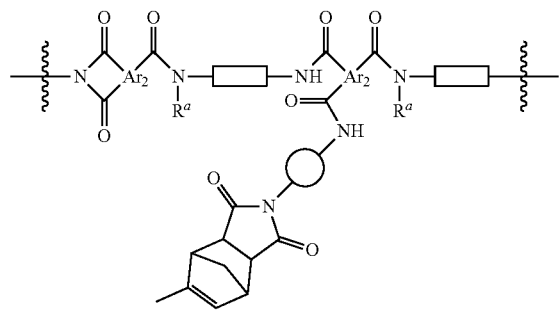
M5c-7
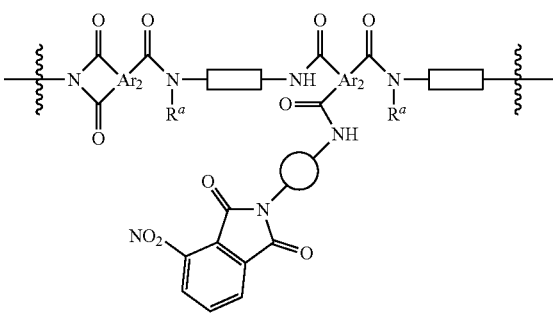
M5c-8
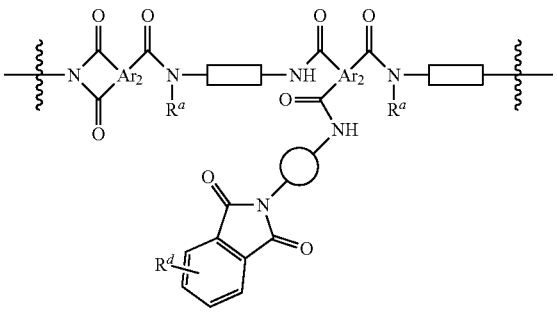
wherein each of $Ar_2$, $R^a$, $R^d$,
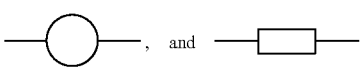
is as defined above and in the classes and subclasses herein.
In certain embodiments, the present invention provides cross-linked PAI OSN membranes characterized in that they comprise moieties of formula M5d. In certain embodiments, such membranes comprise moieties selected from the group consisting of:
M5d-1
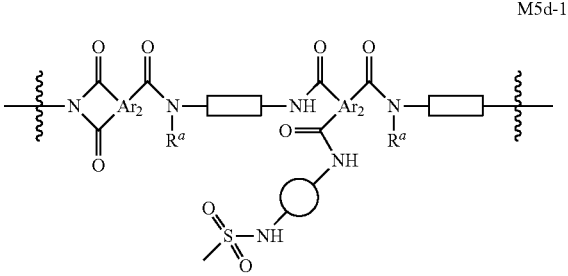

M5d-2
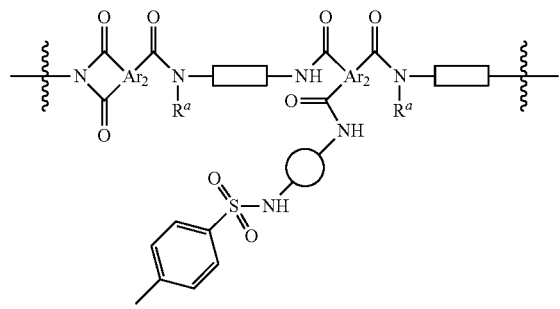

M5d-3
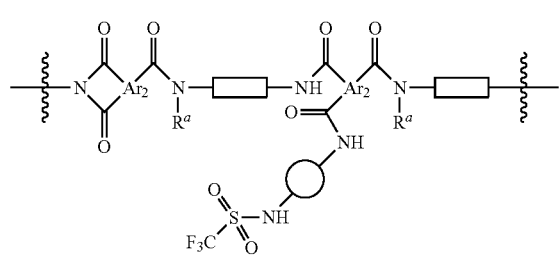

M5d-4
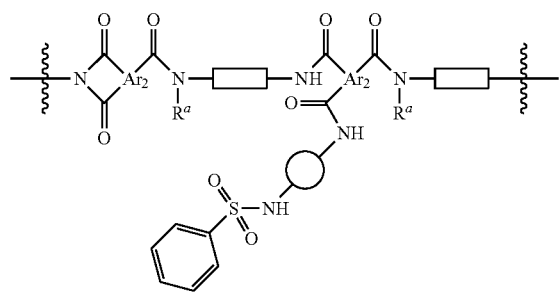

M5d-5
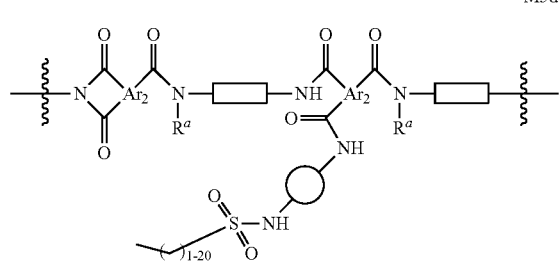

M5d-6
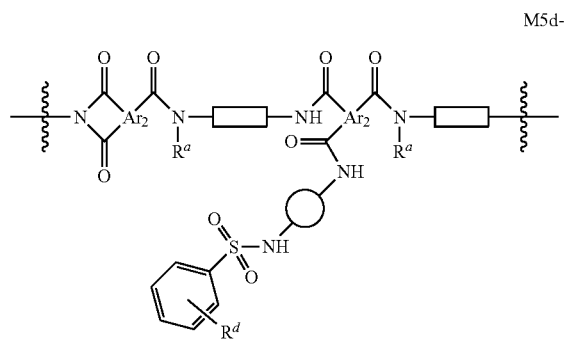

M5d-7
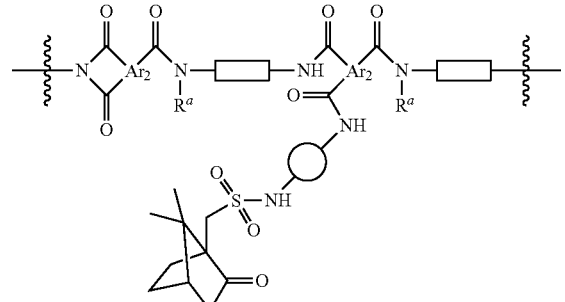

M5d-8
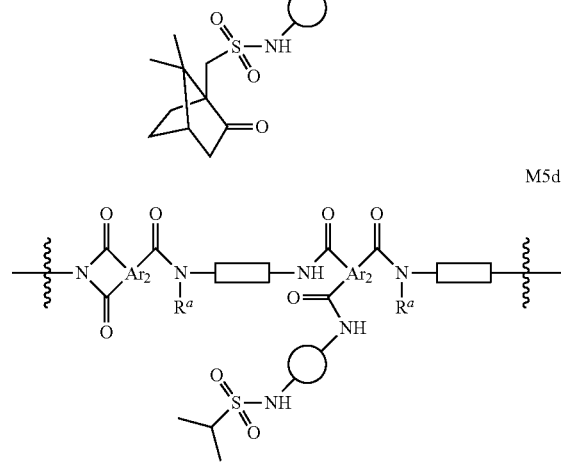

M5d-9
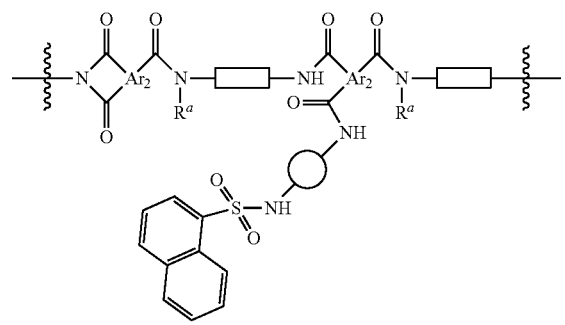

M5d-10
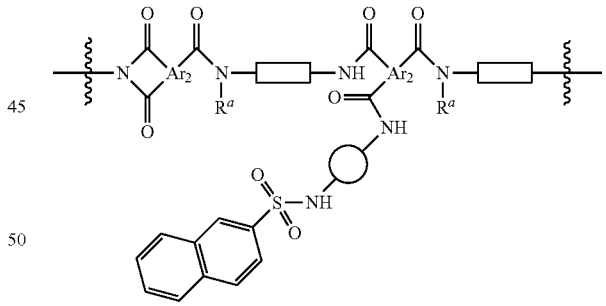

wherein each of $Ar_2$, $R^a$, $R^d$,

—◯—, and —▭— is as defined above and in the classes and subclasses herein.

In certain embodiments, the present invention provides cross-linked PAI OSN membranes characterized in that they comprise moieties of formula M5e. In certain embodiments, such membranes comprise moieties selected from the group consisting of:

M5e-1
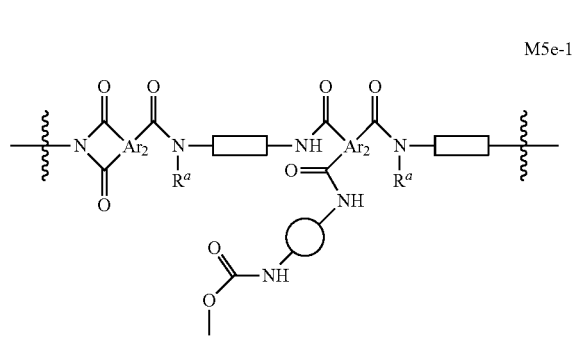
M5e-2
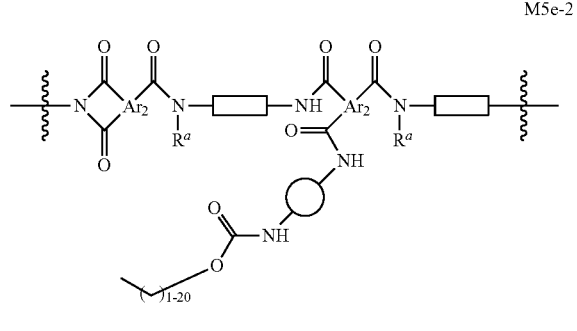
M5e-3
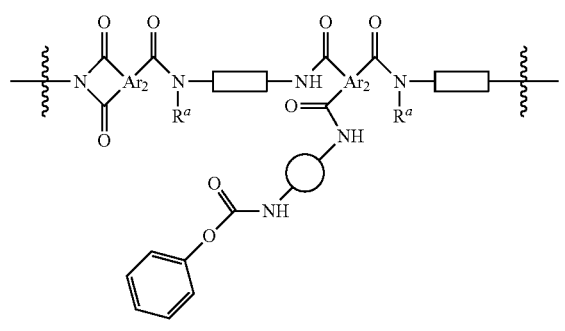
M5e-4
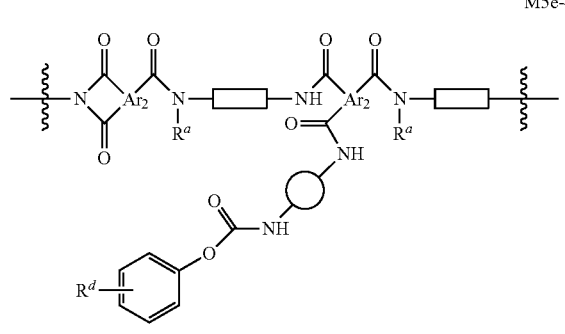
M5e-5
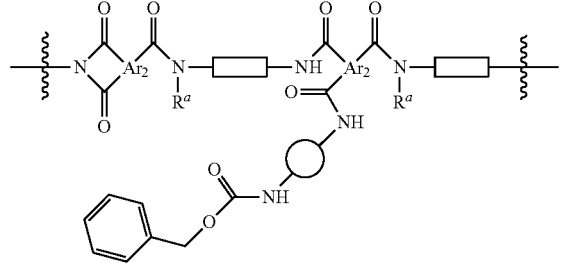
M5e-6
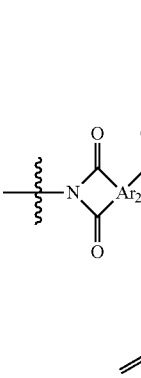
M5e-7
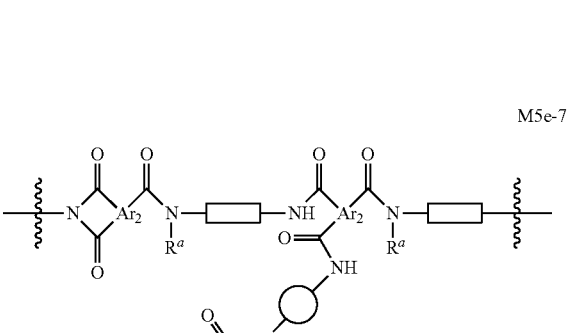
M5e-8
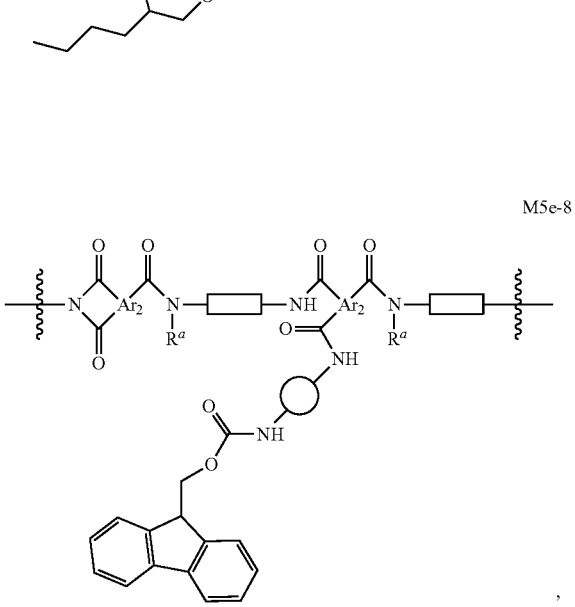
wherein each of $Ar_2$, $R^a$, $R^d$,
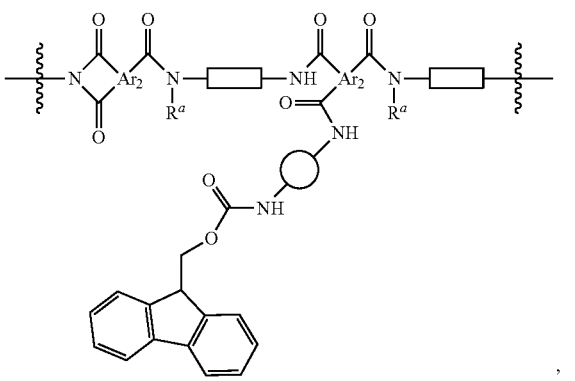
is as defined above and in the classes and subclasses herein.
In certain embodiments, the present invention provides cross-linked PAI OSN membranes characterized in that they comprise moieties of formula M5f. In certain embodiments, such membranes comprise moities selected from the group consisting of:

M5f-1 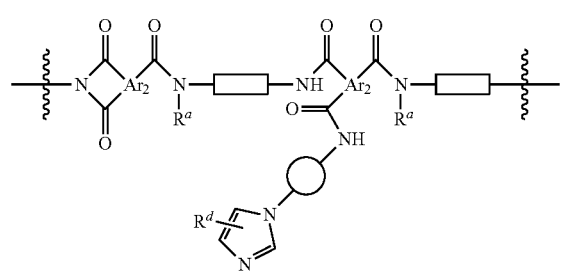
M5f-2 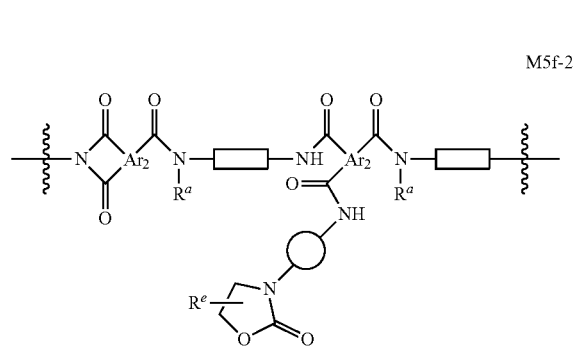
M5f-3 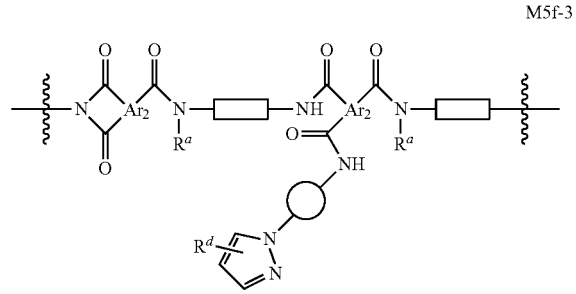
M5f-4 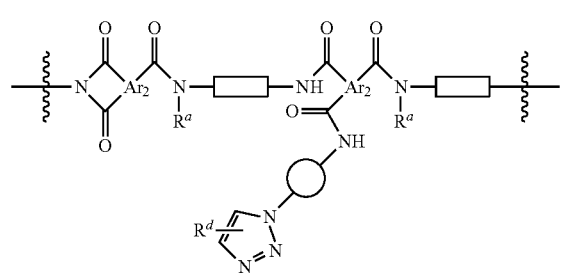
M5f-5 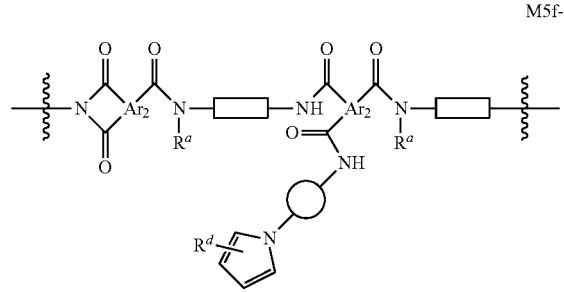
-continued
M5f-6 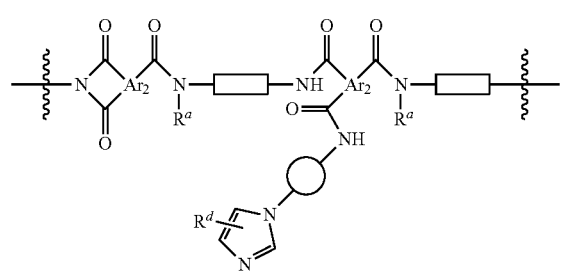
M5f-7 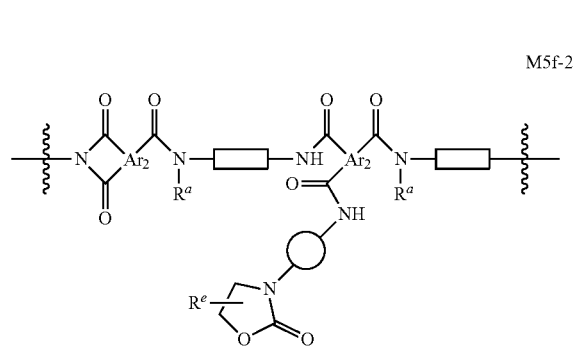
M5f-8 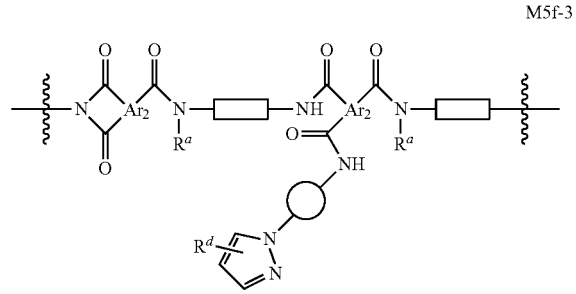
M5f-9 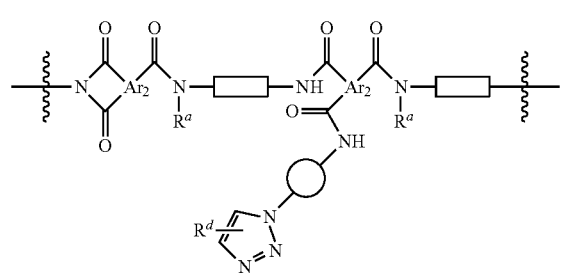
M5f-10 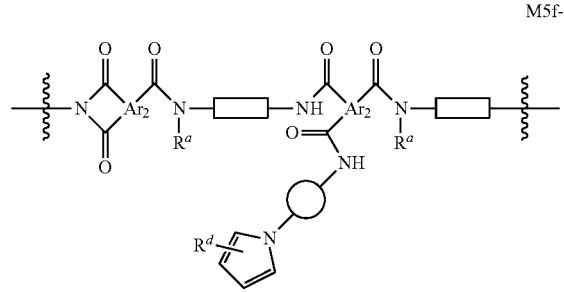

M5f-11

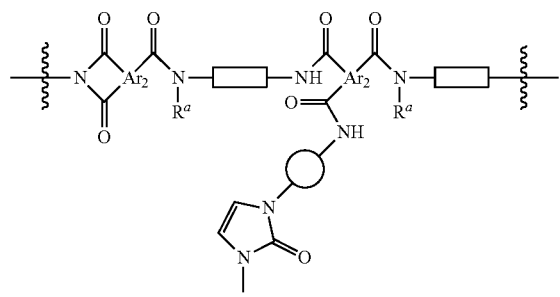

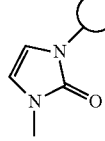

M5f-12

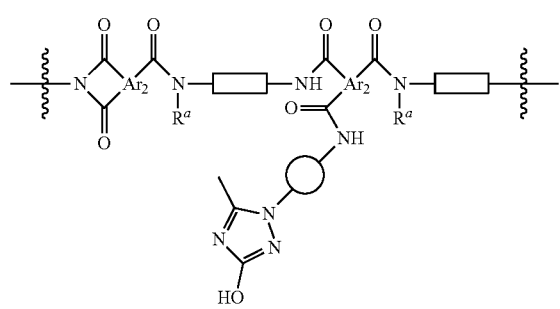

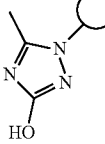

M5f-13

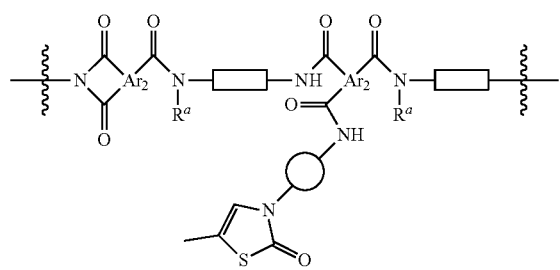

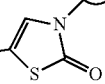

M5f-14

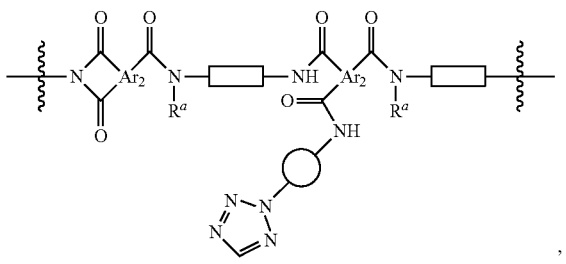

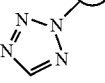

wherein each of $Ar_2$, $R^a$, , $R^d$, $R^e$,

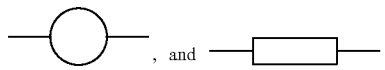

is as defined above and in the classes and subclasses herein.

In certain embodiments, the present invention provides cross-linked PAI OSN membranes characterized in that they comprise moieties of formula M5g. In certain embodiments, such membranes comprise moieties selected from the group consisting of:

M5g-1

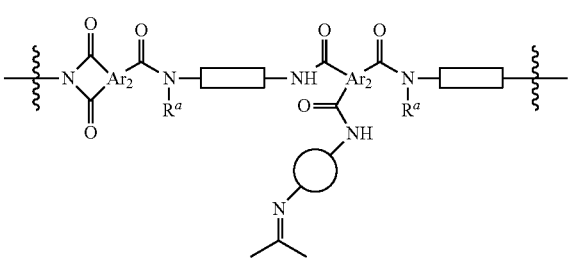

M5g-2

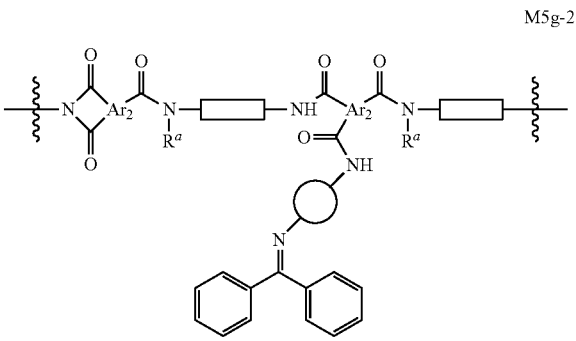

wherein each of $Ar_2$,

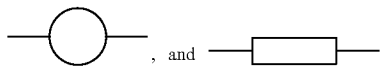

is as defined above and in the classes and subclasses herein.

In certain embodiments, the present invention provides cross-linked PAI OSN membranes characterized in that they comprise moieties of formula M5h.

In certain embodiments, the present invention provides cross-linked PAI OSN membranes characterized in that they comprise moieties of formula M5i.

In certain embodiments, the present invention provides cross-linked PAI OSN membranes characterized in that they comprise moieties of formula M5j. In certain embodiments, such membranes comprise moieties selected from the group consisting of:

M5j-1

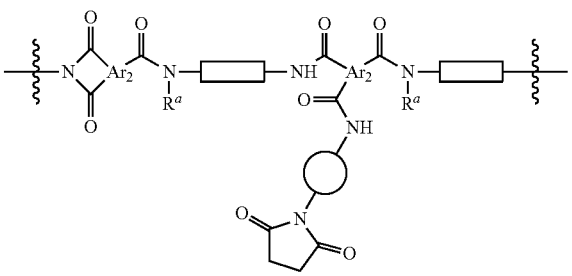

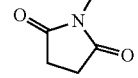

M5j-2
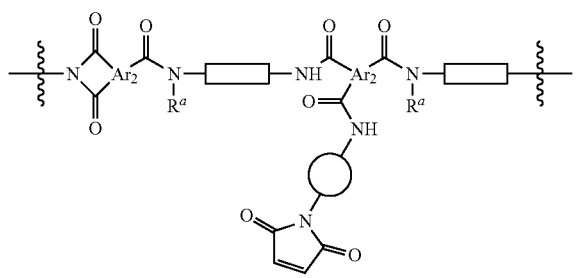

M5j-6
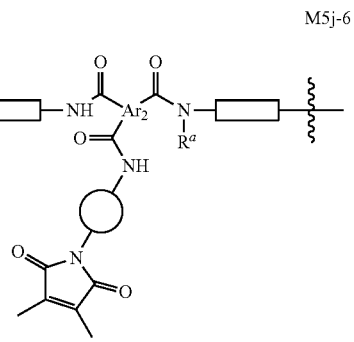

M5j-3
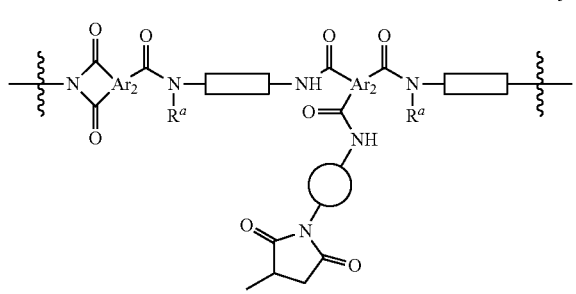

M5j-7
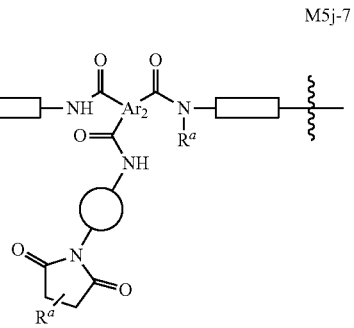

M5j-4
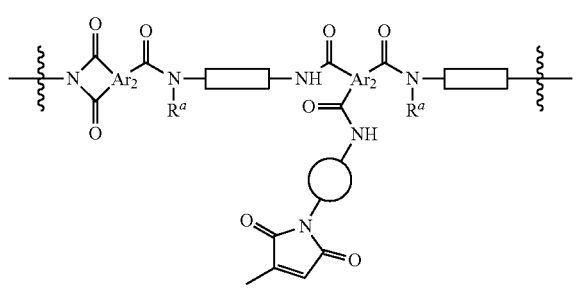

M5j-8
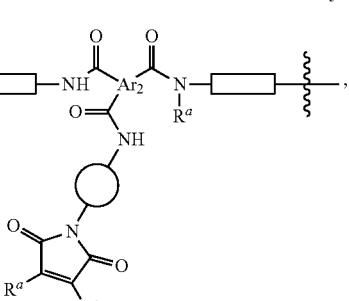

wherein each of $R^a$, $R^b$, $Ar_2$,

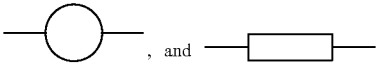, and is as defined above and in the classes and subclasses herein.

In another aspect, the present invention encompasses OSN membrane compositions derived from the cross-linking of PAIs followed by treatment to remove any residual amino groups. In certain embodiments, such membranes comprise cross-linked PAI polymers or co-polymers having the general structure M4 and characterized in that the polymers or co-polymers further contain segments having formula M13:

M5j-5
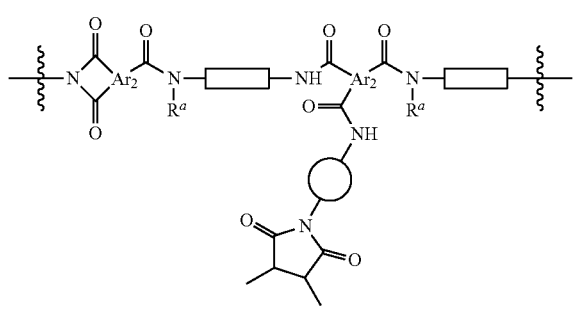

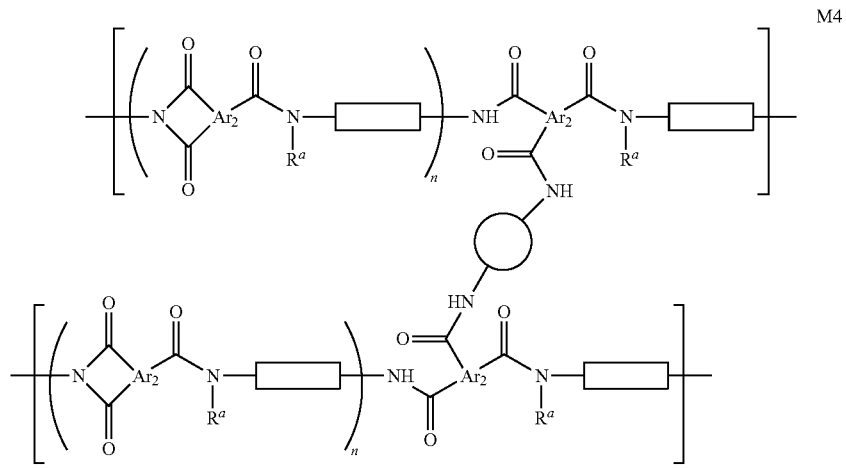
M4
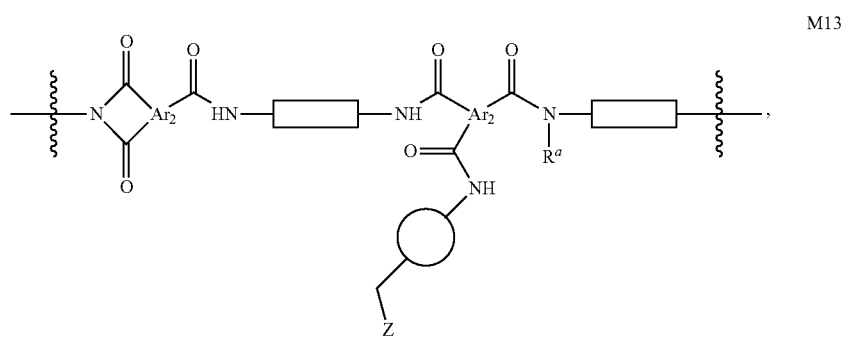
M13
wherein each of $Ar_2$, $R^a$, n,
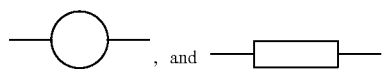
, and
is as defined above and in the classes and subclasses herein, and Z is a functional group that does not contain a nitrogen atom.
In certain embodiments, the present invention encompasses cross-linked PAI OSN membrane compositions containing segments within the PAI polymer or co-polymer having any of formulae M13a-M13d:
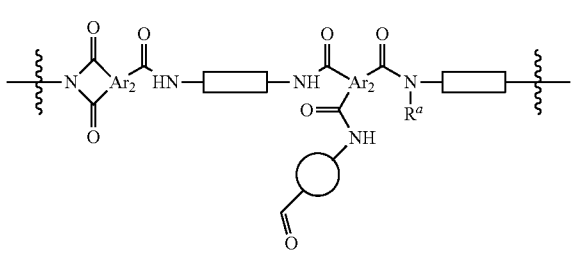
M13a
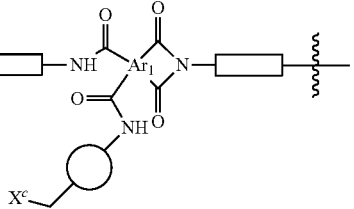
M13b
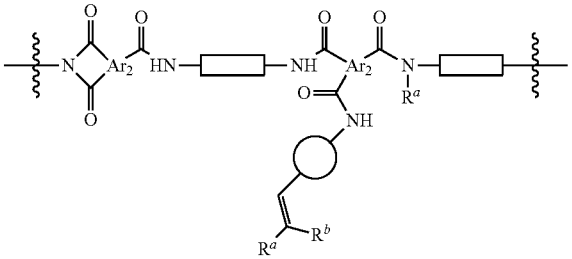
M13c -continued M13d

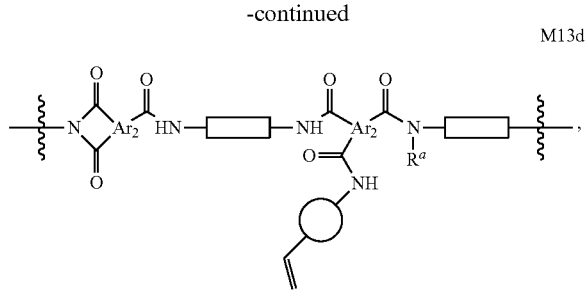

wherein each of $Ar_2$, $R^a$, $R^b$,

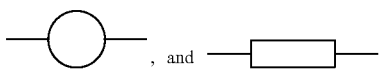

is as defined above and in the classes and subclasses herein and $X^c$ is —Cl, —Br or —I.

In certain embodiments, polyamide imide-based OSN membranes of the present invention are characterized in that they contain very few or no free amine functional groups. Such amine functional groups can arise from incomplete crosslinking procedures as just described, or they can be present in the polyamide imides prior to cross-linking.

In certain embodiments, for any of formulae M5a-1 through M5j-8, M13, and Ma13a through M13d, the moiety

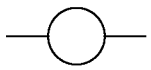

is an aliphatic group. In certain embodiments, for any of formulae M5a-1 through M5j-8, M13, and Ma13a through M13d, the moiety

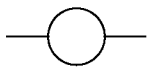

is —CH$_2$CH$_2$—. In certain embodiments, for any of formulae M5a-1 through M5j-8, M13, and Ma13a through M13d, the moiety

is —CH$_2$CH$_2$—. In certain embodiments, for any of formulae M5a-1 through M5j-8, M13, and Ma13a through M13d, the moiety

is —CH$_2$CH$_2$CH$_2$—. In certain embodiments, for any of formulae M5a-1 through M5j-8, M13, and Ma13a through M13d, the moiety

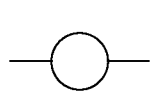

is —CH$_2$(CH$_2$)$_{2CH2}$. In certain embodiments, for any of formulae M5a-1 through M5j-8, M13, and Ma13a through M13d, the moiety

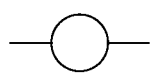

is —CH$_2$(CH$_2$)$_4$CH$_2$—.

In certain embodiments, for any of formulae M5a-1 through M5j-8, M13, and Ma13a through M13d, the moiety

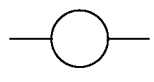

is an aromatic group. In certain embodiments, for any of formulae M2a-1 through M2j-8 and M3, M3a and M3b, the moiety

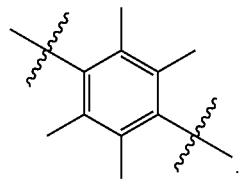

In certain embodiments, for any of formulae M5a-1 through M5j-8, M13, and Ma13a through M13d, the moiety

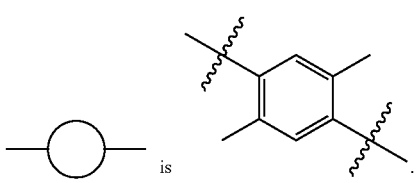

In certain embodiments, for any of formulae M5a-1 through M5j-8, M13, and Ma13a through M13d, the moiety

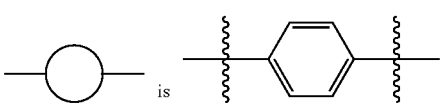

In certain embodiments, for any of formulae M5a-1 through M5j-8, M13, and Ma13a through M13d, the moiety

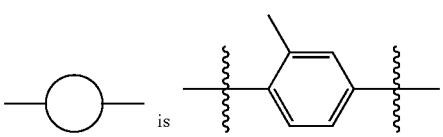

In certain embodiments, for any of formulae M5a-1 through M5j-8, M13, and Ma13a through M13d, the moiety

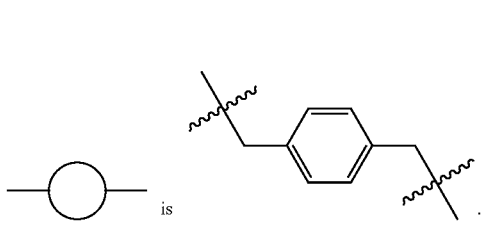

In certain embodiments, for any of formulae M5a-1 through M5j-8, M13, and Ma13a through M13d, the moiety

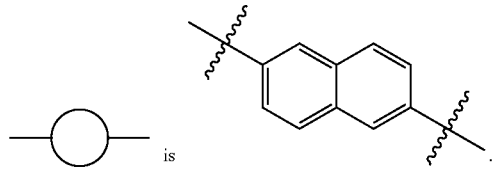

In certain embodiments, for any of formulae M5a-1 through M5j-S, M13, and Ma13a through M13d, Ar₂ has the formula

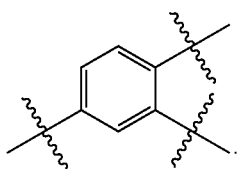 [SMILES: *c1ccc(*)c(*)c1]

In certain embodiments, for any of formulae M2a-1 through M2j-8 and M3, M3a and M3b, the moiety

has the formula

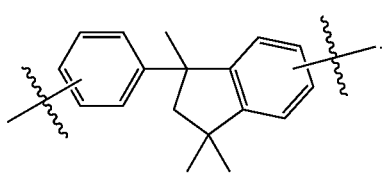

In certain embodiments, for any of formulae M5a-1 through M5j-8, M13, and Ma13a through M13d, the moiety

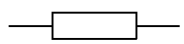

has the formula

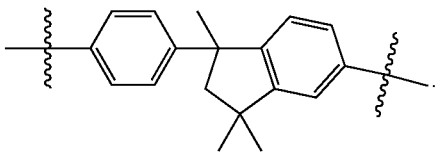 [SMILES: *c1ccc(C2(C)CC(C)(C)c3cc(*)ccc32)cc1]

In certain embodiments, for any of formulae M5a-1 through M5j-8, M13, and Ma13a through M13d, Ar₂ has the formula

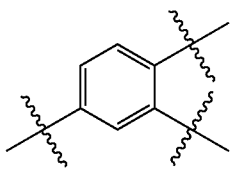 [SMILES: *c1ccc(*)c(*)c1]

and the moiety

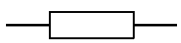

has the formula

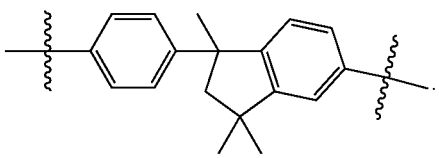

In certain embodiments, for any of formulae M5a-1 through M5j-8, M13, and Ma13a through M13d, Ar₂ has the formula

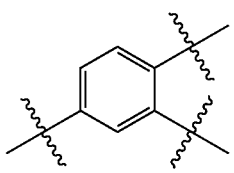 [SMILES: *c1ccc(*)c(*)c1]

and the moiety

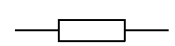

has the formula

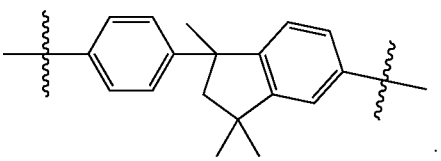 [SMILES: *c1ccc(C2(C)CC(C)(C)c3cc(*)ccc32)cc1]

Just as the preceding paragraphs present compositions of the present invention based on polyamide imide polymers or co-polymers of formula M4, the present invention likewise encompasses analogous OSN membranes based on polyamide imide polymers or co-polymers of any of formulae M7, M8, and M9, as well as mixtures of any of these with each other or with polymers or co-polymers of formula M4. It is to be understood therefore, that each of the genera described above for polymers or co-polymers containing segments of M5 resulting from substitution of formula M5 with formulae M10 or M11 are also contemplated and encompassed by the present invention. Likewise, OSN membranes comprising mixtures of any of these are also contemplated.

It is well understood in the art that polyamide imide compositions can be manufactured with various chemistries utilizing combinations of anhydrides, acid chlorides and isocyanates in combination with diamines and that the resulting polymers or co-polymers have a variety of structures. While the inventors have shown here several possibilities based on the more common polyamide imide polymers or co-polymers of formulae M4, M7, M8, and M9, the skilled artisan will recognize that additional polyamide imide polymers or co-polymers exist (for example those resulting from the inclusion of tetrafunctional dianhydride monomers in addition to 3-functional monomers based trimellitic acid), such that polymers or co-polymers can be similarly modified according to the principles and methods taught herein. Such compositions are specifically included in the present invention and it will be apparent to the artisan that the methods described herein for polymers or co-polymers of formulae M4 can also be applied to more complex mixed imide amide polymers or co-polymers that are difficult to represent formulaically.

In certain embodiments, the polyamide imide-based OSN membranes of the present invention are characterized in that they contain less than 100 mol of free amine per gram of polyamide imide. In certain embodiments, the PAI-based OSN membranes of the present invention are characterized in that they contain less than 75 µmol, less than 50 µmol, less than 40 µmol, less than 30 µmol, less than 25 µmol, less than 20 µmol, less than 15 µmol, less than 10 µmol, less than 5 µmol, or less than 1 µmol of free amine per gram of PAI. In certain embodiments, the PAI-based OSN membranes of the present invention are characterized in that they contain less than 500 nmol of free amine per gram of PAI. In certain embodiments, the PAI-based OSN membranes of the present invention are characterized in that they contain less than 400 nmol, less than 300 nmol, less than 250 nmol, less than 200 nmol, less than 150 nmol, less than 100 nmol, less than 50 nmol, less than 40 nmol, less than 30 nmol, less than 20 nmol, less than 10 nmol, less than 5 nmol, or less than 1 nmol of free amine per gram of PAI.

In certain embodiments, the PAI-based OSN membranes of the present invention are characterized in that they are essentially free of detectable free amine. In certain embodiments, they are essentially free of detectable free amine as determined by colorimetric analysis: for example by optical absorption or fluorescence detection after derivatization. Suitable derivatizations include, but are not limited to: reaction with ninhydrin, 1,8-Diazafluoren-9-one (DFO), 1,2-Indanedione, 5-methylthioninhydrin (5-MTN), or similar reagents. In certain embodiments, the present invention provides PAI-based OSN membranes characterized in that they give a negative ninhydrin test. In certain embodiments, the present invention provides polyamide imide-based OSN membranes characterized in that they give a negative DFO test. In certain embodiments, the present invention provides PAI-based OSN membranes characterized in that they give a negative 5-MTN test. In certain embodiments, the present invention provides PAI-based OSN membranes characterized in that they give a negative test with 1,2-indanedione.

In certain embodiments, the PAI-based OSN membranes of the present invention are characterized in that they are essentially free of detectable free amine by spectrometric analysis.

In certain embodiments, provided is a nanofiltration membrane comprising a co-polymer, the co-polymer comprising a monomer of Formula M4 and one or more of a monomer of Formula M5 and a group of Formula M6:

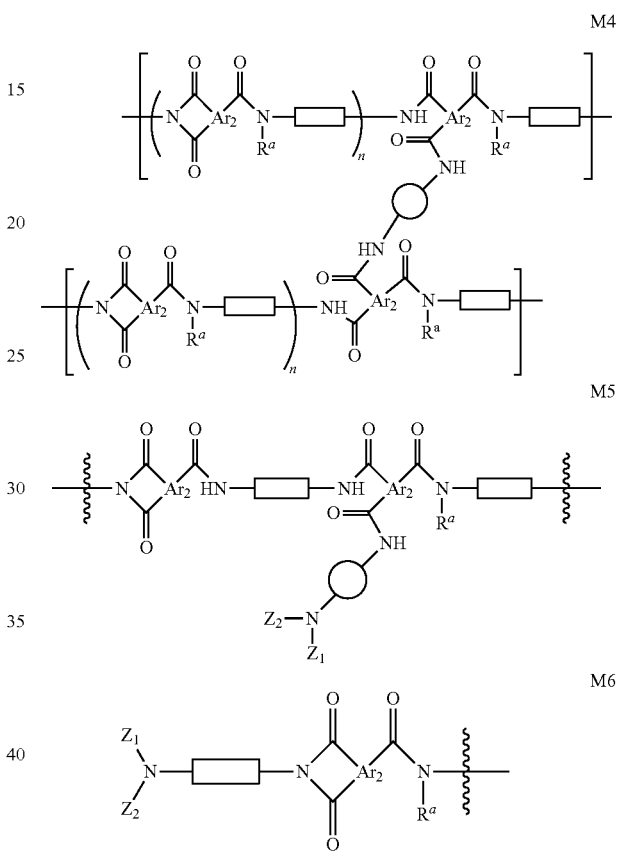

wherein:
each $Ar_2$ is a trivalent aromatic moiety;
each

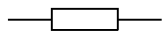

represents a bivalent linker and may be the same or different at each occurrence in the co-polymer;
each

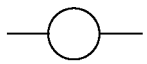

represents a bivalent linker and may be the same or different at each occurrence in the co-polymer;
n is any integer up to about 100,000;
$Z_1$ is —H, aliphatic, acyl, or aryl;
$Z_2$ is selected from the group consisting of: aliphatic, aryl, acyl, —C(O)OR$^x$, —SO$_2$R$^x$, and —C(O)NHR$^x$;

where $Z_1$ and $Z_2$ may optionally be taken together to form a ring;

$R^x$ is an optionally substituted aliphatic or optionally substituted aromatic group; and $R^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl.

In certain embodiments, provided is a nanofiltration membrane comprising a co-polymer, the co-polymer comprising the monomer of Formula M4 and the monomer of Formula M5. In certain embodiments, provided is a nanofiltration membrane comprising a co-polymer, the co-polymer comprising the monomer of Formula M4 and the group of Formula M6.

In certain embodiments of the nanofiltration membrane, the co-polymer comprises a monomer of Formulae M5a to M5j:

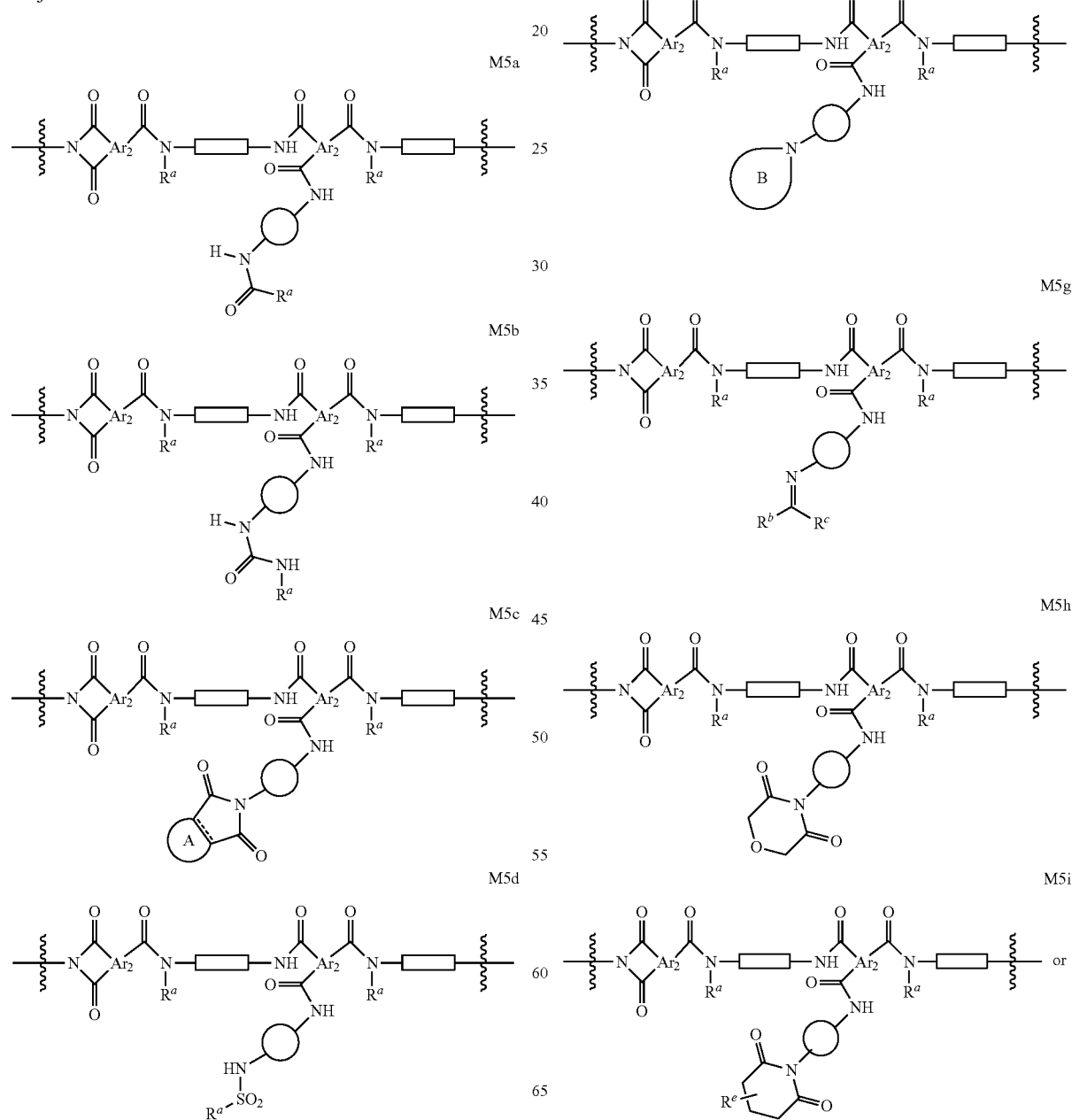

-continued

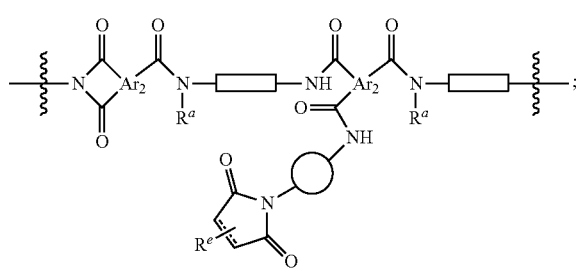

M5j wherein:
- $R^e$ is one or more moieties selected from the group consisting of: —H, halogen, —OR, —NR$_2$, —SR, —CN, —SO$_2$R, —SOR, —CO$_2$R, —C(O)R, —OC(O)R, SO$_2$NR$_2$; —CNO, —NRSO$_2$R, —N$_3$, —SiR$_3$; or an optionally substituted group selected from the group consisting of C$_{1-20}$ aliphatic; C$_{1-20}$ heteroliphtic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur
- R is H, or optionally substituted aliphatic or optionally substituted aromatic;
- ring A is an optionally substituted aryl ring or an optionally substituted saturated or partially unsaturated mono- or polycyclic ring optionally containing one or more heteroatoms selected from the group consisting of nitrogen, oxygen, and sulfur; and
- ring B represents an optionally substituted 5- or 6-membered saturated, partially unsaturated or aromatic ring optionally containing one or more additional heteroatoms, selected from the group consisting of nitrogen, oxygen, and sulfur, which may be part of a larger fused ring system.

In certain embodiments, provided is a nanofiltration membrane comprising a co-polymer, the co-polymer comprising the monomer of Formula M4 and the monomer of Formula M5a. In certain embodiments, provided is a nanofiltration membrane comprising a co-polymer, the co-polymer comprising the monomer of Formula M4 and the monomer of Formula M5b. In certain embodiments, provided is a nanofiltration membrane comprising a co-polymer, the co-polymer comprising the monomer of Formula M4 and the monomer of Formula M5c. In certain embodiments, provided is a nanofiltration membrane comprising a co-polymer, the co-polymer comprising the monomer of Formula M4 and the monomer of Formula M5d. In certain embodiments, provided is a nanofiltration membrane comprising a co-polymer, the co-polymer comprising the monomer of Formula M4 and the monomer of Formula M5e. In certain embodiments, provided is a nanofiltration membrane comprising a co-polymer, the co-polymer comprising the monomer of Formula M4 and the monomer of Formula M5f. In certain embodiments, provided is a nanofiltration membrane comprising a co-polymer, the co-polymer comprising the monomer of Formula M4 and the monomer of Formula M5g. In certain embodiments, provided is a nanofiltration membrane comprising a co-polymer, the co-polymer comprising the monomer of Formula M4 and the monomer of Formula M5h. In certain embodiments, provided is a nanofiltration membrane comprising a co-polymer, the co-polymer comprising the monomer of Formula M4 and the monomer of Formula M5i. In certain embodiments, provided is a nanofiltration membrane comprising a co-polymer, the co-polymer comprising the monomer of Formula M4 and the monomer of Formula M5j. In certain embodiments, provided is a nanofiltration membrane comprising a co-polymer, the co-polymer comprising the monomer of Formula M4 and the monomer of Formula M5h. In certain embodiments, provided is a nanofiltration membrane comprising a co-polymer, the co-polymer comprising the monomer of Formula M4 and the monomer of Formula M5i. In certain embodiments, provided is a nanofiltration membrane comprising a co-polymer, the co-polymer comprising the monomer of Formula M4 and the monomer of Formula M5j.

In certain embodiments of the nanofiltration membrane, the co-polymer comprises a monomer of Formula M4 and a monomer of Formula M13:

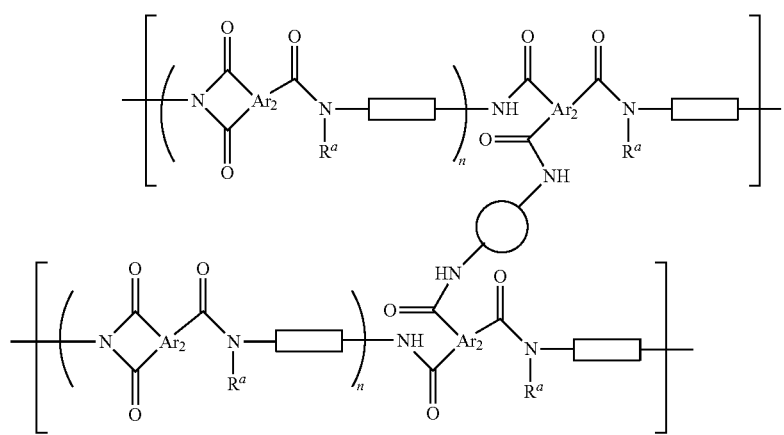

M4

-continued

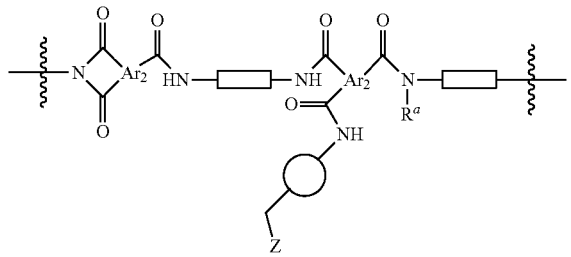

M13 wherein:
each $Ar_2$ is a trivalent aromatic moiety;
each

represents a bivalent linker and may be the same or different at each occurrence is the cop-polymer;
each

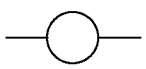

represents a bivalent linker and may be the same or different at each occurrence in the co-polymer;
n is any integer up to about 100,000;
Z is a functional group that does not contain a nitrogen atom; and
$R^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl.

In certain embodiments of the nanofiltration membrane, the co-polymer comprises a monomer of Formulae M13a to M13d:

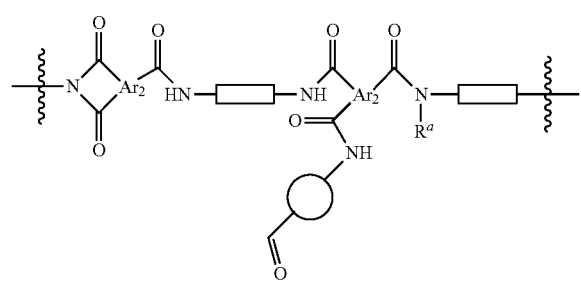

M13a

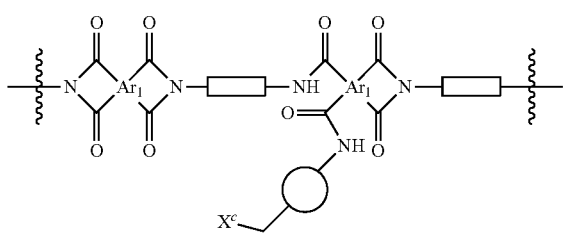

M13b

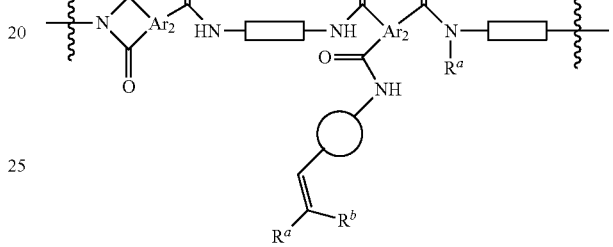

M13c

M13d wherein
$X^c$ is Cl, Br or I.

In certain embodiments of the nanofiltration membrane, the co-polymer comprises a monomer of Formula M4 and a monomer of Formula M13a. In certain embodiments of the nanofiltration membrane, the co-polymer comprises a monomer of Formula M4 and a monomer of Formula M13b. In certain embodiments of the nanofiltration membrane, the co-polymer comprises a monomer of Formula M4 and a monomer of Formula M13c. In certain embodiments of the nanofiltration membrane, the co-polymer comprises a monomer of Formula M4 and a monomer of Formula M13d.

In certain embodiments, provided is a nanofiltration membrane comprising a co-polymer, the co-polymer comprising a monomer of Formulae M7, M8 and/or M9, and one or more of a monomer of Formulae M10 and M11, and a group of Formulae M12 and M6:

M7
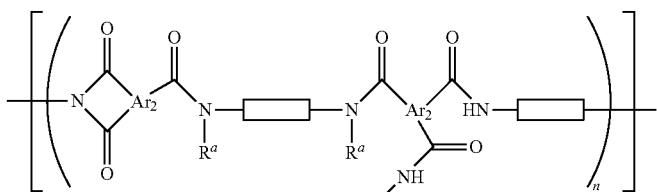
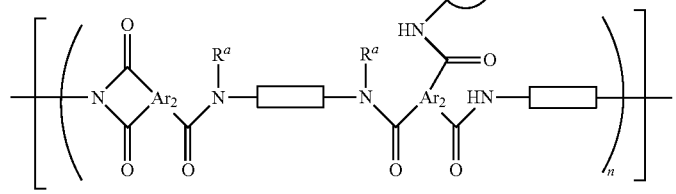
and/or
M8
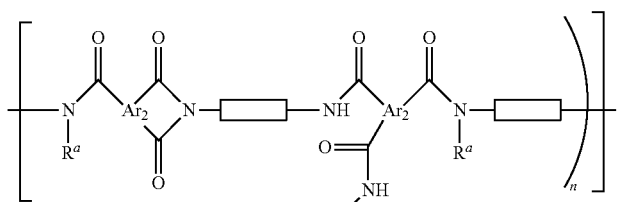
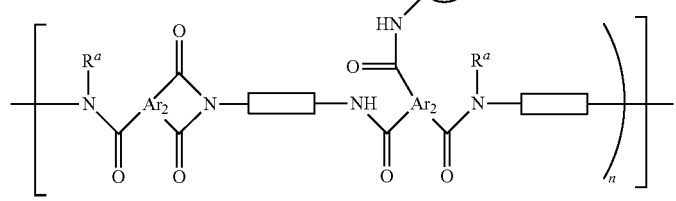
and/or
M9
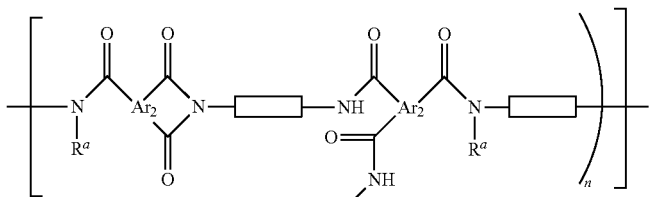
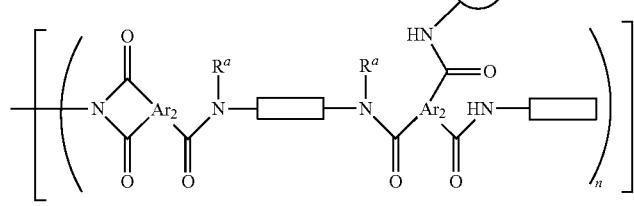
M10
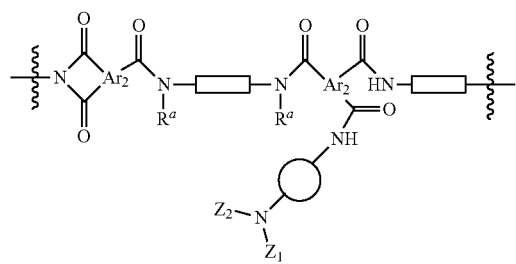
and/or
M11
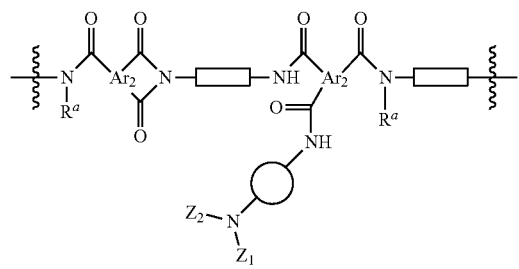
and/or

M12

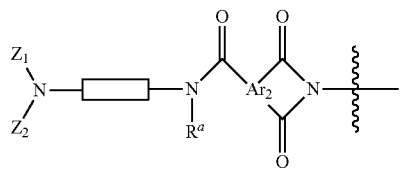

and/or

M6

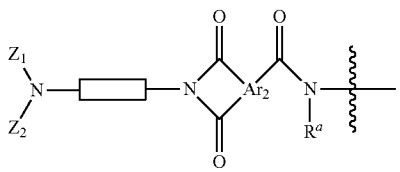

wherein:
each $Ar_2$ is a trivalent aromatic moiety;
each

represents a bivalent linker and may be the same or different at each occurrence in the co-polymer.
each

represents a bivalent linker and may be the same or different at each occurrence in the co-polymer;
n is any integer up to about 100,000;
$Z_1$ is —H, aliphatic, acyl, or aryl;
$Z_2$ is selected from the group consisting of: aliphatic, aryl, acyl, —C(O)OR$^x$, —SO$_2$R$^x$, and —C(O)NHR$^x$;
where $Z_1$ and $Z_2$ may optionally be taken together to form a ring;
$R^x$ is an optionally substituted aliphatic or optionally substituted aromatic group; and
$R^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl.

In certain embodiments of the nanofiltration membrane, the co-polymer comprises a monomer of Formula M10. In certain embodiments of the nanofiltration membrane, the co-polymer comprises a monomer of Formula M11. In certain embodiments of the nanofiltration membrane, the co-polymer comprises a group of Formula M12. In certain embodiments of the nanofiltration membrane, the co-polymer comprises a group of Formula M6.

In certain embodiments of the nanofiltration membrane, each $Ar_2$ is independently selected from the group consisting of:

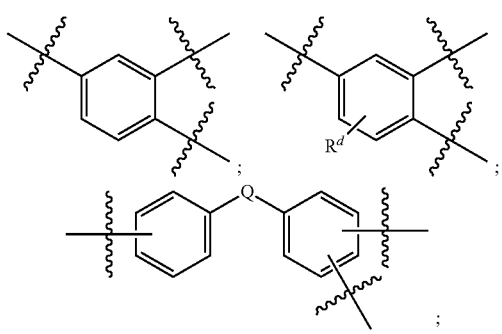

and
Q is selected from the group consisting of:

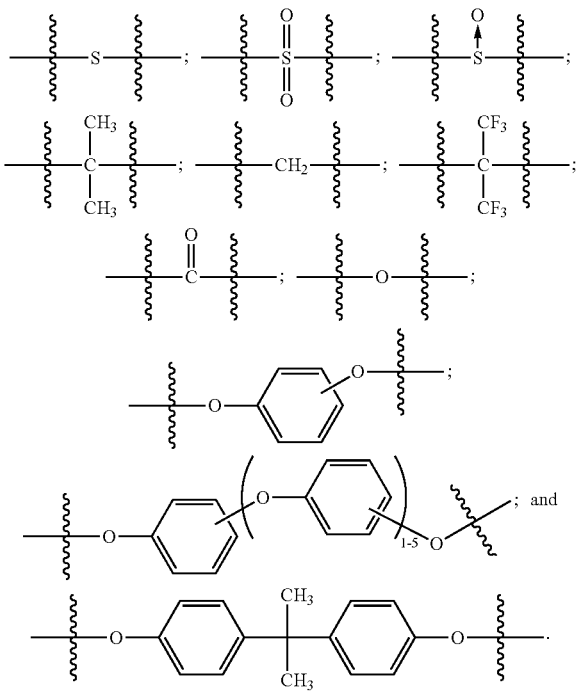

In certain embodiments of the nanofiltration membrane, each

is independently a bivalent $C_{2-20}$ aliphatic group, bivalent aromatic group, or derives from a bivalent diamine group

In certain embodiments of the nanofiltration membrane, each

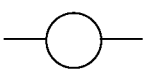

is —$CH_2CH_2$—; —$CH_2CH_2CH_2$—; —$CH_2(CH_2)_2CH_2$—; —$CH_2(CH_2)_3CH_2$—; —$CH_2(CH_2)_4CH_2$—; —$CH_2(CH_2)_6CH_2$—; —$CH_2(CH_2)_8CH_2$—; —$CH_2(CH_2)_{10}CH_2$—; —$CH_2(CH_2)_{12}CH_2$—; —$CH_2(CH_2)_{14}CH_2$—; or —$CH_2(CH_2)_{16}CH_2$—.

In certain embodiments of the nanofiltration membrane, each

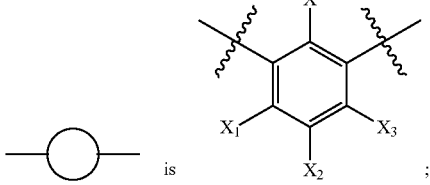

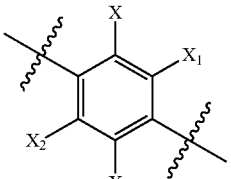

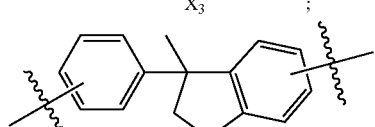

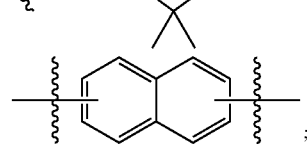

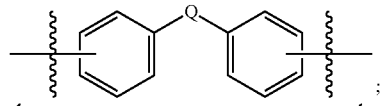

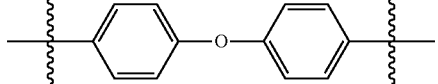

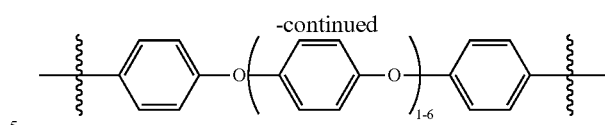

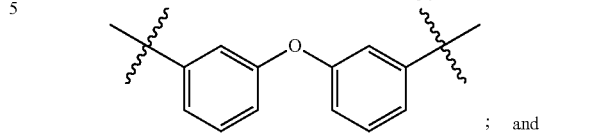

; and

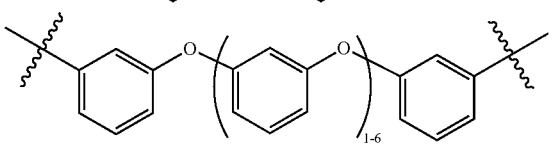

each X, $X_1$, $X_2$ and $X_3$ is independently hydrogen, halogen, or an optionally substituted moiety selected from the group consisting of halogen, aliphatic, alkoxy, phenoxy, aryl, and phenyl; and Q is selected from the group consisting of:

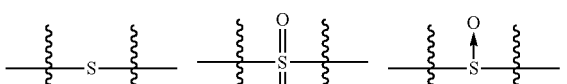

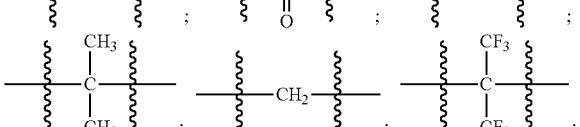

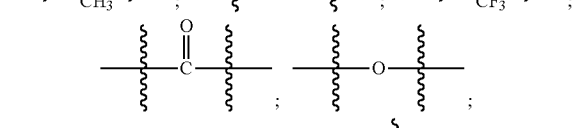

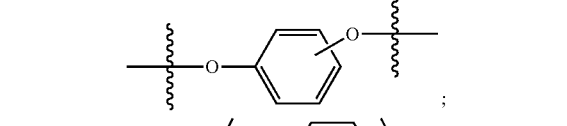

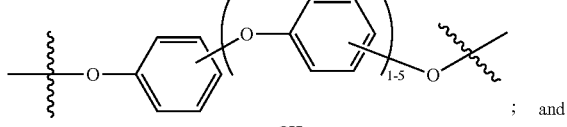

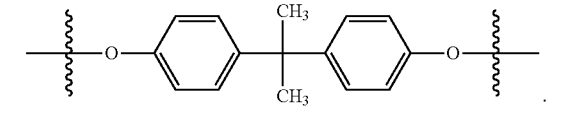

In certain embodiments of the nanofiltration membrane, each

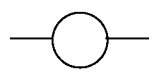

derives from a bivalent diamine group,

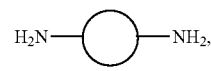

selected from the group consisting of:

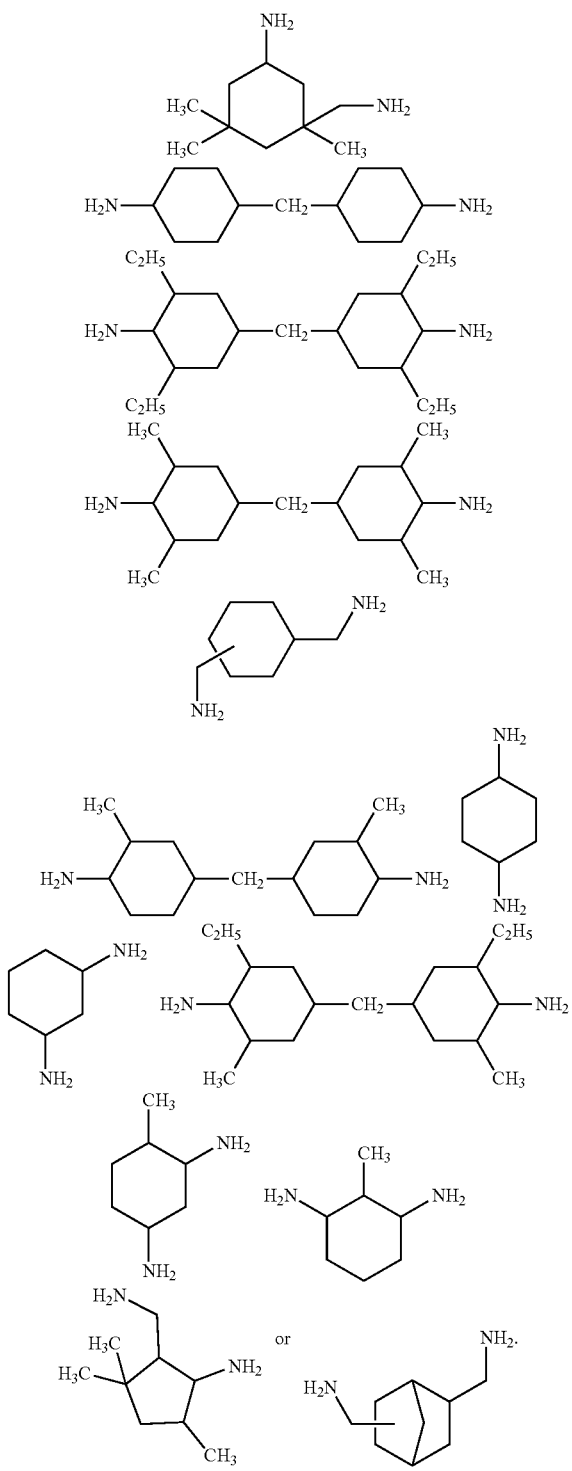

Methods of Manufacturing and Modifying OSN Membranes

In another aspect, the present invention provides methods of making chemically-resistant OSN membranes. As described above, existing cross-linked OSN membranes are incompatible with certain classes of reactive chemicals. The present invention provides methods to modify such membranes after crosslinking to improve their compatibility with reactive chemical compounds.

Methods of Producing Polysiloxane OSN Membranes with Improved Chemical Compatibility In certain embodiments, the present invention provides methods of producing cross linked polysiloxane OSN membranes with reduced chemical activity. In certain embodiments such methods comprise treating a polysiloxane composition to induce crosslinking, and then treating the crosslinked composition with a silylating reagent. In certain embodiments, the silylating reagent comprises a silyl halide. In certain embodiments, the silylating reagent comprises silyl amide. In certain embodiments, the silylating reagent comprises silyl amine.

In certain embodiments, the OSN membrane comprises polydimethylsiloxane (PDMS) and the method comprises crosslinking the polymer or co-polymer by a physical process selected from thermal treatment, irradiation, and a combination of two or more of these followed by treatment with a silylating agent selected from silyl halide, silyl amide, and silyl amine. In certain embodiments, step of silylating the crosslinked membrane comprises treating with a reagent of formula $R_3SiX^a$ where R is any aliphatic or aryl group and $X^a$ is a halogen. In certain embodiments, step of silylating the crosslinked membrane comprises treating with a reagent of formula $Me_3SiCl$.

In certain embodiments, the step of cross-linking the membrane and the step of silylating are both performed at the sight of membrane manufacture. In other embodiments, the cross linking is performed during manufacture while the step of silylating is performed at a later time prior to using the membrane. In certain embodiments the step of cross linking is performed by the membrane manufacturer, while the step of silylating is performed by the membrane user.

Methods of Producing polyimide OSN Membranes with Improved Chemical Compatibility In certain embodiments, the present invention provides methods of producing cross linked polyimide OSN membranes with reduced chemical activity. In certain embodiments such methods comprise treating a polyimide composition with a polyamine to induce crosslinking, and then treating the crosslinked composition with a reagent reactive toward primary and secondary amines.

In certain embodiments, the reagent reactive toward primary and secondary amines is selected from the group consisting of: acid halides, acid anhydrides, isocyanates, phthalic anhydrides, optionally substituted succinic anhydride, optionally substituted maleic anhydride, optionally substituted glutaric anhydride, diglycolic acid anhydride, sulfonyl halide, sulfonyl anhydride, optionally substituted alkyl chlorformate, optionally substituted aryl chloroformate, ketone, aldehyde, ketal, acetal, multiply reactive species that convert primary amines to heterocyclic compounds, and combinations of any two or more of these.

In certain embodiments, methods of the present invention comprise the step of treating a polyimide composition with a polyamine to provide a crosslinked polymer or co-polymer composition comprising polymer or co-polymer of formula M4B further containing segments having formula:

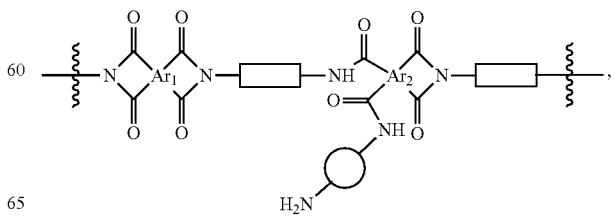

and then treating the crosslinked polymer or co-polymer composition with one or more reagents selected from the group consisting of: acid halides, acid anhydrides, isocyanates, phthalic anhydrides, optionally substituted succinic anhydride, optionally substituted maleic anhydride, optionally substituted glutaric anhydride, diglycolic acid anhydride, sulfonyl halide, sulfonyl anhydride, optionally substituted alkyl chloroformate, optionally substituted aryl chloroformate, ketone, aldehyde, ketal, acetal, and multiply reactive species that convert primary amines to heterocyclic compounds, to provide a passivated crosslinked polymer or co-polymer composition comprising segments of formula M2:

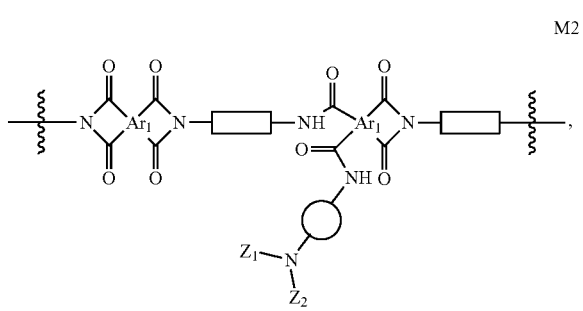

M2 where each of $Ar_1$, n,

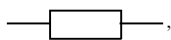

$Z_1$, $Z_2$, and

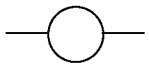

is as defined above and in the classes and subclasses herein.

In certain embodiments, methods of the present invention comprise the steps of treating a polyimide composition with a polyamine to provide a crosslinked polymer or co-polymer composition comprising polymer or co-polymer chains of formula M1 and then treating the crosslinked polymer or co-polymer composition with an acid halides or acid anhydrides to provide a composition containing segments of formula M2a. In certain embodiments, the resulting composition contains segments of any of formulae M2a-1 through M2a-8.

In certain embodiments, methods of the present invention comprise the steps of treating a polyimide composition with a polyamine to provide a crosslinked polymer or co-polymer composition comprising polymer or co-polymer chains of formula M1 and then treating the crosslinked polymer or co-polymer composition with an isocyanate to provide a composition containing segments of formula M2b. In certain embodiments, the resulting composition contains segments of any of formulae M2b-1 through M2b-10.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with a cyclic anhydride of formula

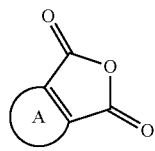

(or the corresponding diacid halide) to provide a composition containing segments of formula M2c. In certain embodiments, the resulting composition contains segments of any of formulae M2c-1 through M2c-8.

In certain embodiments, methods of the present invention comprise the steps of treating the polyimide-based OSN composition with a polyamine to provide crosslinked polymer or co-polymer composition comprising polymer or co-polymer chains of formula M1 and then treating crosslinked polymer or co-polymer composition with a sulfonyl halide or sulfonic acid anhydride to provide a composition containing segments of formula M2d. In certain embodiments, the resulting composition contains segments of any of formulae M2d-1 through M2d-10.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with a chloroformate to provide a composition containing segments of formula M2e. In certain embodiments, the resulting composition contains segments of any of formulae M2e-1 through M2e-8.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with a multiply reactive species that convert primary amines to heterocyclic compounds to provide a composition containing segments of formula M2f. In certain embodiments, the resulting composition contains segments of any of formulae M2f-1 through M2f-14.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with a ketone, aldehyde, ketal, hemiketal, acetal, or hemiacetal to provide a composition containing segments of formula M2g. In certain embodiments, the resulting composition contains segments of any of formulae M2g-1 through M2g-2.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with dyglycolic acid anhydride (DGA) to provide a composition containing segments of formula M2h.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with an optionally substituted glutaric anhydride or glutaric acid dihalide to provide a composition containing segments of formula M2i.

In certain embodiments, methods of the present invention comprise the steps of treating a polyimide-based OSN composition with a polyamine to provide a crosslinked polymer or co-polymer composition comprising polymer or co-polymer chains of formula M1 and then treating the crosslinked polymer or co-polymer composition with an optionally substituted maleic anhydride, maleic acid dihalide, succinic anhydride or succinic acid dihalide, to provide a composition containing segments of formula M2j. In certain embodiments, the resulting composition contains segments of any of formulae M2j-1 through M2j-8.

For any of the methods above, the polymer or co-polymer M1 and segments M2a through M2j-8 encompass each or any of the structures described above in the membrane composition section according to the variable definitions therein and the various classes and subclasses thereof.

In certain embodiments, methods of the present invention comprise the steps of treating a polyimide-based OSN composition with a polyamine to provide a crosslinked polymer or co-polymer composition comprising polymer or co-polymer chains of formula M1 further containing segments having formula:

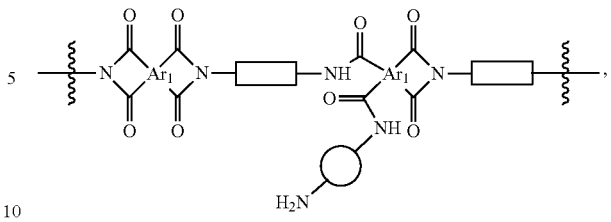

and then treating the crosslinked polymer or co-polymer composition with one or more reagents which result in the conversion of the —NH$_2$ moiety to a non-nitrogen containing functional group selected from the group consisting of: aldehyde, halogen, and alkene.

Where each of Ar$_1$, n,

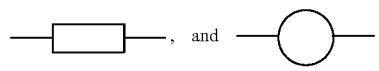

is as defined above and in the classes and subclasses herein.

Methods of Producing Polyamide Imide OSN Membranes with Improved Chemical Compatibility In certain embodiments, the present invention provides methods of producing cross linked polyamide imide OSN membranes with reduced chemical activity. In certain embodiments such methods comprise treating a polyamide imide-based OSN composition with a polyamine to induce

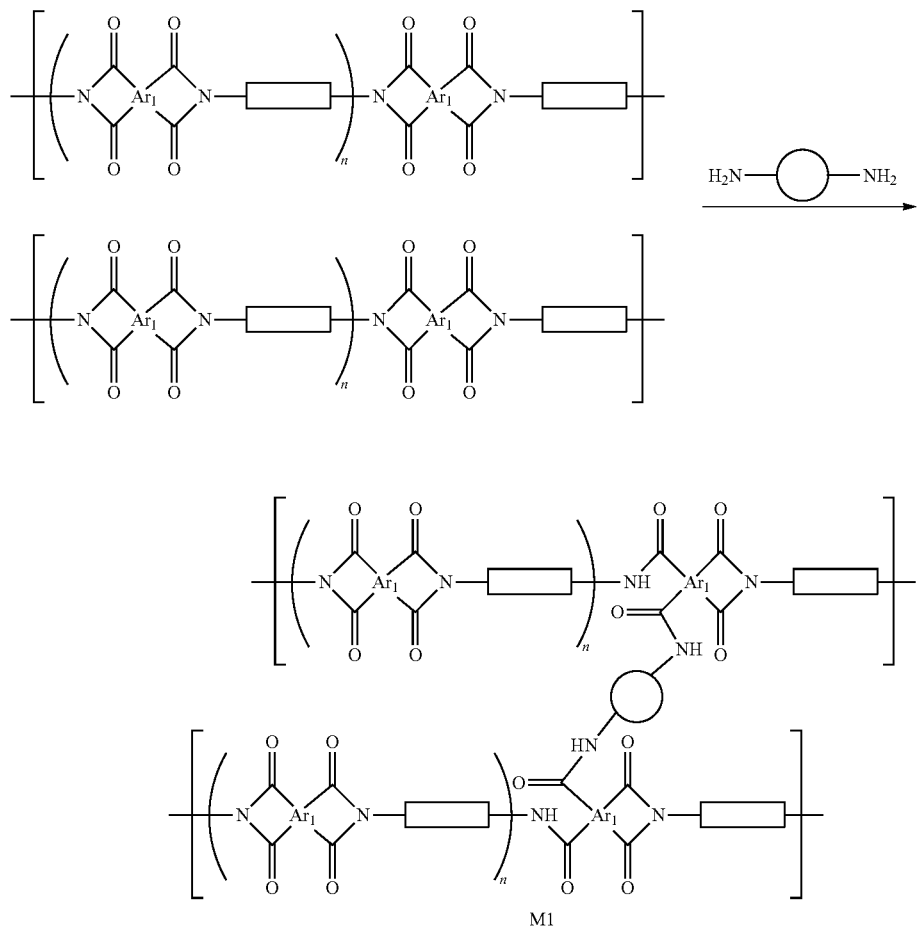

M1 crosslinking, and then treating the crosslinked composition with a reagent reactive toward primary and secondary amines.

In certain embodiments, the reagent reactive toward primary and secondary amines is selected from the group consisting of: acid halides, acid anhydrides, isocyanates, phthalic anhydrides, optionally substituted succinic anhydride, optionally substituted maleic anhydride, optionally substituted glutaric anhydride, diglycolic acid anhydride, sulfonyl halide, sulfonyl anhydride, optionally substituted alkyl chloroformate, optionally substituted aryl chloroformate, ketone, aldehyde, ketal, acetal, multiply reactive species that convert primary amines to heterocyclic compounds, and combinations of any two or more of these.

In certain embodiments, methods of the present invention comprise the step of treating a polyamide imide-based OSN composition with a polyamine to provide a crosslinked polymer or co-polymer composition comprising polymer or co-polymer of formula M4:

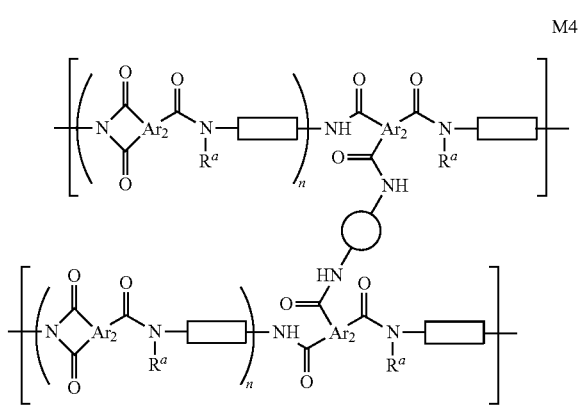

M4 further containing segments having formula:

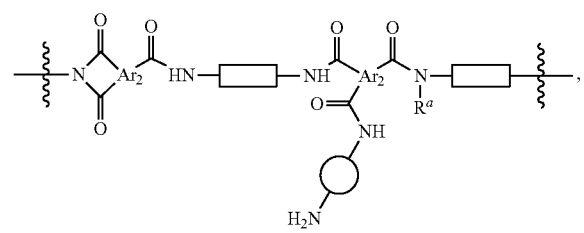

and then treating the crosslinked polymer or co-polymer composition with one or more reagents selected from the group consisting of: acid halides, acid anhydrides, isocyanates, phthalic anhydrides, optionally substituted succinic anhydride, optionally substituted maleic anhydride, optionally substituted glutaric anhydride, diglycolic acid anhydride, sulfonyl halide, sulfonyl anhydride, optionally substituted alkyl chloroformate, optionally substituted aryl chloroformate, ketone, aldehyde, ketal, acetal, and multiply reactive species that convert primary amines to heterocyclic compounds, to provide a passivated crosslinked polymer or co-polymer composition comprising segments of formula M5:

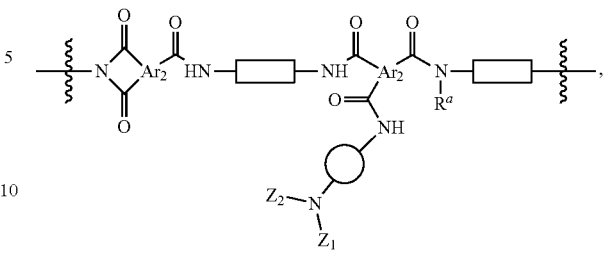

M5 where each of $Ar_1$, n

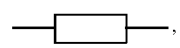

$R^a$, $Z_1$, $Z_2$, and

is as defined above and in the classes and subclasses herein.

In certain embodiments, methods of the present invention comprise the steps of treating a polyamide imide-based OSN composition with a polyamine to provide a crosslinked polymer or co-polymer composition comprising polymer or co-polymer chains of formula M5 and then treating the crosslinked polymer or co-polymer composition with an acid halide or acid anhydride to provide a composition containing segments of formula M5a. In certain embodiments, the resulting composition contains segments of any of formulae M5a-1 through M5a-8.

In certain embodiments, methods of the present invention comprise the steps of treating a polyamide imide-based OSN composition with a polyamine to provide crosslinked polymer or co-polymer composition comprising polymer or co-polymer chains of formula M5 and then treating the crosslinked polymer or co-polymer composition with an isocyanate to provide a composition containing segments of formula M5b. In certain embodiments, the resulting composition contains segments of any of formulae M5b-1 through M5b-10.

In certain embodiments, methods of the present invention comprise the steps of treating a polyamide imide-based OSN composition with a polyamine to provide a crosslinked polymer or co-polymer composition comprising polymer or co-polymer chains of formula M5 and then treating the crosslinked polymer or co-polymer composition with a cyclic anhydride of formula

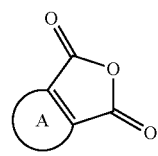

(or a corresponding diacid halide) to provide a composition containing segments of formula M5c. In certain embodiments, the resulting composition contains segments of any of formulae M5c-1 through M5c-8.

In certain embodiments, methods of the present invention comprise the steps of treating a polyamide imide-based OSN composition with a polyamine to provide a crosslinked polymer or co-polymer composition comprising polymer or co-polymer chains of formula M5 and then treating the crosslinked polymer or co-polymer composition with a sufonyl halide or sulfonic acid anhydride to provide a composition containing segments of formula M5d. In certain embodiments, the resulting composition contains segments of any of formulae M5d-1 through M5d-10.

In certain embodiments, methods of the present invention comprise the steps of treating a polyamide imide-based OSN composition with a polyamine to provide a crosslinked polymer or co-polymer composition comprising polymer or co-polymer chains of formula M5 and then treating the crosslinked polymer or co-polymer composition with a chloroformate to provide a composition containing segments of formula M5e. In certain embodiments, the resulting composition contains segments of any of formulae M5e-1 through M5e-8.

In certain embodiments, methods of the present invention comprise the steps of treating a polyamide imide-based OSN composition with a polyamine to provide crosslinked polymer or co-polymer composition comprising polymer or co-polymer chains of formula M5 and then treating crosslinked polymer or co-polymer composition with a multiply reactive species that convert primary amines to heterocyclic compounds to provide a composition containing segments of formula M5f. In certain embodiments, the resulting composition contains segments of any of formulae M5f-1 through M5f-14. In certain embodiments, methods of the present invention comprise the steps of treating a polyamide imide composition with a polyamine to provide crosslinked polymer or co-polymer composition comprising polymer or co-polymer chains of formula M5 and then treating cross-linked polymer or co-polymer composition with a ketone, aldehyde, ketal, hemiketal, acetal, or hemiacetal to provide a composition containing segments of formula M5g. In certain embodiments, the resulting composition contains segments of any of formulae M5g-1 through M5g-2.

In certain embodiments, methods of the present invention comprise the steps of treating a polyamide imide composition with a polyamine to provide crosslinked polymer or co-polymer composition comprising polymer or co-polymer chains of formula M5 and then treating crosslinked polymer or co-polymer composition with dyglycolic acid anhydride (DGA) to provide a composition containing segments of formula M5h.

In certain embodiments, methods of the present invention comprise the steps of treating a polyamide imide composition with a polyamine to provide crosslinked polymer or co-polymer composition comprising polymer or co-polymer chains of formula M5 and then treating crosslinked polymer or co-polymer composition with an optionally substituted glutaric anhydride or glutaric acid dihalide to provide a composition containing segments of formula M5i.

In certain embodiments, methods of the present invention comprise the steps of treating a polyamide imide composition with a polyamine to provide a crosslinked polymer or co-polymer composition comprising polymer or co-polymer chains of formula M5 and then treating the crosslinked polymer or co-polymer composition with an optionally substituted maleic anhydride, maleic acid dihalide, succinic anhydride or succinic acid dihalide, to provide a composition containing segments of formula M5j. In certain embodiments, the resulting composition contains segments of any of formulae M5j-1 through M5j-8.

For any of the methods above, the polymer or co-polymer M5 and segments M5a through M5j-8 encompass each or any of the structures described above in the polyamide imide membrane composition section according to the variable definitions therein and the various classes and subclasses thereof.

In certain embodiments, methods of the present invention comprise the steps of treating a polyamide imide composition with a polyamine to provide a crosslinked polymer or co-polymer composition comprising polymer or co-polymer chains of formula M4

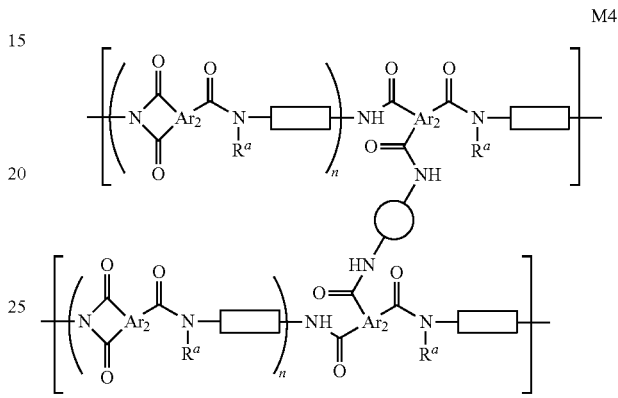

further containing segments having formula:

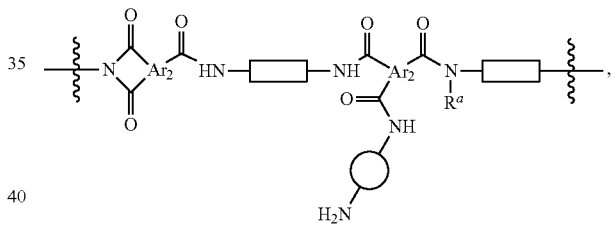

and then treating the crosslinked polymer or co-polymer composition with one or more reagents which result in the conversion of the —NH$_2$ moiety to a non-nitrogen containing functional group selected from the group consisting of: aldehyde, halogen, and alkene.

Where each of Ar$_2$, R$^a$, n,

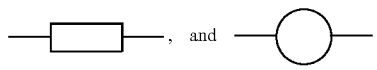

is as defined above and in the classes and subclasses herein.

Methods of Using the Modified OSN Membranes

In another aspect, the present disclosure encompasses methods for the production of acrylates from epoxide feedstocks in a continuous-flow process utilizing the novel nanofiltration membranes described above.

In general, processes of the invention include the step of carbonylating an epoxide feedstock in the presence of a homogenous carbonylation catalyst to yield a beta lactone-containing process stream. This beta lactone-containing process stream is then contacted with any of the passivated OSN nanofiltration membrane as described hereinabove to produce two streams: a permeate stream and a retentate stream wherein the permeate stream contains beta lactone and the retentate stream contains a higher concentration of the homogenous catalyst than the permeate stream.

In certain embodiments, the retentate stream is treated as a catalyst recycling stream and is returned to the process where it is contacted with additional epoxide and carbon monoxide.

In certain embodiments, the carbonylation step is performed in the presence of an organic solvent by contacting the epoxide with carbon monoxide in the presence of a homogenous carbonylation catalyst.

Numerous carbonylation catalysts known in the art are suitable for (or can be adapted to) this step. For example, in certain embodiments, the carbonylation step is performed with a metal carbonyl-Lewis acid catalyst such as those described in U.S. Pat. No. 6,852,865. In other embodiments, the carbonylation step is performed with one or more of the carbonylation catalysts disclosed in U.S. patent application Ser. Nos. 10/820,958; and 10/586,826. In other embodiments, the carbonylation step is performed with one or more of the catalysts disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In certain embodiments, the carbonylation catalyst includes a metal carbonyl compound. In some embodiments, the metal carbonyl compound has the general formula $[QM_y(CO)_w]^{x-}$, where:

Q is any ligand and need not be present;
M is a metal atom;
y is an integer from 1 to 6 inclusive;
w is a number selected such as to provide the stable metal carbonyl; and
x is an integer from −3 to +3 inclusive.

In certain embodiments where the metal carbonyl compound has the formula $[QM_y(CO)_w]^{x-}$, M is selected from the group consisting of Ti, Cr, Mn, Fe, Ru, Co, Rh, Ni, Pd, Cu, Zn, Al, Ga and In. In certain embodiments, M is Co.

In certain embodiments, the carbonylation catalyst further includes a Lewis acidic component. In some embodiments, the carbonylation catalyst includes an anionic metal carbonyl complex and a cationic Lewis acidic component. In certain embodiments, the metal carbonyl complex includes a carbonyl cobaltate and the Lewis acidic co-catalyst includes a metal-centered cationic Lewis acid.

In certain embodiments, the metal-centered Lewis acid is a metal complex of formula $[M'(L)_b]^{c+}$, where:

M' is a metal;
each L is a ligand;
b is an integer from 1 to 6 inclusive;
c is 1, 2, or 3; and
where, if more than one L is present, each L may be the same or different.

In some embodiments where the metal-centered Lewis acid is a metal complex of formula $[M'(L)_b]^{c+}$, M' is selected from the group consisting of: a transition metal, a group 13 or 14 metal, and a lanthanide. In certain embodiments, M' is a transition metal or a group 13 metal. In certain embodiments, M' is selected from the group consisting of aluminum, chromium, indium, and gallium. In certain embodiments, M' is aluminum. In certain embodiments, M' is chromium.

In certain embodiments, the metal-centered Lewis-acidic component of the carbonylation catalyst includes a dianionic tetradentate ligand. In certain embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand.

In certain embodiments, the carbonylation catalyst includes a carbonyl cobaltate in combination with an aluminum porphyrin compound.

In certain embodiments, the carbonylation catalyst includes a carbonyl cobaltate in combination with a chromium porphyrin compound.

In certain embodiments, the carbonylation catalyst includes a carbonyl cobaltate in combination with a chromium salen compound. In certain embodiments, the carbonylation catalyst includes a carbonyl cobaltate in combination with a chromium salophen compound.

In certain embodiments, the carbonylation catalyst includes a carbonyl cobaltate in combination with an aluminum salen compound. In certain embodiments, the carbonylation catalyst includes a carbonyl cobaltate in combination with an aluminum salophen compound.

Solvents suitable for the process comprise organic solvents. In certain embodiments, the solvent comprises an ether. In certain embodiments, the solvent comprises one or more of THF, 1,4-dioxane, diethyl ether, tertiary butyl dimethyl ether, diphenyl ether, glyme, diglyme, higher glymes, and the like. In certain embodiments, the solvent comprises THF. In certain embodiments, the solvent comprises 1,4-dioxane.

In certain embodiments, the solvent may be chosen from organic solvents including, but not limited to, dimethylformamide, N-methyl pyrrolidone, tetrahydrofuran, toluene, xylene, diethyl ether, methyl-tert-butyl ether, acetone, methylethyl ketone, methyl-iso-butyl ketone, butyl acetate, ethyl acetate, dichloromethane, and hexane, and mixtures of any two or more of these. In general polar aprotic solvents or hydrocarbons are suitable.

In certain embodiments, the catalyst, starting materials, and products are all completely soluble in the organic solvent under the process conditions of the carbonylation step. In other embodiments, one or more of the catalyst, the starting materials, or the products are insoluble or only partially soluble in the organic solvent. In certain embodiments, the carbonylation catalyst is soluble in the organic solvent.

In certain embodiments, one or more additional solvents may be present in the process stream of the first step. In these embodiments, the nanofiltration membrane is stable in the solvent mixture of the process stream, although the nanofiltration membrane may not be stable in one or more of the additional solvents at higher concentrations. In these embodiments, the lactone-containing stream separated in a subsequent step may contain lactone along with one or more of the additional solvents.

In the carbonylation step of the process, there should be enough carbon monoxide present to effect efficient conversion of the epoxide starting material. This can be ensured by performing the reaction under a superatmospheric pressure of carbon monoxide. In certain embodiments, the carbonylation step is performed at a pressure in the range from about 50 psi (350 kPa) to about 5000 psi (35 MPa). In certain embodiments, the carbonylation step is performed at a pressure from about 50 psi (350 kPa) to about 1000 psi (7 MPa). In certain embodiments, the carbonylation step is performed at a pressure from about 50 psi (350 kPa) to about 500 psi (3.5 MPa). In certain embodiments, the carbonylation step is performed at a pressure from about 100 psi (700 kPa) to about 400 psi (2.8 MPa). In certain embodiments, the carbonylation step is performed at a pressure of about 200 psi (1.4 MPa). In certain embodiments, the carbonylation step is performed under an atmosphere having a partial pressure of CO of about 200 psi (1.4 MPa).

The superatmospheric pressure of carbon monoxide may be provided in the form of pure carbon monoxide, or by providing a gas mixture containing carbon monoxide. In certain embodiments, the carbon monoxide may be provided in the form of substantially pure carbon monoxide. In other embodiments, the carbon monoxide may be provided in the form of carbon monoxide mixed with one or more inert gases. In other embodiments, the carbon monoxide may be provided in the form of a mixture of carbon monoxide and hydrogen. In certain embodiments, the carbon monoxide may be provided in the form of a carbon monoxide-containing industrial process gas such as syngas, coal gas, wood gas, or the like.

The temperature of the first step should be maintained in a range where the catalyst, the starting materials, and the products of the carbonylation reaction are stable for the duration of the process, and at a temperature at which the carbonylation reaction proceeds at a rate that allows conversion of starting material in a convenient and economical time-frame. In certain embodiments, the step is performed at a temperature in the range of about −10° C. to about 200° C. In certain embodiments, the step is performed at a temperature in the range of about 0° C. to about 125° C. In certain embodiments, the step is performed at a temperature in the range of about 30° C. to about 100° C. In certain embodiments, the step is performed at a temperature in the range of about 40° C. to about 80° C.

In certain embodiments, the epoxide starting material has the formula

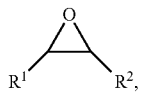

where $R^1$ and $R^2$ are each independently selected from the group consisting of: —H; optionally substituted $C_{1-6}$ aliphatic; optionally substituted $C_{1-6}$ heteroaliphatic; optionally substituted 3- to 6-membered carbocycle; and optionally substituted 3- to 6-membered heterocycle, where $R^1$ and $R^2$ can optionally be taken together with intervening atoms to form a substituted or unsubstituted ring optionally containing one or more heteroatoms.

In certain embodiments, the epoxide is chosen from the group consisting of: ethylene oxide; propylene oxide; 1,2-butylene oxide; 2,3-butylene oxide; epichlorohydrin; cyclohexene oxide; cyclopentene oxide; 3,3,3-Trifluoro-1,2-epoxypropane, styrene oxide; a glycidyl ether; and a glycidyl ester.

In certain embodiments, the epoxide is ethylene oxide.
In certain embodiments, the epoxide is propylene oxide.
In certain embodiments, step 1 includes the reaction shown in Scheme 2:

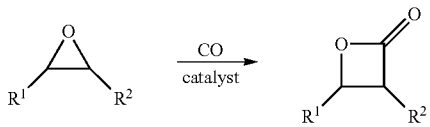

where $R^1$ and $R^2$ are each independently selected from the group consisting of: —H; optionally substituted $C_{1-6}$ aliphatic; optionally substituted $C_{1-4}$ heteroaliphatic; optionally substituted 3- to 6-membered carbocycle; and optionally substituted 3- to 6-membered heterocycle, where $R^1$ and $R^2$ can optionally be taken together with intervening atoms to form a substituted or unsubstituted ring optionally containing one or more heteroatoms.

In certain embodiments, step 1 includes the reaction shown in Scheme 3:

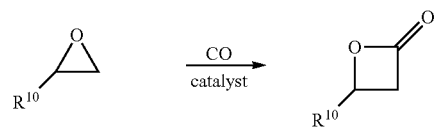

where, $R^{10}$ is selected from the group consisting of —H, and $C_{1-6}$ aliphatic.

In certain embodiments, step 1 includes the reaction shown in Scheme 4:

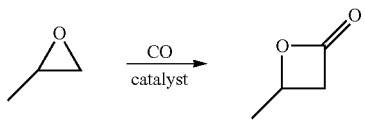

In certain embodiments, step 1 includes the reaction shown in Scheme 5:

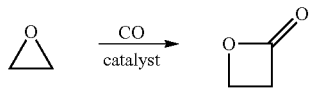

In certain embodiments, the first step is conducted in a continuous flow process whereby the starting epoxide is continuously fed into a reaction stream and the carbonylation takes place as the reaction stream flows through the process. In some embodiments, the epoxide fed into the process is substantially consumed and the reaction stream flowing out of the process contains little or no residual epoxide starting material. It will be understood by those skilled in the art that the process parameters such as reaction temperature, carbon monoxide pressure, catalyst loading, epoxide concentration, agitation, path length, and flow rate, can all be optimized to affect this end.

In certain embodiments, the carbonylation step is performed in a process stream flowing through an adiabatic reaction vessel. In certain embodiments, the adiabatic reaction vessel is a tube reactor. In other embodiments, the carbonylation step is performed in a process stream flowing through a shell and tube reactor.

A subsequent step in processes of the present invention separates the carbonylation catalyst from the propiolactone in the process stream resulting from the carbonylation step by flowing the process stream over any of the OSN nanofiltration membranes described hereinabove. This step produces two streams: a permeate stream and a retentate stream. In certain embodiments, the permeate stream resulting from the nanofiltration step is carried onto an acrylate production step. The acrylate production step is discussed in more detail below. The permeate stream may optionally be processed in a number of ways prior to the acrylate production step. This processing can include, but is not limited to: vacuum-distilling, heating, cooling, or compressing the stream; condensing the stream to a liquid state and carrying forward the liquid; adding a polymerization inhibitor to the stream; condensing selected components to a liquid state and carrying forward the remaining gaseous components; condensing selected components to a liquid state and carrying forward the liquefied components; scrubbing the stream to remove impurities; and any combination of two or more of these.

The other stream resulting from the nanofiltration step is the retentate stream or catalyst recycling stream. In certain embodiments, this stream is returned to the beginning of the process where it re-enters the carbonylation step and is brought into contact with additional epoxide and carbon monoxide. In certain embodiments, the catalyst recycling stream is treated prior to re-entering the carbonylation process. Such treatments can include, but are not limited to: filtering, concentrating, diluting, heating, cooling, or degassing the stream; removing spent catalyst; removing reaction byproducts; adding fresh catalyst; adding one or more catalyst components; and any combination of two or more of these.

Turning next to the acrylate production step, the permeate stream discussed above is carried onward to convert the beta lactone contained therein to acrylic acid or an acrylic acid derivative. As discussed above, in some embodiments, the permeate stream may undergo additional processing steps between the nanofiltration step and the acrylate production step and may enter the acrylate production stage of the process as a gas or as a liquid. The acrylate production step itself may be performed in either the gas phase or the liquid phase and may be performed either neat, or in the presence of a carrier gas, solvent or other diluent.

In certain embodiments, the acrylate production step is performed in a continuous flow format. In certain embodiments, the acrylate production step is performed in a continuous flow format in the gas phase. In certain embodiments, the acrylate production step is performed in a continuous flow format in the liquid phase. In certain embodiments, the acrylate production step is performed in a liquid phase in a batch or semi-batch format.

The acrylate production step may be performed under a variety of conditions. In certain embodiments, the reaction may be performed in the presence of one or more catalysts that facilitate one or more steps in the transformation of the beta lactone intermediate to the acrylate product. Many catalysts known in the art can be used, or adapted for this step. In some embodiments, conditions include reaction with dehydrating agents such as sulfuric acid, phosphoric acid or esters thereof as described in U.S. Pat. Nos. 2,352,641; 2,376,704; 2,449,995; 2,510,423; 2,623,067; 3,176,042, and in British Patent No. GB 994.091, the entirety of each of which is incorporated herein by reference.

In other embodiments, the lactone can be reacted with a halogen-containing compound to yield a beta halo acid, beta halo ester, or beta halo acid halide which may then undergo dehydrohalogenation and/or solvolysis to afford the corresponding acrylic acid or acrylic ester. In certain embodiments, conditions disclosed in U.S. Pat. No. 2,422,728 (incorporated herein by reference) are used in this process.

In other embodiments, the acrylate production may be base catalyzed, see for example *Journal of Organic Chemistry*, 57(1), 389-91(1992) and references therein, the entirety of which is incorporated herein by reference.

In certain embodiments, the acrylate production stage of the process may be performed by combining the permeate stream from the previously described steps with an alcohol vapor and passing the mixture in the gas phase through a column of a solid, or solid supported promoter that effects the conversion to an acrylic ester. In certain embodiments, this process is performed over a promoter including activated carbon according to the methods of U.S. Pat. No. 2,466,501 the entirety of which is incorporated herein by reference.

In some embodiments, the beta lactone in the permeate stream is allowed to polymerize and acrylic acid or derivatives thereof are obtained by decomposition of the polymer. In certain embodiments, the beta lactone is propiolactone and the polymer is poly(3-hydroxy propionic acid) (3-HPA). In certain embodiments, the 3-HPA is formed and decomposed using the methods described in U.S. Pat. Nos. 2,361,036; 2,499,988; 2,499,990; 2,526,554; 2,568,635; 2,568,636; 2,623,070; and 3,002,017, the entirety of each of which is incorporated herein by reference.

In certain embodiments, the beta lactone product stream is reacted with a nucleophile of the formula Y—H. In certain embodiments, Y is selected from the group consisting of halogen; —$OR^{13}$; —$NR^{11}R^{12}$; and —$SR^{13}$, where $R^{11}$, $R^{12}$, and $R^{13}$ are independently selected from the group consisting of: —H; optionally substituted $C_{1-32}$ aliphatic; optionally substituted $C_{1-32}$ heteroaliphatic; optionally substituted 3- to 14-membered carbocycle; and optionally substituted 3- to 14-membered heterocycle, and where $R^{11}$ and $R^{12}$ can optionally be taken together with intervening atoms to form an optionally substituted ring optionally containing one or more heteroatoms.

In certain embodiments, the beta lactone product stream is reacted with a nucleophile of the formula Y—H to afford an acrylate having the formula I:

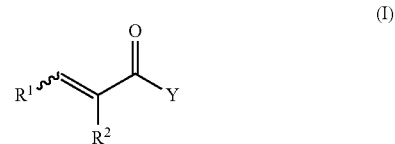

(I)

In certain embodiments, Y—H is an amine having the formula $R^{11}R^{12}N$—H, and the product is an acrylamide. In certain embodiments, this process uses conditions disclosed in U.S. Pat. Nos. 2,548,155; 2,649,438; 2,749,355; and 3,671,305, the entirety of each of which is incorporated herein by reference.

In certain embodiments, the beta lactone product stream is reacted with a nucleophile of the formula Y—H to afford an acid having the formula II:

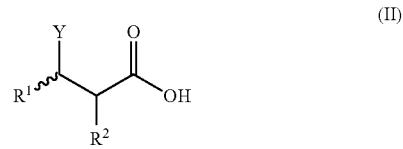

(II)

In certain embodiments, compounds of formula II are obtained using conditions disclosed in U.S. Pat. Nos. 2,449,992; 2,449,989; 2,449,991; 2,449,992; and 2,449,993, the entirety of each of which is incorporated herein by reference.

In certain embodiments, where the beta lactone product stream is reacted with a nucleophile of the formula Y—H to afford an acid having the formula II, and Y is —OR$^{13}$; —NR$^{11}$R$^{12}$; or —SR$^{13}$, the acid is dehydrated to yield an acrylate of formula I.

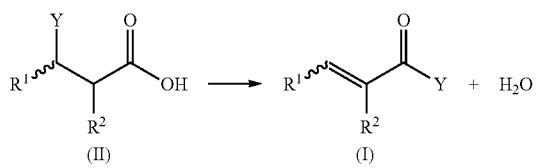

In certain embodiments, the conversion of II to I is performed according to the methods and conditions of U.S. Pat. No. 2,376,704 the entirety of which is incorporated herein by reference.

In certain embodiments, the acrylate product stream resulting from the preceding steps may undergo additional purification steps. In certain embodiments, the stream is purified according to methods disclosed in U.S. Pat. Nos. 3,124,609; 3,157,693; 3,932,500; 4,828,652; 6,084,122; 6,084,128; and 6,207,022, the entirety of each of which is incorporated herein by reference.

In certain embodiments, the present invention includes methods for the production of acrylates from epoxides in a continuous flow process, the process including the steps of a) contacting a process stream including an epoxide and an organic solvent with a carbonylation catalyst in the presence of carbon monoxide to provide a reaction stream containing a beta lactone formed from the epoxide, where the organic solvent comprises an ether, b) applying the reaction stream to any nanofiltration membrane described above and in the classes and subclasses herein to produce a carbonylation permeate stream including beta lactone and a first portion of the organic solvent and a retentate stream including carbonylation catalyst and a second portion of the organic solvent, and c) treating the permeate product stream under conditions to convert the beta lactone into an acrylate.

In certain embodiments, the process further includes the step of returning the retentate stream to step a).

In certain embodiments, the process further includes treating the catalyst recycling stream by performing at least one step selected from the group consisting of adding fresh catalyst, removing spent catalyst, adding solvent, adding epoxide, and any combination of two or more of these.

In some embodiments, step c) of the process is performed in the presence of a compound selected from the group consisting of: an alcohol, an amine, and a thiol, under conditions that afford the corresponding acrylic ester, acrylamide, or a thioacrylate respectively.

In certain embodiments, the invention provides a method for the production of an acrylate ester from ethylene oxide in a continuous flow process, the method comprising the steps of:
a) contacting a process stream comprising ethylene oxide and an ether solvent with a carbonylation catalyst in the presence of carbon monoxide to provide a reaction stream containing beta propiolactone formed from the ethylene oxide;
b) applying the reaction stream containing the beta propiolactone to any nanofiltration membrane as described above and in the classes and subclasses herein to produce:
  i) a permeate stream comprising beta propiolactone and a first portion of the organic solvent, and
  ii) a retentate stream comprising carbonylation catalyst and a second portion of the organic solvent; and
c) treating the permeate stream under conditions to convert the beta propiolactone into an acrylate ester;
optionally further comprising the step of returning the retentate stream to step (a);
  optionally further comprising treating the retentate stream prior to returning it to step (a) where the step of treating is selected from the group consisting of: adding fresh catalyst, removing spent catalyst; adding solvent; adding epoxide; and any combination of two or more of these.

In certain embodiments, the invention provides a method for the production of poly(3-hydroxy propionic acid) from ethylene oxide in a continuous flow process, the method comprising the steps of:
a) contacting a process stream comprising ethylene oxide and an ether with a carbonylation catalyst in the presence of carbon monoxide to provide a reaction stream containing beta propiolactone formed from the ethylene oxide;
b) applying the reaction stream containing the beta propiolactone to a nanofiltration membrane described above and in the classes and subclasses herein to produce:
  i) a permeate stream comprising beta propiolactone and a first portion of the organic solvent, and
  ii) a retentate stream comprising carbonylation catalyst and a second portion of the organic solvent; and
c) treating the permeate stream under conditions to convert the beta propiolactone into poly(3-hydroxy propionic acid);
optionally further comprising the step of returning the retentate stream to step (a);
optionally further comprising treating the retentate stream prior to returning it to step (a) where the step of treating is selected from the group consisting of: adding fresh catalyst, removing spent catalyst; adding solvent; adding epoxide; and any combination of two or more of these.

In certain embodiments of any of the above-described methods or uses, the nanofiltration membrane comprises a polysiloxane polymer, wherein the polysiloxane polymer comprises less than 500 nmol of free —Si(OH)— containing groups per gram of polysiloxane.

In certain embodiments of any of the above-described methods or uses, the nanofiltration membrane comprises a co-polymer, the co-polymer comprising a monomer of Formula M1 and one or more monomers of Formulae M1a, M2 and M3. In some embodiments, the co-polymer comprises a monomer of Formulae M2a to M2j. In some embodiments, the co-polymer comprises a monomer of Formulae M3a or M3b.

In certain embodiments of any of the above-described methods or uses, the nanofiltration membrane comprises a co-polymer, the co-polymer comprising a monomer of Formula M4 and one or more of a monomer of Formula M5 and a group of Formula M6. In some embodiments, the co-polymer comprises a monomer of Formulae M5a to M5j.

In certain embodiments of any of the above-described methods or uses, the nanofiltration membrane comprises a co-polymer, the co-polymer comprising a monomer of Formula M4 and a monomer of Formula M13. In some embodiments, the co-polymer comprises a monomer of Formulae M13a to M13d.

In certain embodiments of any of the above-described methods or uses, the nanofiltration membrane comprises a co-polymer, the co-polymer comprising (i) a monomer of Formulae M7, M8 or M9, and (ii) a monomer of Formulae M10 or M11, and/or a group of Formulae M12 or M6.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of carbonylating epoxide comprising the steps of:

a) contacting epoxide with carbon monoxide in the presence of a homogenous carbonylation catalyst to provide a process stream comprising beta lactone and the homogenous catalyst, b) flowing the process stream over a nanofiltration membrane to provide a permeate stream comprising beta lactone and a retentate stream comprising homogenous catalyst, and c) returning the retentate stream to step (a), wherein the concentration of the catalyst in the retentate stream is higher than the catalyst concentration in the permeate stream; and wherein the nanofiltration membrane comprises a co-polymer, the co-polymer comprising a monomer of Formula M1 and one or more monomers of Formulae M1a, M2 and M3:

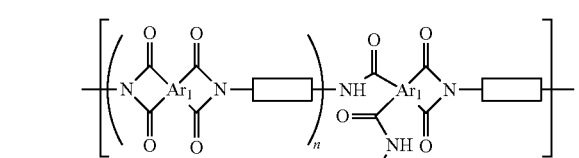

M1

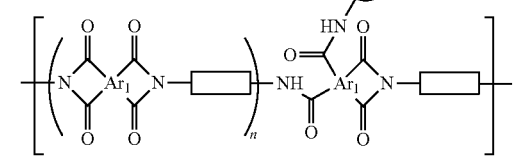

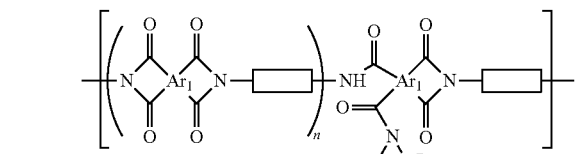

M1a

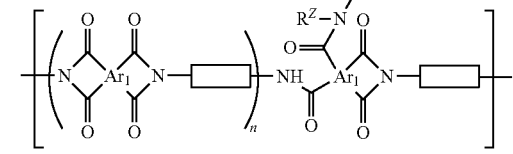

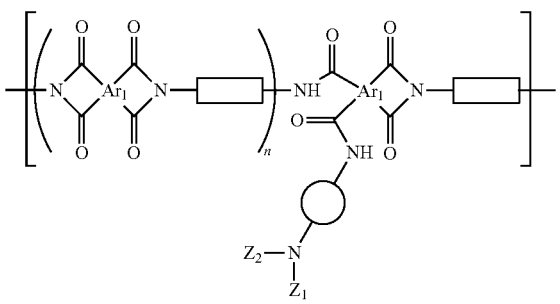

M2

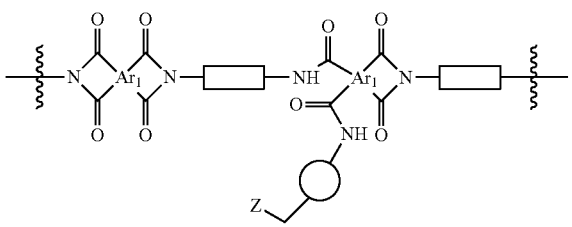

M3 wherein:

each $Ar_1$ is a tetravalent aromatic moiety;

each

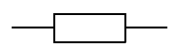

represents a bivalent linker and may be the same or different at each occurrence in the co-polymer;

each

represents a bivalent linker and may be the same or different at each occurrence in the co-polymer;

n is any integer up to about 100,000;

Z is a functional group that does not contain a nitrogen atom;

$Z_1$ is H, aliphatic, acyl or aryl;

$Z_2$ is selected from the group consisting of: aliphatic, aryl, acyl, —C(O)OR$^x$, —SO$_2$R$^x$ and —C(O)NHR$^x$;

where $Z_1$ and $Z_2$ may optionally be taken together to form a ring, $R^z$ is an optionally substituted aliphatic or optionally substituted aromatic group; and $R^x$ is an optionally substituted aliphatic or optionally substituted aromatic group.

2. The method of claim 1, wherein the co-polymer comprises a monomer of Formulae M2a to M2j:

M2a
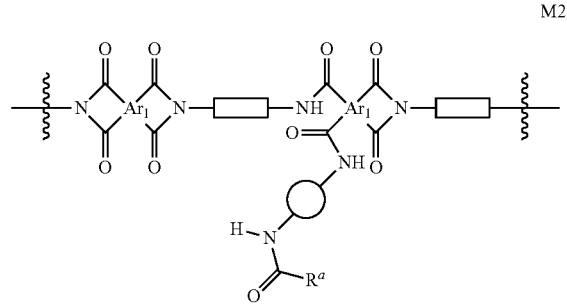

M2b
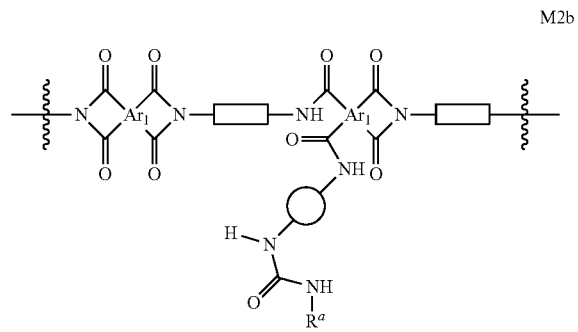

M2c
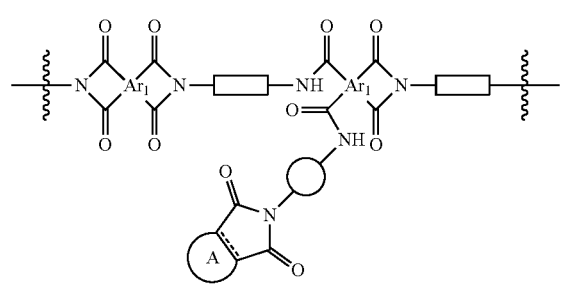

M2d
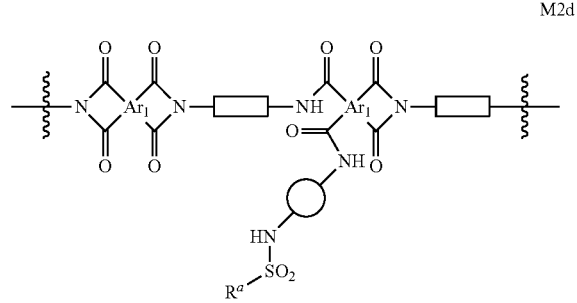

M2e
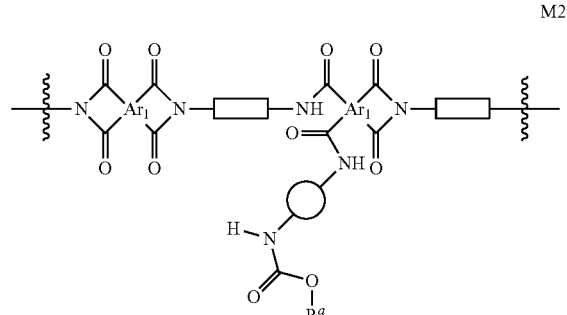

M2f
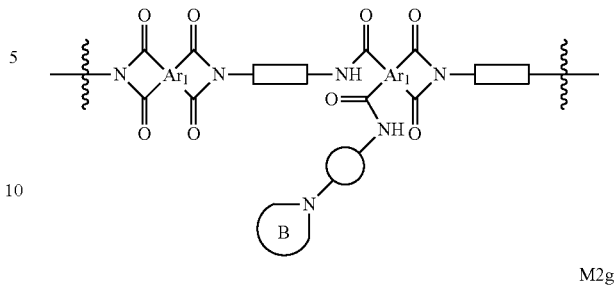

M2g
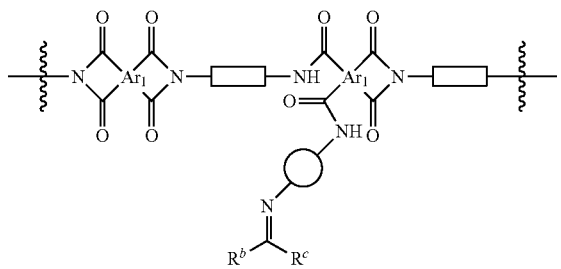

M2h
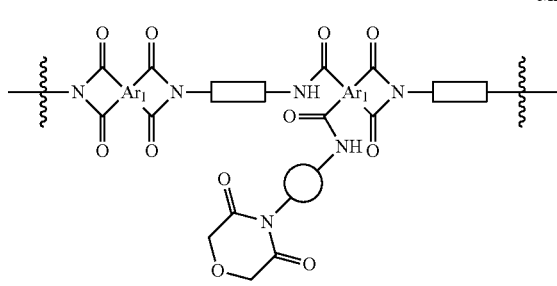

M2i
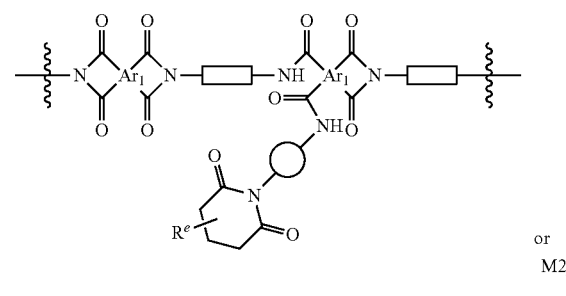

or

M2j
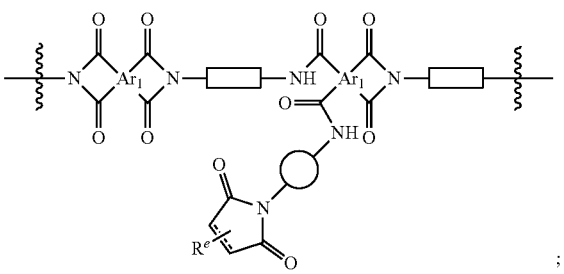

;

wherein:
$R^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl;

each of $R^b$ and $R^c$ are independently selected from the group consisting of: —H; optionally substituted $C_1$ to $C_{12}$ aliphatic; optionally substituted 3- to 14-membered carbocyclic; and optionally substituted 3- to 14 membered heterocyclic, where $R^b$ and $R^c$ may be taken together with intervening atoms to form one or more optionally substituted rings;

$R^e$ is one or more moieties selected from the group consisting of: —H, halogen, —OR, —NR$_2$, —SR, —CN, —SO$_2$R, —SOR, —CO$_2$R, —C(O)R, —OC(O)R, SO$_2$NR$_2$; —CNO, —NRSO$_2$R, —N$_3$, —SiR$_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

R is H, optionally substituted aliphatic or optionally substituted aromatic;

⫘ is a single or double bond;

ring A is an optionally substituted aryl ring or an optionally substituted saturated or partially unsaturated mono- or polycyclic ring optionally containing one or more heteroatoms selected from the group consisting of nitrogen, oxygen, and sulfur; and ring B represents an optionally substituted 5- or 6-membered saturated, partially unsaturated or aromatic ring optionally containing one or more additional heteroatoms, selected from the group consisting of nitrogen, oxygen, and sulfur, which may be part of a larger fused ring system.

3. The method of claim 1, wherein the co-polymer comprises a monomer of Formulae M3a or M3b:

M3a

M3b wherein $X^b$ is Cl, Br or I.

4. The method of claim 1, wherein each Ar$_1$ is independently selected from the group consisting of:

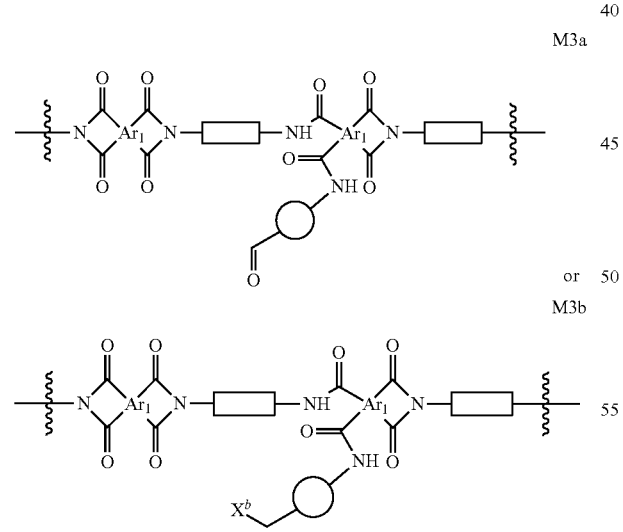

; and

Q is selected from the group consisting of:

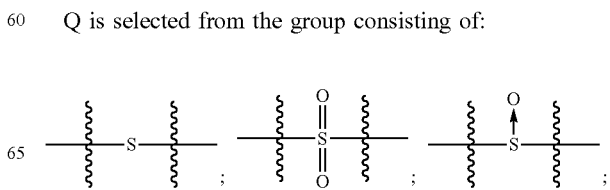

-continued

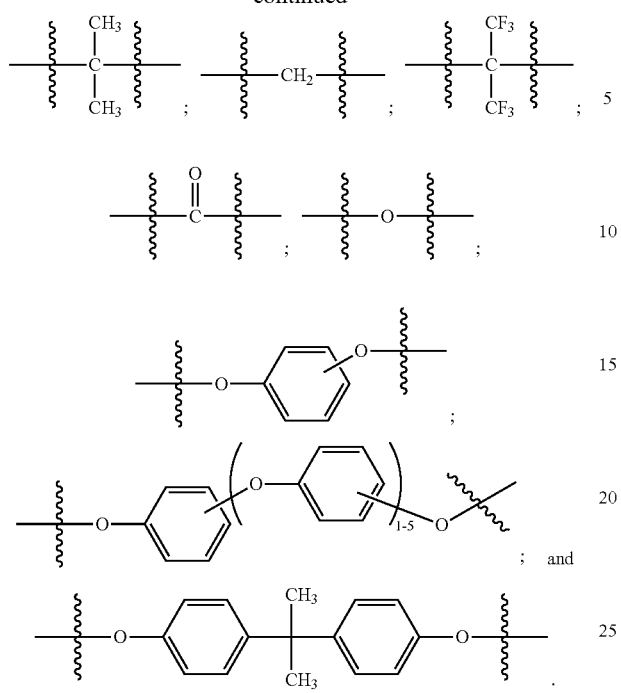

5. A method of carbonylating epoxide comprising the steps of:

a) contacting epoxide with carbon monoxide in the presence of a homogenous carbonylation catalyst to provide a process stream comprising beta lactone and the homogenous catalyst, b) flowing the process stream over a nanofiltration membrane to provide a permeate stream comprising beta lactone and a retentate stream comprising homogenous catalyst, and c) returning the retentate stream to step (a), wherein the concentration of the catalyst in the retentate stream is higher than the catalyst concentration in the permeate stream; and wherein said nanofiltration membrane comprises a co-polymer, the co-polymer comprising a monomer of Formula M4 and one or more of a monomer of Formula M5 and a group of Formula M6:

M4

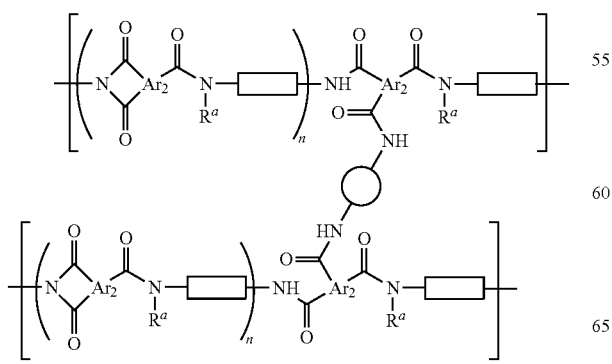

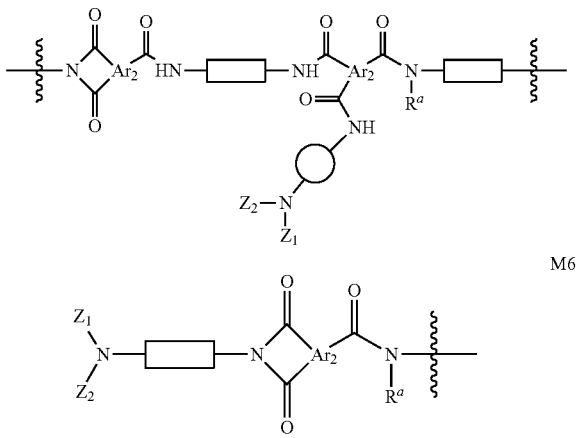

wherein:
each $Ar_2$ is a trivalent aromatic moiety;
each

represents a bivalent linker and may be the same or different at each occurrence in the co-polymer;
each

represents a bivalent linker and may be the same or different at each occurrence in the co-polymer;
n is any integer up to about 100,000;
$Z_1$ is —H, aliphatic, acyl, or aryl;
$Z_2$ is selected from the group consisting of: aliphatic, aryl, acyl, —C(O)OR$^x$, —SO$_2$R$^x$, and —C(O)NHR$^x$;
where $Z_1$ and $Z_2$ may optionally be taken together to form a ring;
R$^x$ is an optionally substituted aliphatic or optionally substituted aromatic group; and
R$^a$ is —H, or an optionally substituted radical selected from the group consisting of C$_{1-20}$ aliphatic, C$_{1-20}$ heteroaliphatic, 3- to 12-membered heterocyclic, and 6- to 12-membered aryl.

6. The method of claim 5, wherein the co-polymer comprises a monomer of Formulae M5a to M5j:

M5a

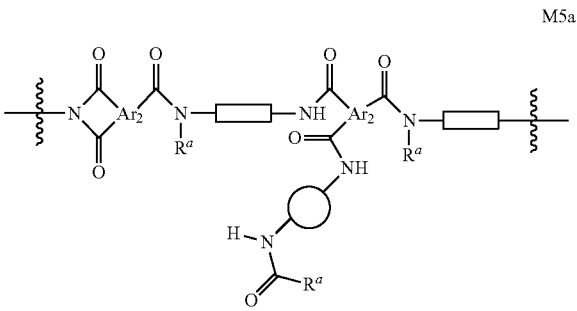

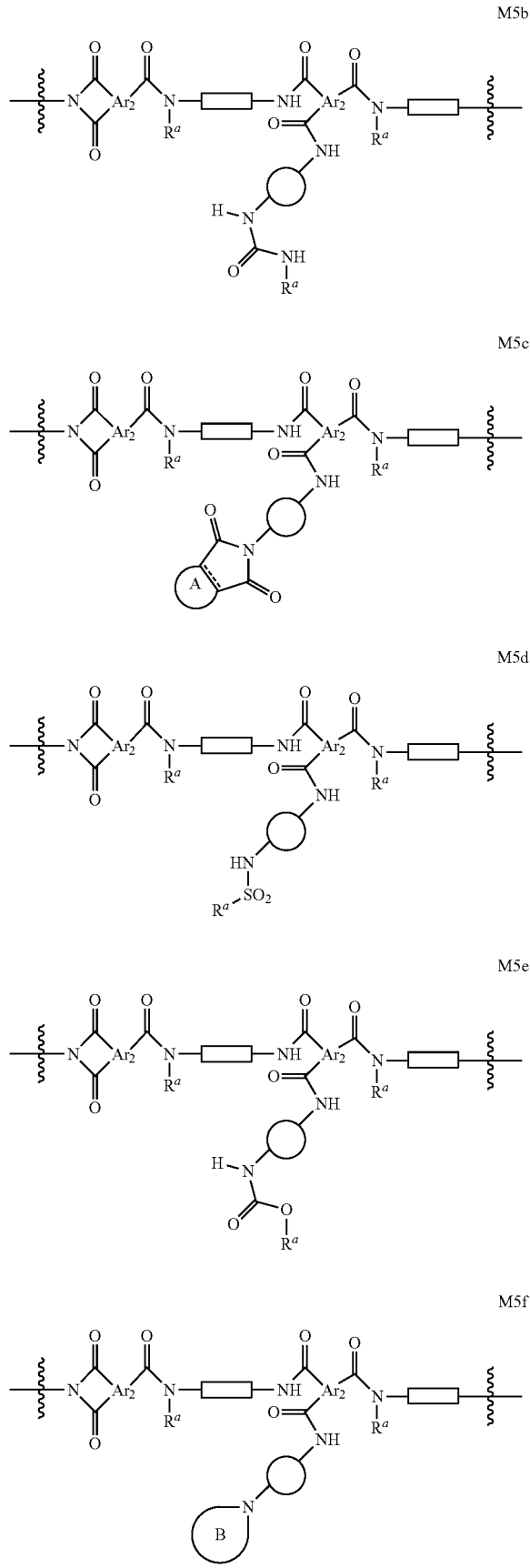
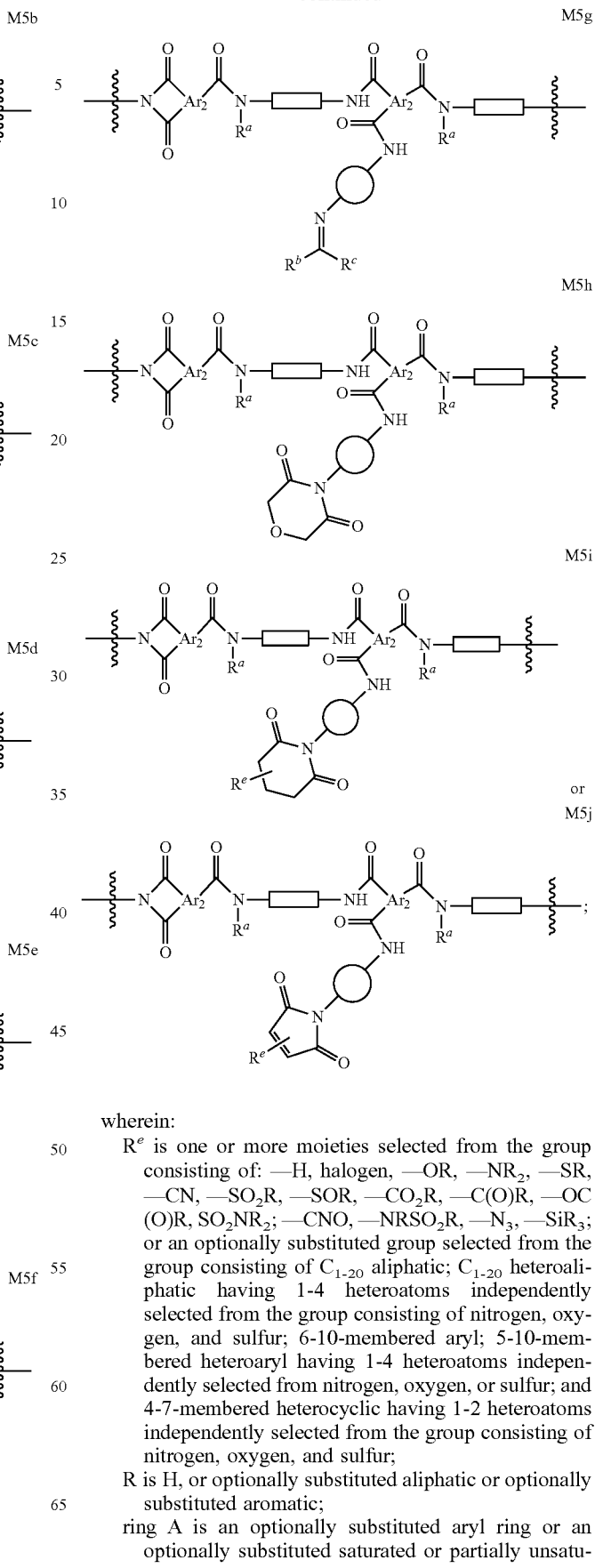

wherein:
R$^e$ is one or more moieties selected from the group consisting of: —H, halogen, —OR, —NR$_2$, —SR, —CN, —SO$_2$R, —SOR, —CO$_2$R, —C(O)R, —OC(O)R, SO$_2$NR$_2$; —CNO, —NRSO$_2$R, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

R is H, or optionally substituted aliphatic or optionally substituted aromatic;

ring A is an optionally substituted aryl ring or an optionally substituted saturated or partially unsaturated mono- or polycyclic ring optionally containing one or more heteroatoms selected from the group consisting of nitrogen, oxygen, and sulfur; and ring B represents an optionally substituted 5- or 6-membered saturated, partially unsaturated or aromatic ring optionally containing one or more additional heteroatoms, selected from the group consisting of nitrogen, oxygen, and sulfur, which may be part of a larger fused ring system.

7. The method of claim 5, wherein
each $Ar_2$ is independently selected from the group consisting of:

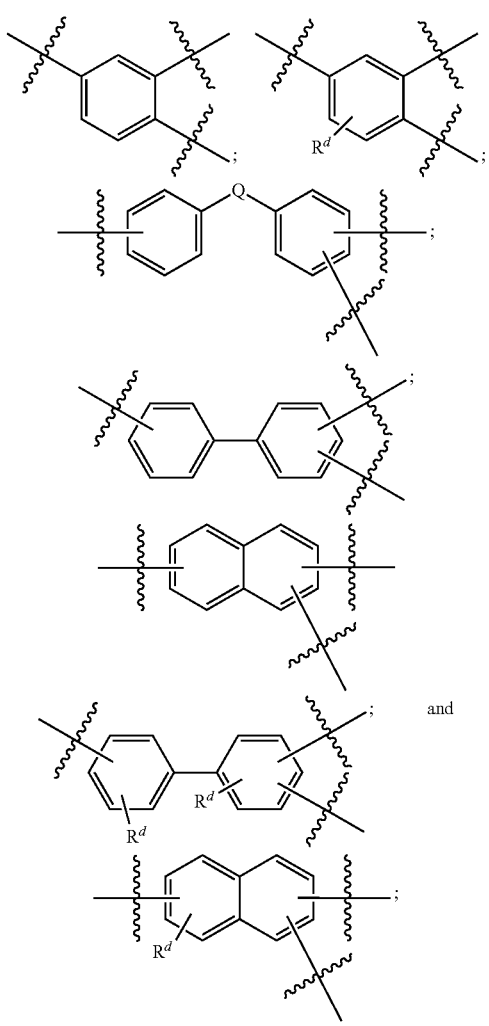

and
Q is selected from the group consisting of:

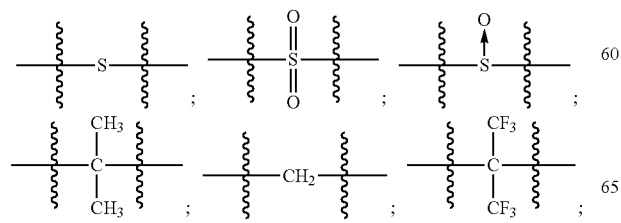

8. The method of claim 1, wherein each

is independently a bivalent $C_{2-20}$ aliphatic group, bivalent aromatic group, or derives from a bivalent diamine group

9. The method of claim 1, wherein (i) each

—◯— is —$CH_2CH_2$—; —$CH_2CH_2CH_2$—; —$CH_2(CH_2)_2CH_2$—; —$CH_2(CH_2)_3CH_2$—; —$CH_2(CH_2)_4CH_2$—; —$CH_2(CH_2)_6CH_2$—; —$CH_2(CH_2)_8CH_2$—; —$CH_2(CH_2)_{10}CH_2$—; —$CH_2(CH_2)_{12}CH_2$—; —$CH_2(CH_2)_{14}CH_2$—; or —$CH_2(CH_2)_{16}CH_2$—.

10. The method of claim 1, wherein (i) each

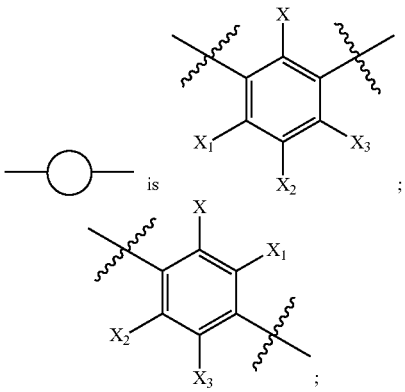

137
-continued

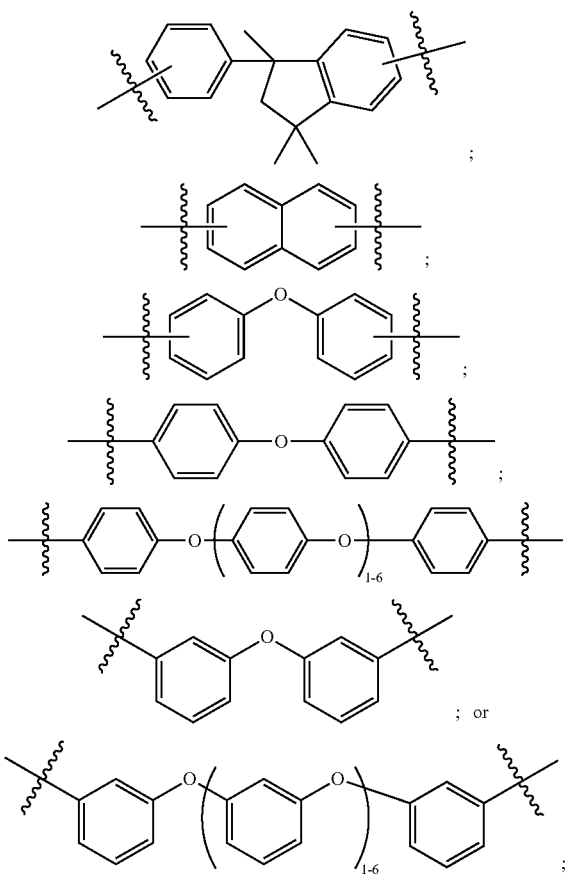

wherein each X, X₁, X₂ and X₃ is independently hydrogen, halogen, or an optionally substituted moiety selected from the group consisting of halogen, aliphatic, alkoxy, phenoxy, aryl, and phenyl; and Q is selected from the group consisting of:

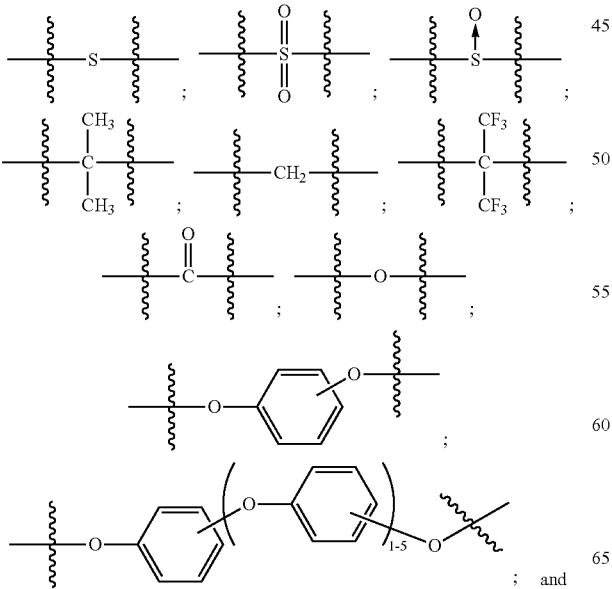

138
-continued

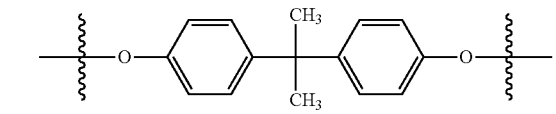

11. The method of claim 1, wherein each

derives from a bivalent diamine group,

selected from the group consisting of:

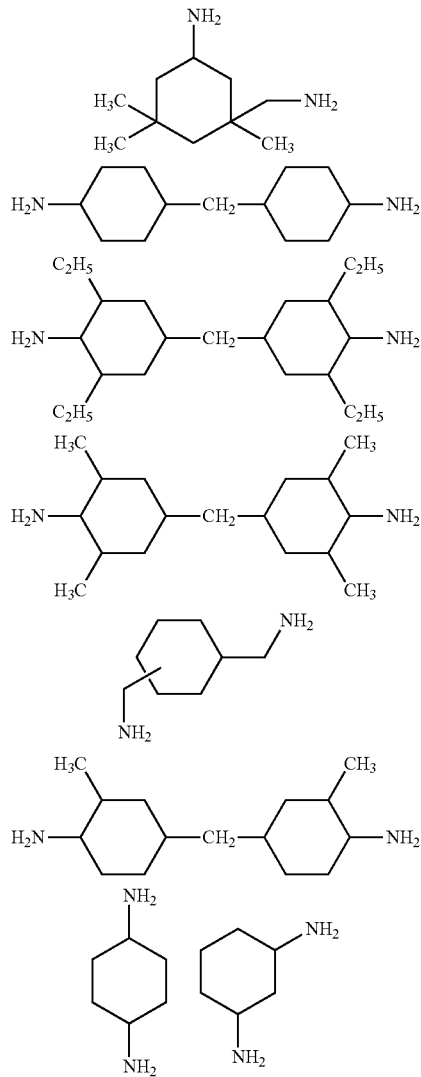

-continued

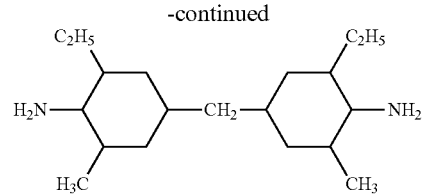

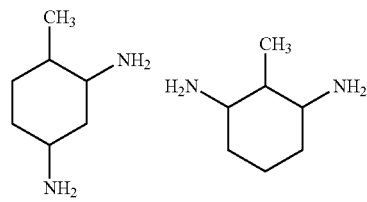

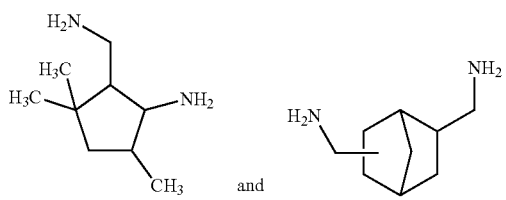

and

12. The method of claim 1, wherein the nanofiltration membrane has reduced chemical activity toward a reactive feedstock or product comprising a carbonylation catalyst.

13. A method of carbonylating epoxide comprising the steps of:
   a) contacting epoxide with carbon monoxide in the presence of a homogenous carbonylation catalyst to provide a process stream comprising beta lactone and the homogenous catalyst,
   b) flowing the process stream over a nanofiltration membrane to provide a permeate stream comprising beta lactone and a retentate stream comprising homogenous catalyst, and
   c) returning the retentate stream to step (a),
   wherein the concentration of the catalyst in the retentate stream is higher than the catalyst concentration in the permeate stream; and
   wherein said nanofiltration membrane comprises a co-polymer, the co-polymer comprising a monomer of Formula M4 and a monomer of Formula M13:

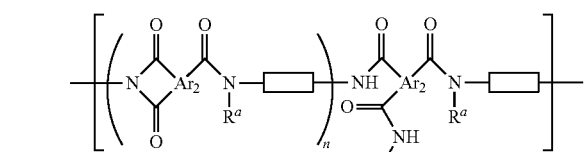

M4

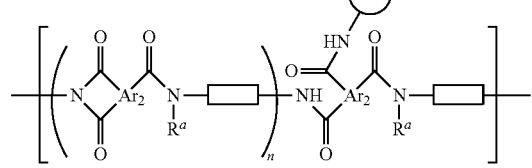

-continued

M13

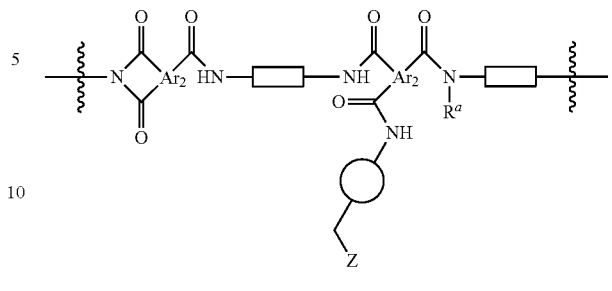

wherein:
each $Ar_2$ is a trivalent aromatic moiety;
each

represents a bivalent linker and may be the same or different at each occurrence in the co-polymer;
each

represents a bivalent linker and may be the same or different at each occurrence in the co-polymer;
n is any integer up to about 100,000;
Z is a functional group that does not contain a nitrogen atom; and
$R^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl.

14. The method of claim 13, wherein the co-polymer comprises a monomer of Formulae M13a to M13d:

M13a

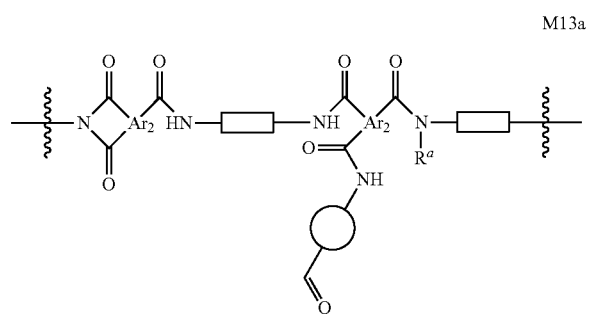

M13b

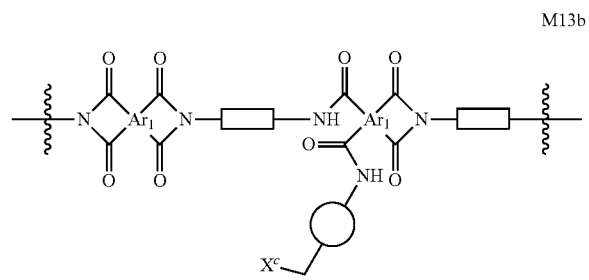

-continued

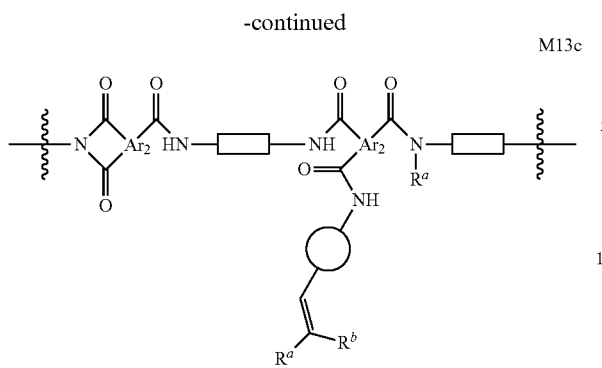

M13c

M13d wherein
$X^c$ is Cl, Br or I.

15. The method of claim 13, wherein
each $Ar_2$ is independently selected from the group consisting of:

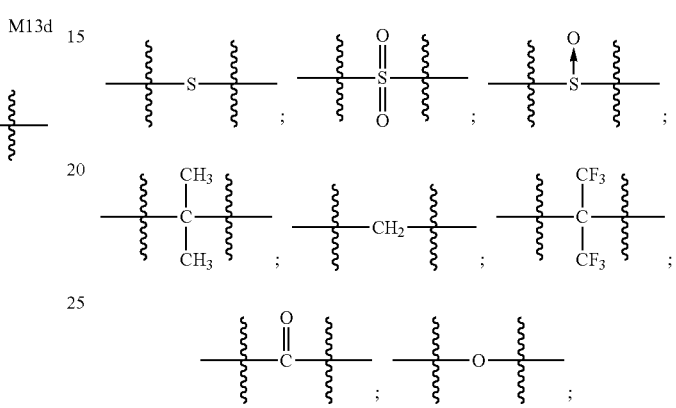

-continued

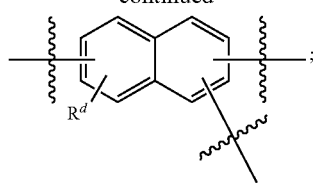

and
Q is selected from the group consisting of:

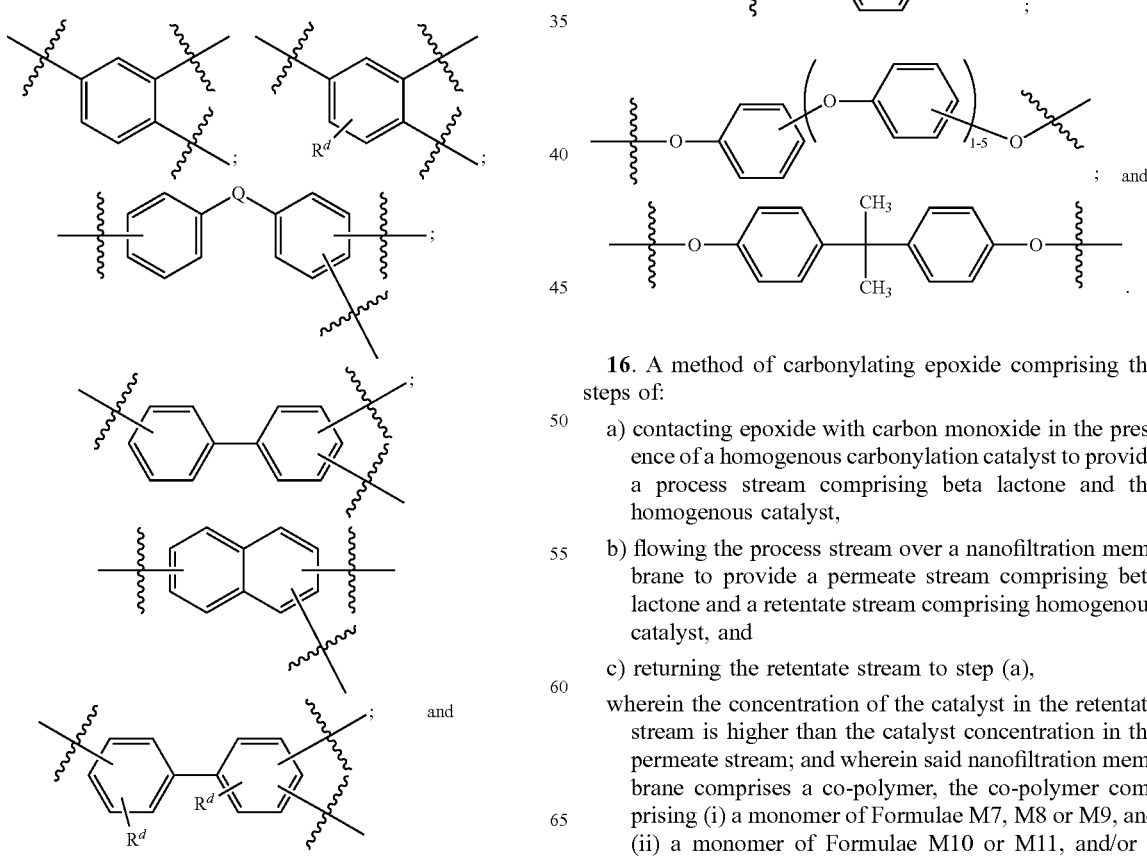

16. A method of carbonylating epoxide comprising the steps of:
a) contacting epoxide with carbon monoxide in the presence of a homogenous carbonylation catalyst to provide a process stream comprising beta lactone and the homogenous catalyst,
b) flowing the process stream over a nanofiltration membrane to provide a permeate stream comprising beta lactone and a retentate stream comprising homogenous catalyst, and
c) returning the retentate stream to step (a),
wherein the concentration of the catalyst in the retentate stream is higher than the catalyst concentration in the permeate stream; and wherein said nanofiltration membrane comprises a co-polymer, the co-polymer comprising (i) a monomer of Formulae M7, M8 or M9, and (ii) a monomer of Formulae M10 or M11, and/or a group of Formulae M12 or M6:

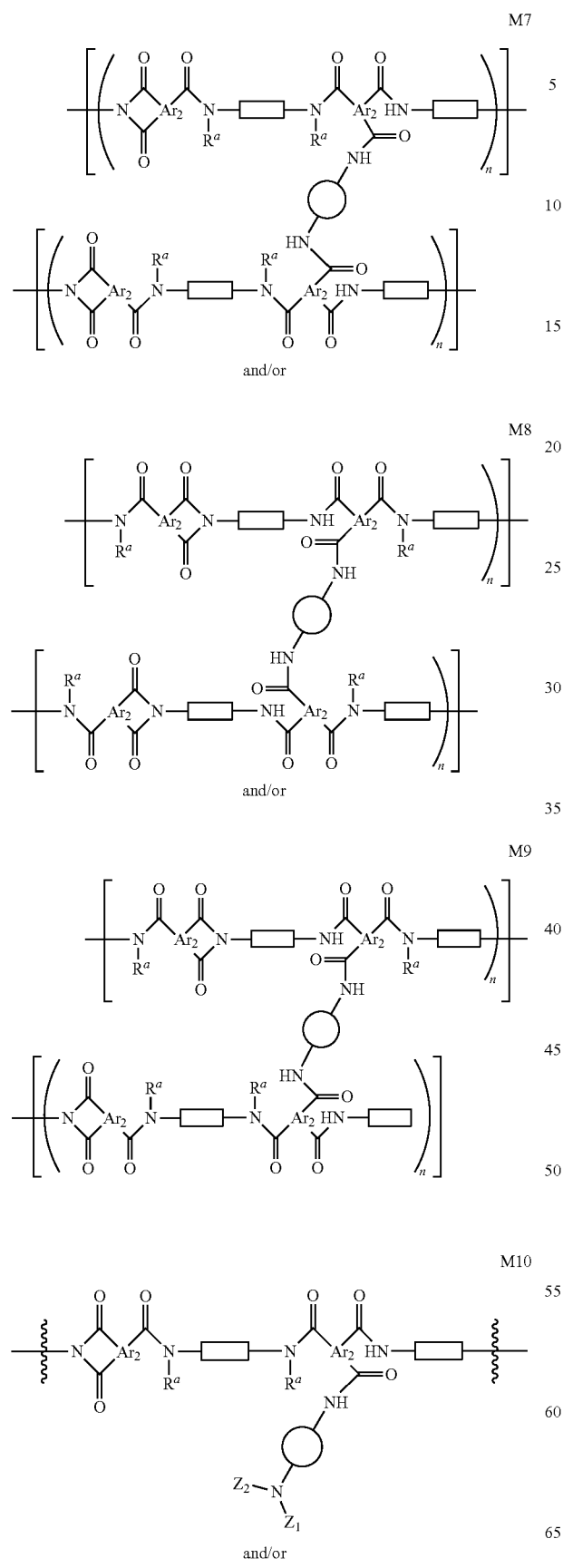

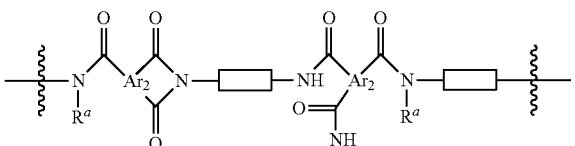

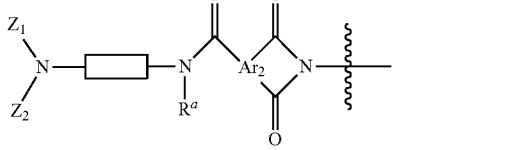

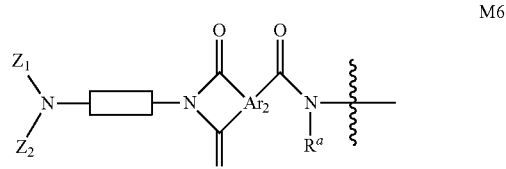

wherein:
each $Ar_2$ is a trivalent aromatic moiety;
each

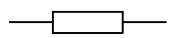

represents a bivalent linker and may be the same or different at each occurrence in the co-polymer;
each

represents a bivalent linker and may be the same or different at each occurrence in the co-polymer;
n is any integer up to about 100,000;
$Z_1$ is —H, aliphatic, acyl, or aryl;
$Z_2$ is selected from the group consisting of: aliphatic, aryl, acyl, —C(O)OR$^x$, —SO$_2$R$^x$, and —C(O)NHR$^x$;
R$^x$ is an optionally substituted aliphatic or optionally substituted aromatic group;
where $Z_1$ and $Z_2$ may optionally be taken together to form a ring; and
R$^a$ is —H, or an optionally substituted radical selected from the group consisting of $C_{1-20}$ aliphatic, $C_{1-20}$ heteroaliphatic, 3- to 12-membered heterocyclic, and 6- to 12-membered aryl.

17. The method of claim 16, wherein
each $Ar_2$ is independently selected from the group consisting of:

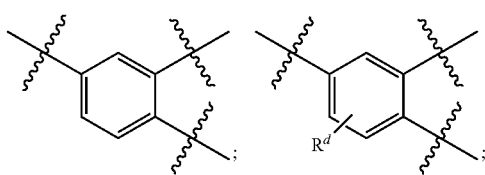
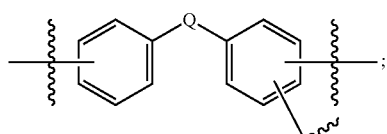
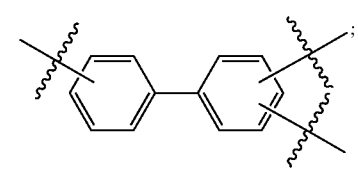
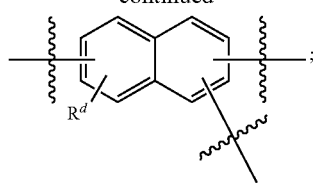
and
Q is selected from the group consisting of:
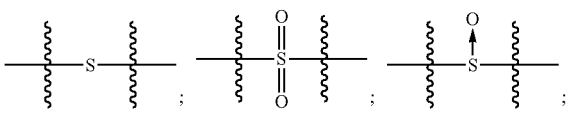
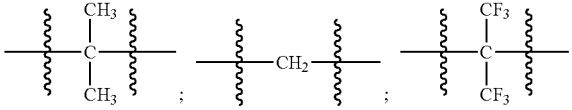
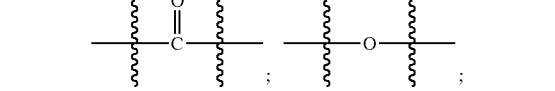
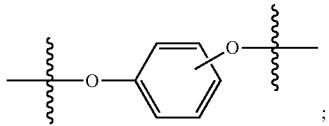
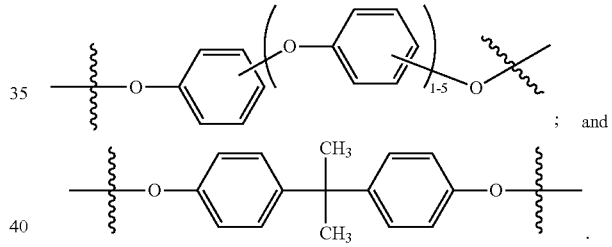
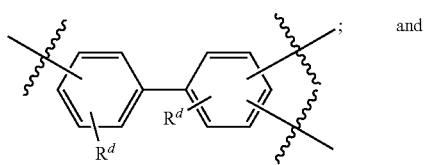
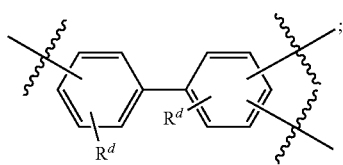
* * * * *